US012631532B2

(12) United States Patent
Chen et al.

(10) Patent No.: US 12,631,532 B2
(45) Date of Patent: May 19, 2026

(54) APPARATUS AND METHODS FOR LASER-BASED SINGLE CELL RECOVERY FROM MICROCAPILLARY ARRAYS

(71) Applicant: xCella Biosciences, Inc., Emeryville, CA (US)

(72) Inventors: Bob Chen, San Diego, CA (US); Austin Blanco, San Diego, CA (US); Ryan Lewis Kelly, San Diego, CA (US); Frances Liu, San Diego, CA (US); Derek Croote, San Diego, CA (US); Samuel Timothy Hatch, San Diego, CA (US)

(73) Assignee: xCella Biosciences, Inc., Emeryville, CA (US)

( * ) Notice: Subject to any disclaimer, the term of this patent is extended or adjusted under 35 U.S.C. 154(b) by 1046 days.

(21) Appl. No.: 17/755,688

(22) PCT Filed: Nov. 6, 2020

(86) PCT No.: PCT/US2020/059485
§ 371 (c)(1),
(2) Date: May 5, 2022

(87) PCT Pub. No.: WO2021/092442
PCT Pub. Date: May 14, 2021

(65) Prior Publication Data
US 2022/0373440 A1 Nov. 24, 2022

Related U.S. Application Data

(60) Provisional application No. 62/932,989, filed on Nov. 8, 2019.

(51) Int. Cl.
*G01N 1/00* (2006.01)
*C12N 15/10* (2006.01)
(Continued)

(52) U.S. Cl.
CPC ........... *G01N 1/44* (2013.01); *C12N 15/1065* (2013.01); *C12N 15/1096* (2013.01);
(Continued)

(58) Field of Classification Search
None
See application file for complete search history.

(56) References Cited

U.S. PATENT DOCUMENTS 4,004,150 A 1/1977 Natelson
4,017,185 A 4/1977 Chupp
(Continued)

FOREIGN PATENT DOCUMENTS

AU 6027873 3/1975
CA 994009 7/1976
(Continued)

OTHER PUBLICATIONS

Carl Zeiss, 2007, Objective LD "Plan-Neofluar" 40x/0.6 Corr www.micro-shop.zeiss.com Mar. 13, 2007, 2 pp.
(Continued)

*Primary Examiner* — Jyoti Mutreja
(74) *Attorney, Agent, or Firm* — KNOBBE, MARTENS, OLSON & BEAR, LLP

(57) ABSTRACT

Systems and methods for recovering content of a sample from a microcapillary array are provided. The microcapillary array includes a plurality of microcapillary wells. A laser is positioned to target a first microcapillary well in the plurality of microcap-wells. The laser pulses at least one time at the first microcapillary well. The content from the first microcapillary well is extracted, recovering the content of the first microcapillary well.

27 Claims, 24 Drawing Sheets

(51) Int. Cl.
| | |
|---|---|
| *C12Q 1/6806* | (2018.01) |
| *G01N 1/31* | (2006.01) |
| *G01N 1/42* | (2006.01) |
| *G01N 1/44* | (2006.01) |
| G02B 26/10 | (2006.01) |
| G02B 27/09 | (2006.01) |

(52) U.S. Cl.
CPC ........... *C12Q 1/6806* (2013.01); *G01N 1/312* (2013.01); *G01N 1/42* (2013.01); *G02B 26/105* (2013.01); *G02B 27/0977* (2013.01)

(56) References Cited

U.S. PATENT DOCUMENTS

| | | | |
|---|---|---|---|
| 4,111,754 A | 9/1978 | Park |
| 4,498,782 A | 2/1985 | Proctor et al. |
| 4,621,059 A | 11/1986 | Rokugawa |
| 4,762,420 A | 8/1988 | Bowley |
| 4,960,566 A | 10/1990 | Mochida |
| 4,968,148 A | 11/1990 | Chow et al. |
| 5,072,382 A | 12/1991 | Kamentsky |
| 5,073,029 A | 12/1991 | Eberly et al. |
| 5,112,134 A | 5/1992 | Chow et al. |
| 5,262,129 A | 11/1993 | Terada et al. |
| 5,265,169 A | 11/1993 | Ohta et al. |
| 5,389,555 A | 2/1995 | Watanabe et al. |
| 5,675,155 A | 10/1997 | Pentoney et al. |
| 5,730,187 A | 3/1998 | Howitz et al. |
| 5,763,263 A | 6/1998 | Dehlinger |
| 5,766,875 A | 6/1998 | Hafeman et al. |
| 5,774,214 A | 6/1998 | Prettyjohns |
| 5,843,767 A | 12/1998 | Beattie |
| 5,854,684 A | 12/1998 | Stabile et al. |
| 6,027,873 A | 2/2000 | Schellenberger et al. |
| 6,071,748 A | 6/2000 | Modlin et al. |
| 6,143,496 A | 11/2000 | Brown et al. |
| 6,174,673 B1 | 1/2001 | Short et al. |
| 6,246,525 B1 | 6/2001 | Ikami |
| 6,306,578 B1 | 10/2001 | Schellenberger et al. |
| 6,345,115 B1 | 2/2002 | Ramm et al. |
| 6,377,721 B1 | 4/2002 | Walt et al. |
| 6,387,331 B1 | 5/2002 | Hunter et al. |
| 6,436,632 B2 | 8/2002 | Schellenberger et al. |
| 6,441,973 B1 | 8/2002 | Walt et al. |
| 6,496,309 B1 | 12/2002 | Bliton et al. |
| 6,544,480 B1 | 4/2003 | Velghe et al. |
| 6,547,941 B2 | 4/2003 | Kopf et al. |
| 6,586,257 B1 | 7/2003 | Vuong |
| 6,716,629 B2 | 4/2004 | Hess et al. |
| 6,743,633 B1 | 6/2004 | Hunter |
| 6,794,127 B1 | 9/2004 | Lafferty et al. |
| 6,816,257 B2 | 11/2004 | Goix |
| 6,823,079 B1 | 11/2004 | Winterot et al. |
| 6,838,680 B2 | 1/2005 | Maher et al. |
| 6,866,824 B2 | 3/2005 | Lafferty et al. |
| 6,881,312 B2 | 4/2005 | Kopf et al. |
| 6,893,877 B2 | 5/2005 | Hunter et al. |
| 6,907,798 B2 | 6/2005 | Ganser et al. |
| 6,972,183 B1 | 12/2005 | Lafferty et al. |
| 6,977,723 B2 | 12/2005 | Lemmo et al. |
| 7,012,676 B2 | 3/2006 | Baer et al. |
| 7,019,827 B2 | 3/2006 | Laffert |
| 7,105,132 B2 | 9/2006 | Shumate et al. |
| 7,145,645 B2 | 12/2006 | Blumenfeld et al. |
| 7,221,455 B2 | 5/2007 | Chediak et al. |
| 7,272,510 B2 | 9/2007 | Hansen et al. |
| 7,282,329 B2 | 10/2007 | Manalis et al. |
| 7,289,217 B2 | 10/2007 | Boege et al. |
| 7,387,891 B2 | 6/2008 | Boege et al. |
| 7,403,280 B2 | 7/2008 | Beigel et al. |
| 7,452,507 B2 | 11/2008 | Renzi et al. |
| 7,547,556 B2 | 6/2009 | Hunter et al. |
| 7,666,360 B2 | 2/2010 | Schellenberger et al. |
| 7,666,630 B2 | 2/2010 | Yaver et al. |
| 7,738,945 B2 | 6/2010 | Fauver et al. |
| 7,807,108 B2 | 10/2010 | Fasulka |
| 7,907,259 B2 | 3/2011 | Sägmüller et al. |
| 7,933,004 B2 | 4/2011 | Sugita |
| 8,029,745 B2 | 10/2011 | Hunter et al. |
| 8,278,071 B2 | 10/2012 | Brown et al. |
| 8,309,035 B2 | 11/2012 | Chen et al. |
| 8,325,342 B2 | 12/2012 | Ali et al. |
| 8,338,092 B2 | 12/2012 | Hofmann et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,535,876 B2 | 9/2013 | Wesner |
| 8,551,698 B2 | 10/2013 | Brown et al. |
| 8,623,596 B2 | 1/2014 | Gandini et al. |
| 8,664,002 B2 | 3/2014 | Yeung |
| 8,673,218 B2 | 3/2014 | Jaffe et al. |
| 8,679,853 B2 | 3/2014 | Bhullar et al. |
| 8,722,357 B2 | 5/2014 | Baer et al. |
| 8,785,883 B2 | 7/2014 | Nakazawa et al. |
| 8,829,426 B2 | 9/2014 | Vertes et al. |
| 8,936,762 B2 | 1/2015 | Ehrlich et al. |
| 9,151,713 B2 | 10/2015 | Fan et al. |
| 9,314,764 B2 | 4/2016 | Hess et al. |
| 9,404,152 B2 | 8/2016 | Hasson et al. |
| 9,657,290 B2 | 5/2017 | Dimov et al. |
| 9,908,115 B2 | 3/2018 | Hobbs et al. |
| 10,087,408 B2 | 10/2018 | Hansen et al. |
| 10,227,583 B2 | 3/2019 | Cochran et al. |
| D844,471 S | 4/2019 | Stone |
| 11,085,039 B2 | 8/2021 | Cochran et al. |
| 11,156,626 B2 | 10/2021 | Chen |
| 11,473,081 B2 | 10/2022 | Cochran et al. |
| 12,024,705 B2 | 7/2024 | Cochran et al. |
| 2002/0045270 A1 | 4/2002 | Schurenberg et al. |
| 2002/0086322 A1 | 7/2002 | Yu |
| 2003/0003500 A1 | 1/2003 | Lafferty et al. |
| 2003/0044968 A1 | 3/2003 | Lafferty et al. |
| 2003/0092194 A1 | 5/2003 | Gambini |
| 2003/0096220 A1 | 5/2003 | Lafferty et al. |
| 2003/0106997 A1 | 6/2003 | Beecher et al. |
| 2003/0143580 A1 | 7/2003 | Straus et al. |
| 2003/0168458 A1 | 9/2003 | Lafferty et al. |
| 2003/0215798 A1 | 11/2003 | Short et al. |
| 2003/0231989 A1 | 12/2003 | Schleifer et al. |
| 2004/0005582 A1 | 1/2004 | Shipwash |
| 2004/0070763 A1 | 4/2004 | Yeung et al. |
| 2005/0057749 A1 | 3/2005 | Dietz et al. |
| 2005/0070005 A1 | 3/2005 | Keller et al. |
| 2005/0079105 A1 | 4/2005 | Hunter et al. |
| 2005/0287044 A1 | 12/2005 | Nataraj |
| 2006/0257013 A1 | 11/2006 | Ramm |
| 2006/0275847 A1 | 12/2006 | Goodyer |
| 2008/0062421 A1 | 3/2008 | Zhou |
| 2009/0042744 A1 | 2/2009 | Wagner et al. |
| 2009/0161100 A1 | 6/2009 | Minot et al. |
| 2010/0008892 A1 | 1/2010 | Shankar et al. |
| 2010/0252748 A1 | 10/2010 | Laitinen |
| 2010/0261159 A1 | 10/2010 | Hess et al. |
| 2011/0049385 A1 | 3/2011 | Laitinen |
| 2011/0124520 A1 | 5/2011 | Love et al. |
| 2011/0251105 A1 | 10/2011 | Walt et al. |
| 2011/0294208 A1 | 12/2011 | Allbritton et al. |
| 2012/0009671 A1 | 1/2012 | Hansen |
| 2012/0013726 A1 | 1/2012 | Thorburn |
| 2012/0015347 A1 | 1/2012 | Singhal |
| 2012/0021951 A1 | 1/2012 | Hess et al. |
| 2012/0064564 A1 | 3/2012 | Grassl |
| 2012/0094851 A1 | 4/2012 | Schellenberger et al. |
| 2012/0204906 A1 | 8/2012 | Bommarito |
| 2012/0244749 A1 | 9/2012 | Xiao |
| 2012/0321419 A1 | 12/2012 | Neeper |
| 2013/0019006 A1 | 1/2013 | Drittler |
| 2013/0071324 A1 | 3/2013 | Hino et al. |
| 2013/0190206 A1 | 7/2013 | Leonard et al. |
| 2013/0190212 A1 | 7/2013 | Handique |
| 2013/0196861 A1 | 8/2013 | Quake |
| 2013/0220528 A1 | 8/2013 | Peng et al. |
| 2013/0236905 A1 | 9/2013 | Marshall |
| 2013/0237443 A1 | 9/2013 | Knebel et al. |

(56) References Cited

U.S. PATENT DOCUMENTS

| | | |
|---|---|---|
| 2013/0260479 A1 | 10/2013 | Chou et al. |
| 2014/0011690 A1 | 1/2014 | Dimov et al. |
| 2014/0017700 A1 | 1/2014 | Fan et al. |
| 2014/0098214 A1 | 4/2014 | Schlaudraff et al. |
| 2014/0147884 A1 | 5/2014 | Schlaudraff et al. |
| 2014/0272984 A1 | 9/2014 | Hasson et al. |
| 2014/0329240 A1 | 11/2014 | Beer et al. |
| 2014/0329305 A1 | 11/2014 | Brown et al. |
| 2015/0051118 A1 | 2/2015 | Ghenciu et al. |
| 2015/0126412 A1 | 5/2015 | Hunter et al. |
| 2015/0323544 A1 | 11/2015 | Cambell et al. |
| 2015/0333471 A1 | 11/2015 | Chimmalgi et al. |
| 2016/0032404 A1 | 2/2016 | Schweighofer et al. |
| 2016/0202150 A1 | 7/2016 | Schlaudraff et al. |
| 2016/0215805 A1 | 7/2016 | Andou et al. |
| 2016/0244749 A1 | 8/2016 | Cochran et al. |
| 2016/0245805 A1 | 8/2016 | Baer et al. |
| 2016/0305936 A1 | 10/2016 | Leonard et al. |
| 2016/0332133 A1 | 11/2016 | Hess et al. |
| 2018/0163198 A1 | 6/2018 | Cochran et al. |
| 2018/0164294 A1 | 6/2018 | Cochran et al. |
| 2018/0230534 A1 | 8/2018 | Chen et al. |
| 2018/0299379 A1 | 10/2018 | Chen |
| 2018/0363059 A1 | 12/2018 | Quake et al. |
| 2019/0040461 A1* | 2/2019 | Ryu .................... C12Q 1/6874 |
| 2019/0094113 A1 | 3/2019 | Huang et al. |
| 2019/0217297 A1 | 7/2019 | Lavieu et al. |
| 2020/0150119 A1 | 5/2020 | Singhal et al. |
| 2020/0316593 A1 | 10/2020 | Chen et al. |
| 2022/0043017 A1 | 2/2022 | Chen et al. |
| 2022/0162594 A1 | 5/2022 | Hsien |
| 2023/0183676 A1 | 6/2023 | Cochran et al. |

FOREIGN PATENT DOCUMENTS

| | | |
|---|---|---|
| CN | 101529304 | 9/2009 |
| CN | 102348807 | 2/2012 |
| CN | 102445750 | 5/2012 |
| CN | 104656379 | 5/2015 |
| EP | 1 207 392 | 5/2002 |
| EP | 1 532 449 | 12/2010 |
| EP | 2 733 673 | 5/2014 |
| EP | 3 473 700 A1 | 4/2019 |
| JP | 11-245068 | 9/1999 |
| JP | 2003-319778 | 11/2003 |
| JP | 2004-093558 | 3/2004 |
| JP | 2006-101718 | 4/2006 |
| JP | 2007-535484 | 12/2007 |
| JP | 2008-200037 | 9/2008 |
| JP | 2010-112955 | 5/2010 |
| JP | 2010-281595 | 12/2010 |
| JP | 2016-163549 | 9/2016 |
| JP | 2018-017657 | 2/2018 |
| JP | 2020-533004 | 3/2019 |
| WO | WO 90/02326 | 3/1990 |
| WO | WO 98/020020 | 5/1998 |
| WO | WO 99/017094 | 4/1999 |
| WO | WO 00/031774 | 6/2000 |
| WO | WO 02/031203 | 4/2002 |
| WO | WO 02/072264 | 9/2002 |
| WO | WO 03/015922 | 2/2003 |
| WO | WO 03/072796 | 9/2003 |
| WO | WO 04/048571 | 6/2004 |
| WO | WO 05/040406 | 5/2005 |
| WO | WO 05/078438 | 8/2005 |
| WO | WO 05/121864 | 12/2005 |
| WO | WO 07/022026 | 2/2007 |
| WO | WO 07/035633 | 3/2007 |
| WO | WO 07/098148 | 8/2007 |
| WO | WO 08/034833 | 3/2008 |
| WO | WO 10/069913 | 6/2010 |
| WO | WO 11/049524 | 4/2011 |
| WO | WO 12/007537 | 1/2012 |
| WO | WO 13/008583 | 1/2013 |
| WO | WO 13/138767 | 3/2013 |
| WO | WO 13/163633 | 10/2013 |
| WO | WO 13/181288 | 12/2013 |
| WO | WO 14/008056 | 1/2014 |
| WO | WO 14/011985 | 1/2014 |
| WO | WO 14/070783 | 5/2014 |
| WO | WO 14/070873 | 5/2014 |
| WO | WO 14/074367 | 5/2014 |
| WO | WO 15/004321 | 1/2015 |
| WO | WO 15/017889 | 2/2015 |
| WO | WO 15/061462 | 4/2015 |
| WO | WO 15/061497 | 4/2015 |
| WO | WO 15/061506 | 4/2015 |
| WO | WO 15/095623 | 6/2015 |
| WO | WO 15/164846 | 10/2015 |
| WO | WO 15/164847 | 10/2015 |
| WO | WO 15/188171 | 12/2015 |
| WO | WO 15/104321 | 2/2016 |
| WO | WO 16/019341 | 2/2016 |
| WO | WO 16/077249 | 5/2016 |
| WO | WO 16/090295 | 6/2016 |
| WO | WO 16/094308 | 6/2016 |
| WO | WO 16/094333 | 6/2016 |
| WO | WO 16/094459 | 6/2016 |
| WO | WO 16/094507 | 6/2016 |
| WO | WO 16/094522 | 6/2016 |
| WO | WO 16/094715 | 6/2016 |
| WO | WO 16/115537 | 7/2016 |
| WO | WO 16/116455 | 7/2016 |
| WO | WO 16/118915 | 7/2016 |
| WO | WO 16/127107 | 8/2016 |
| WO | WO 16/134370 | 8/2016 |
| WO | WO 16/141343 | 9/2016 |
| WO | WO 16/172350 | 10/2016 |
| WO | WO 16/172454 | 10/2016 |
| WO | WO 16/172621 | 10/2016 |
| WO | WO 16/172623 | 10/2016 |
| WO | WO 17/059273 | 4/2017 |
| WO | WO 17/075295 | 5/2017 |
| WO | WO 17/091601 | 6/2017 |
| WO | WO 17/100347 | 6/2017 |
| WO | WO 17/117408 | 7/2017 |
| WO | WO 17/117521 | 7/2017 |
| WO | WO 17/117567 | 7/2017 |
| WO | WO 17/123978 | 7/2017 |
| WO | WO 17/161210 | 9/2017 |
| WO | WO 17/173105 | 10/2017 |
| WO | WO 17/176555 | 10/2017 |
| WO | WO 17/181135 | 10/2017 |
| WO | WO 17/205830 | 11/2017 |
| WO | WO 18/018017 | 1/2018 |
| WO | WO 18/053485 | 3/2018 |
| WO | WO 18/119043 | 3/2018 |
| WO | WO 18/064640 | 4/2018 |
| WO | WO 18/076024 | 4/2018 |
| WO | WO 18/102747 | 6/2018 |
| WO | WO 18/102748 | 6/2018 |
| WO | WO 18/102781 | 6/2018 |
| WO | WO 18/111765 | 6/2018 |
| WO | WO 18/126205 | 7/2018 |
| WO | WO 18/200872 | 11/2018 |
| WO | WO 19/015675 | 1/2019 |
| WO | WO 19/075476 | 4/2019 |
| WO | WO 19/133874 | 7/2019 |
| WO | WO 19/191459 | 10/2019 |
| WO | WO 19/232473 | 12/2019 |

OTHER PUBLICATIONS

Chen et al., Feb. 2016, High-throughput analysis and protein engineering using microcapillary arrays, Nature Chem. Biol. 12:76-81.

Chen, Jan. 2015, High-Throughput Analysis and Protein Engineering Using Microcapillary Arrays. A Dissertation Submitted to the Department of Bioengineering and the Committee on Graduate Studies of Stanford University, 190 pp.

Cherf, 2015, Applications of yeast surface display for protein engineering, Methods Mol. Biol., 13198:155-175.

(56) References Cited

OTHER PUBLICATIONS

Ching et al., Nov. 2, 2017, Chickens with humanized immunoglobulin genes generate antibodies with high affinity and broad epitope coverage to conserved targets, mAbs, 10(1):71-80.

Dobes et al., 2013, Laser-Based Directed Release of Array Elements for Efficient Collection into Targeted Microwells, Analyst, 138(3):831-838 with supplemental information.

Emmert-Buck et al., Nov. 8, 1996, Laser Capture Microdissection, Science, 274:998-1001.

Guild et al., 2011, Wheat germ cell-free expression system as a pathway to improve protein yield and solubility for the SSGCID pipeline, Acta Cryst., F67:1027-1031.

Kelkar et al., 2012, Bioluminescence based in vivo screening technologies, Curr. Opin. Pharmacol. 12:592-600.

Leica LMD6500, Leica LMD7000 Laser Microdissection Systems, product brochure, 2013, 16 pp.

Michelini et al., 2010, Cell-based assays: fuelling drug discovery, Anal. Bioanal. Chem. 398:227-238.

Quiagen, Cignal™ reporter assays, www.sabiosciences.com/reporterassay.php (Accessed Apr. 2017).

Quiagen, NFxB Reporter, http://www.sabiosciences.com/reporter_assay_product/HTML/CCS-013L-html (Accessed Apr. 2017).

Salazar et al., 2007, Micropallet Arrays for the Separation of Single, Adherent Cells, Anal. Chem. 79:682-687.

Sasaki, 2006, Structural basis for Fas6-Axl signalling, the EMBO Journal, 25(1):80-87.

Vandewoestyne et al., 2013, Laser capture microdissection: Should an ultraviolet or infrared laser be used? Analytical Biochemistry, 439:88-98.

Vogel et al. 2007, Principles of Laser Microdissection and Catapulting of Histologic Specimens and Live Cells, Methods in Cell Biology, 82:153-205.

WARD's Science, 2012, Beer-Lambert Law: Measuring Percent Transmittance of Solutions at Different Concentrations, Teacher's Guide, downloaded Mar. 28, 2020 from https://www.wardsci.com/www.wardsci.com/images/Beerlamb_Colorimeter.pdf, 21 pp.

International Search Report and Written Opinion mailed Feb. 1, 2021 in International Application No. PCT/US2020/059485.

* cited by examiner

_200_
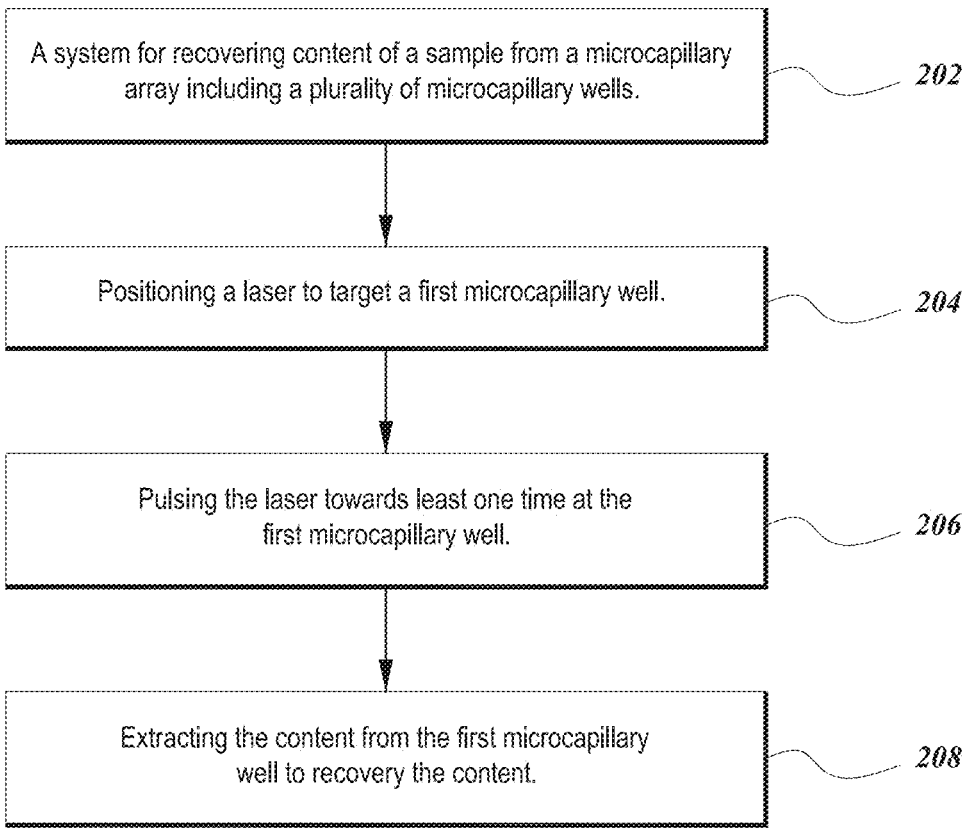
A system for recovering content of a sample from a microcapillary array including a plurality of microcapillary wells. — _202_
Positioning a laser to target a first microcapillary well. — _204_
Pulsing the laser towards least one time at the first microcapillary well. — _206_
Extracting the content from the first microcapillary well to recovery the content. — _208_
_FIG.2_

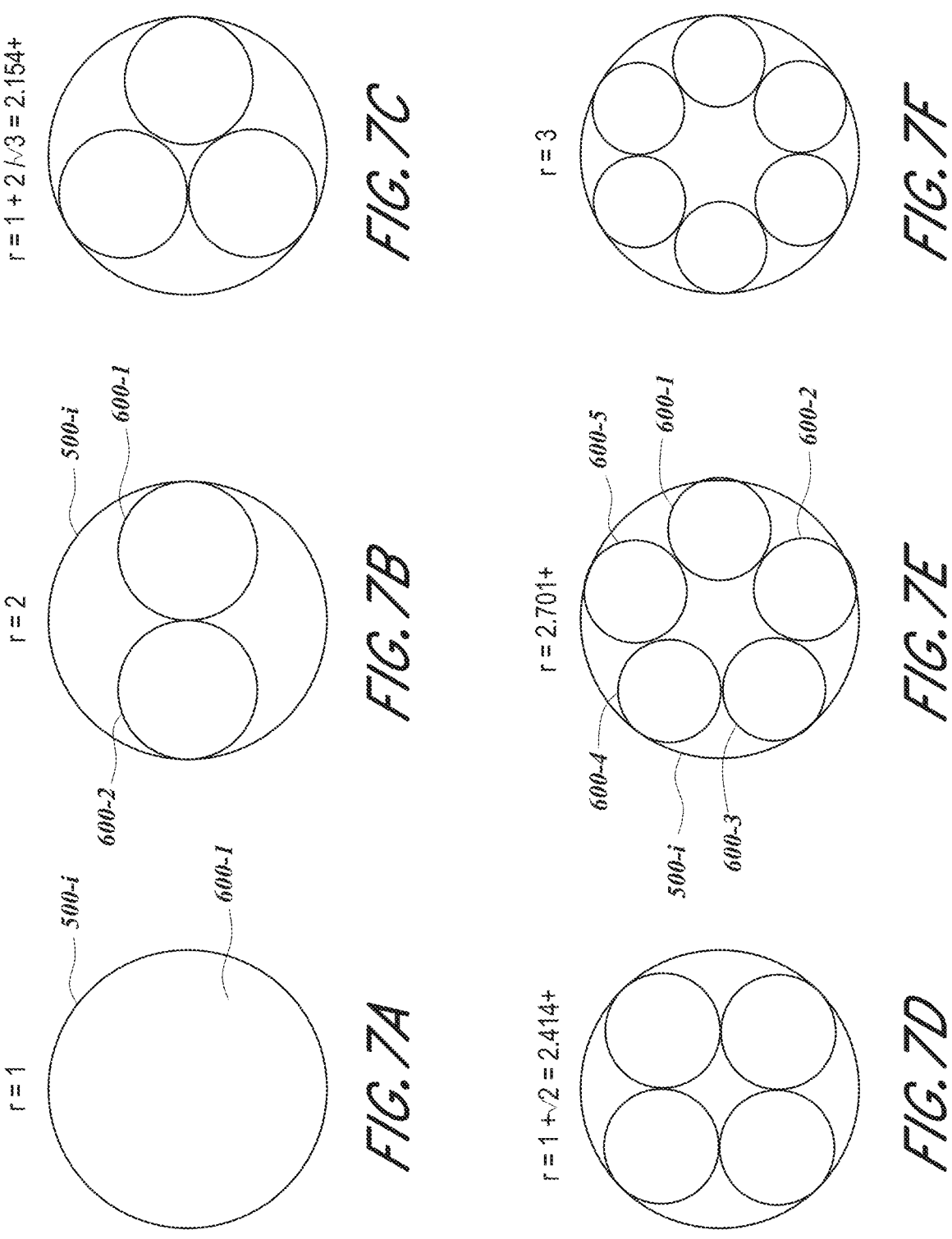

r = 3.613+ r = 4.029+ r = 3.304+ r = 3.923+ r = 3 r = 3.813+

Shape laser

Single point

Single Cell Sequencing Framework
_1200_

1302

1300

1300

1304

1300

134

1304

| Cells screened | 480,000 |
| --- | --- |
| % Ig Y secreting | 0.85% |
| % Antigen binding | 0.4% |
| % Specific of secreting | 47% |

• Extracted ~ 1000 hits above cutoff

Clonotype Clustering xP loration initial xP loration NGS

Ligand clone

APPARATUS AND METHODS FOR LASER-BASED SINGLE CELL RECOVERY FROM MICROCAPILLARY ARRAYS

BACKGROUND OF THE INVENTION

The analysis of biological samples, including the identification, characterization, and re-engineering of proteins, nucleic acids, carbohydrates, and other important biomolecules, has benefited greatly from the scaling up of sample numbers and the scaling down of sample sizes. For instance, the two-dimensional microarrays of biological materials, such as DNA microarrays, have enabled the development of high-throughput screening methods involving multiplexed approaches for processing samples and detecting results.

While such techniques provide analytical information about a particular sample, for instance the presence and potentially the amount of a particular biomolecule in a solution or the sequence of a particular nucleic acid or polypeptide, they typically do not allow for the recovery of a biological sample identified by the assay without inactivating or otherwise damaging the sample of interest. Moreover, methods that allow for retrieval are often based on the use of fluorescent or other tags.

Fluorescence and other methods that have been employed in the context of microarray assay technologies have their limitations. Cells and/or molecules must fluoresce so that they are capable of detection using such fluorescence methods. As such, these methods require labeling, adding extra time and effort for assay set-up and development. In the context of high throughput technologies, such extra time and effort can be significant, in particular when working with hundreds of thousands or even millions of samples.

There is therefore a continuing need to develop improved microscale screening and analysis methods, systems and devices with high throughput capabilities, and particularly methods and systems that enable analysis and recovery of samples without the need to pre-tag or pre-label the samples being analyzed. Such methods can find use in many applications, including enzyme engineering, ELISA assays, stability assays, and cell growth measurements.

While various groups have tried other methods for sample retrieval, there remains a need for more efficient and better methods (see, for instance, U.S. Patent Publication No.: 2017/0028376, U.S. Patent Publication No.: 2015/0072897, U.S. Patent Publication No.: 2017/0028376, and U.S. Pat. No. 8,105,554, all of which are incorporated by reference herein in their entireties).

Microcapillary arrays have recently been employed in approaches for high-throughput analysis and protein engineering with large numbers of biological samples, for instance in an approach that has been termed "microcapillary single-cell analysis and laser extraction" or "μSCALE." See, Chen et al. (2016) *Nature Chem. Biol.* 12:76-8. This approach relies on the spatial segregation of single cells within a microcapillary array, and thus enables repeated imaging, cell growth, and protein expression of the separate samples within each microcapillary of the microcapillary array. Accordingly, the technique enables massively parallel, quantitative biochemical and biophysical measurements on millions or multi-millions of samples within a microcapillary array, for instance, in the analysis of millions or multi-millions of protein variants expressed from yeast, bacteria, or other suitable cells distributed throughout the array. Advantageously, the approach has allowed the simultaneous time-resolved kinetic analysis of the multiplexed samples, as well as the sorting of those cells based on targeted phenotypic features.

The development of μSCALE methods and apparatus for the quantitative biochemical and biophysical analysis of populations of biological variants has also been reported in U.S. Patent Application Publication No.: 2016/0244749 A1, which is incorporated by reference herein in its entirety. Extraction of the contents of a desired microcapillary according to the μSCALE approach requires, however, the inclusion of a radiation-absorbing material in each sample and the directing of electromagnetic radiation from a pulsed laser into this material, thus adding complexity to the extraction methods. In addition, earlier methods of screening of biological variants in arrays of microcavities relied on the addition of microparticles to the arrayed samples to partially or completely inhibit the transmission of electromagnetic radiation into and out of the sample in order to minimize signal emitted from microcavities lacking a desired binding activity. See, U.S. Patent Application Publication No.: U.S. 2014/0011690 A1.

Furthermore, while such electromagnetic radiation transmitting methods typically allow for the recovery of a biological sample identified by the assay without inactivating or otherwise damaging the identified sample, such methods require that the cell be living after recovery. Once the live cell is retrieved from the microcapillary, the live cell is cultured for a prolonged period (e.g., days) and then sequenced, which further consumes significant time and effort. Accordingly, these methods require that the live cell be recovered in a wet environment (e.g., a well accommodating a lysis mix) to prevent decay of the cell.

The information disclosed in this background section is only for enhancement of understanding of the general background of the invention and should not be taken as an acknowledgement or any form of suggestion that this information forms the prior art already known to a person skilled in the art.

BRIEF SUMMARY OF THE INVENTION

Advantageously, the systems and methods detailed in the present disclosure address the shortcomings in the prior art detailed above. Systems and methods for laser-based single cell content recovery from a microcapillary array are provided. A laser is positioned to target a first microcapillary well in a plurality of microcapillary wells of the microcapillary array. The laser pulses at least one time towards the first microcapillary well. The content from the first microcapillary well is extracted, which recovers, or allows for the recovering of, the content of the first microcapillary well.

In one aspect, the present disclosure provides a method for recovering content of a sample from a microcapillary array comprising a plurality of microcapillary wells, wherein the method comprises: (A) positioning a laser to target a first microcapillary well in the plurality of microcapillary wells; (B) pulsing the laser at least one time towards the first microcapillary well; and (C) extracting the content from the first microcapillary well, thereby recovering the content of the first microcapillary well.

In some embodiments, the method further comprises, prior to the positioning the laser (A), identifying the first microcapillary well. In some embodiments, the pulsing the laser (B) further comprises pulsing the laser towards one or more subsections of the first microcapillary well. In some embodiments, the pulsing the laser (B) further comprises pulsing the laser more than one time and pulsing the laser in more than one subsection of the first microcapillary well.

In some embodiments, the content comprises one or more intact cells. In some embodiments, the one or more intact cells comprise mammalian cells, fungal cells, bacterial cells insect cells, or plant cells. In some embodiments, the one or more intact cells is no longer capable of cellular growth.

In some embodiments, the extracting and recovering (C) further comprise imaging the content during the recovery of the content.

In some embodiments, the positioning the laser (A) is performed using a laser guiding system. In some embodiments, the laser guiding system comprises the laser, a laser scanning assembly, a scan lens system, and a tube lens. In some embodiments, the laser guiding system is a galvanometer system. In some embodiments, the laser guiding system is a ScannerMAX Compact-506RE system. In some embodiments, the laser scanning assembly is a galvanometer mirror.

In some embodiments, a wavelength of light emitted from the laser is in a range of from 213 nanometers (nm) to 1380 nm. In some embodiments, the wavelength of light emitted from the laser is 355 nm, 514 nm, 532 nm, or 1064 nm.

In some embodiments, the microcapillary array is coupled to a sample stage. In some embodiments, the sample stage moves at a slower rate than the laser guiding system during the positioning of the laser (A).

In some embodiments, the laser pulses in a range of from 100 pulses per second to 1000 pulses per second, including for example 20,000 to 120,000 Hz and 10-1000 pulses total. In some embodiments, the laser pulses at 20,000 to 120,000 Hz and 10-1000 pulses total. In some embodiments, the laser pulses 500 pulses per second.

In some embodiments, the positioning the laser (A) further comprises imaging the content of the first microcapillary well using a laser guiding system.

In some embodiments, the laser pulses a plurality of subsections of the first microcapillary well in a range of from 2 subsections to 10 subsections. In some embodiments, the laser pulses 5 subsections of the first microcapillary well. In some embodiments, the laser pulses in a range of from 5 pulses to 15 pulses per subsection of the first microcapillary well. In some embodiments, the laser pulses 10 pulses per subsection of the first microcapillary well. In some embodiments, each laser pulse has a duration in a range of from 5 nanoseconds (ns) to 20 ns. In some embodiments, each laser pulse has a duration of 15 ns. In some embodiments, the laser pulses 5 subsections of the first microcapillary well, wherein the laser pulses 10 pulses per subsection of the first microcapillary well, and wherein each laser pulse has a duration of 15 ns.

In some embodiments, the laser guiding system further comprises one or more spatial light modulators to alter a shape of a beam emitted from the laser. In some embodiments, the laser guiding system further comprises a Digital Micromirror Device (DMD) to alter a shape of a beam emitted from the laser. In some embodiments, the content of the extracting and recovering (C) is disposed onto a collection slide.

In some embodiments, the collection slide comprises one or more collection slides containing a lysis buffer, wherein the lysis buffer is added to the one or more collection wells prior to the recovering the content (C). In some embodiments, the collection slide comprises one or more collection wells which do not contain a lysis buffer, wherein the lysis buffer is not added to the one or more collection wells prior to the recovering the content (C). In some embodiments, the method further comprises, following the extracting and the recovering (C), disposing the content onto a collection slide and freezing the collection slide. In some embodiments, the collection slide is subsequently thawed. In some embodiments, the thawed collection slide is subjected to treatment to denature RNA in the cell. In some embodiments, the thawed collection slide comprising the denatured RNA is subjected to RT-PCR amplification. In some embodiments, the RT-PCR amplification product is quantified. In some embodiments, the RT-PCR amplification product is sequenced.

In some embodiments, the method further comprises, following the extracting and the recovering (C), disposing the content onto a collection slide and transferring the content of the collection slide to a PCR plate and freezing the PCR plate. In some embodiments, the PCR plate is subsequently thawed. In some embodiments, the thawed the PCR plate is subjected to treatment to denature the RNA. In some embodiments, the thawed the PCR plate comprising the denatured RNA is subjected to RT-PCR amplification.

In some embodiments, the content comprises genetic material and wherein the sample comprises one or more intact cells with a desired phenotype. In some embodiments, the one or more cells are B cells. In some embodiments, the genetic material comprises an antibody sequence. In some embodiments, the antibody sequence comprises a heavy chain and a light chain. In some embodiments, the genetic material comprises mRNA.

In some embodiments, reverse transcription is performed on the mRNA. In some embodiments, the RT-PCR amplification of the heavy chain and the light chain is performed in separate reactions. In some embodiments, the RT-PCR amplification of the heavy chain and the light chain is performed in a single reaction vessel.

In some embodiments, the content comprises genetic material and wherein the sample comprises one or more intact cells with a desired phenotype, and wherein single-cell NGS sequencing is employed to determine the genetic phenotype. In some embodiments, the RT-PCR amplification further comprises one or more single cell specific DNA level barcodes. In some embodiments, the RT-PCR amplification further comprises one or more single cell specific DNA level barcodes, wherein the same barcode is added to the heavy chain and the light chain of an antibody sequence being amplified.

The methods and apparatuses of the present disclosure have other features and advantages which will be apparent from or are set forth in more detail in the accompanying drawings which are incorporated herein, and the following Detailed Description, which together serve to explain certain principles of the invention.

BRIEF DESCRIPTION OF THE DRAWINGS

FIG. 2 provides a flow chart of processes and features of a system for recovering a content of a sample, in accordance with an exemplary embodiment of the present disclosure.

FIG. 6A illustrates a view of positioning and pulsing of a laser towards an internal portion of each microcapillary well in a subset of microcapillary wells, in accordance with an exemplary embodiment of the present disclosure. FIG. 6B is an enlarged fragmentary view of FIG. 6A.

FIGS. 7A, 7B, 7C, 7D, 7E, 7F, 7G, 7H, 7I, 7J, 7K, and 7L collectively illustrate a variety of positioning configurations of a laser towards an internal portion of a microcapillary, in accordance with an exemplary embodiment of the present disclosure.

FIG. 8A illustrates a view of positioning and pulsing of a laser towards an a boundary portion of each microcapillary well in a subset of microcapillary wells, in accordance with an exemplary embodiment of the present disclosure. FIG. 8B is an enlarged fragmentary view of FIG. 8A.

FIG. 9A illustrates a progressive series of positioning and pulsing configurations of a laser and a boundary portion of a target, in accordance with an exemplary embodiment of the present disclosure. FIG. 9B is an enlarged fragmentary view of FIG. 9A.

Figure 1:
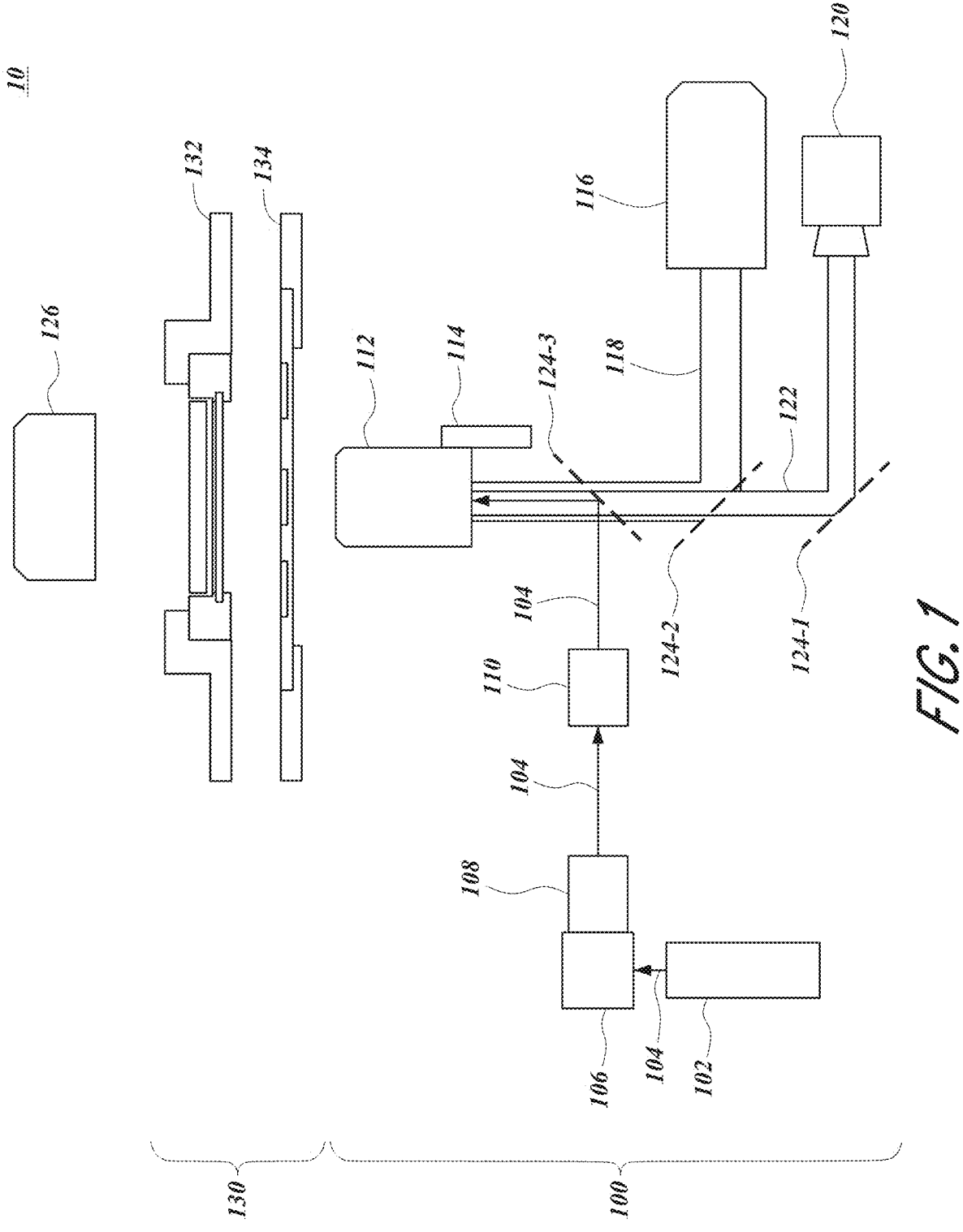
FIG. 1 illustrates an exemplary system topology for recovering a content of a sample from a microcapillary array, in accordance with an exemplary embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION OF THE INVENTION

The systems and methods of the present disclosure provide laser-based single cell recovery from microcapillary arrays for use in high-throughput analyses. The present disclosure meets an unmet need by providing systems and methods for laser-based single cell recovery from microcapillary arrays. The systems and methods of the present disclosure provide a positional laser that allows for a rapid recovery of a large number of samples from microcapillary arrays. The positional laser pulses a number of times towards the sample or a boundary of the sample and the microcapillary array to extract the sample to ensure optimal recovery of the sample. Furthermore, the positional laser transmits through an objective lens prior to illuminating the sample, allowing for simultaneous imaging and recovery of the sample. Additionally, the systems and methods of the present disclosure improve recovery of cells by allowing recovery an intact cell, and therefore for recovery and sequencing of a deceased cell into a dry environment, instead of requiring that the cell maintain cellular growth for extended culturing. In some aspects of the invention, the screening methods do not rely on the recovery of a live cell, and therefore do not rely on recovering in a wet environment, thus significantly reducing the consumed time and improving the efficiency of the screening techniques.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For instance, a first microcapillary well could be termed a second microcapillary well, and, similarly, a second microcapillary well could be termed a first microcapillary well, without departing from the scope of the present disclosure. The first microcapillary well and the second microcapillary well are both microcapillary wells, but they are not the same microcapillary well.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "$i^{th}$" denotation, the reference number refers to a generic component, set, or embodiment. For instance, a microcapillary well termed "microcapillary well i" refers to the $i^{th}$ microcapillary well in a plurality of microcapillary wells (e.g., a microcapillary well 500-$i$ in a plurality of microcapillary wells 500).

In some embodiments, microcapillary wells are long, through-holes with diameter small enough such that the surface tension holds a liquid in place. In some embodiments, the microcapillary wells have one entry from the top where the liquid is loaded. In some embodiments, the liquid in the microcapillary wells is held via surface tension with no bottom. In some embodiments, the opposite end of the through-hole is where the sample is recovered from.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designers specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Terms used in the claims and specification are defined as set forth below unless otherwise specified. In the case of direct conflict with a term used in a parent provisional patent application, the term used in the instant specification shall control. "Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified. e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g., insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "protein," as used herein, refers both to full-length proteins or polypeptide sequences and to fragments thereof. Such fragments may include fragments that retain a functional activity, such as, for instance, a binding activity. The terms "protein" and "polypeptide" are used interchangeably throughout the disclosure and include chains of amino acids covalently linked through peptide bonds, where each amino acid in the polypeptide may be referred to as an "amino acid residue." Use of the terms "protein" or"polypeptide" should not be considered limited to any particular length of polypeptide, e.g., any particular number of amino acid residues. The subject proteins may include proteins having non-peptidic modifications, such as post-translational modifications, including glycosylation, acetylation, phosphorylation, sulfation, or the like, or other chemical modifications, such as alkylation, acetylation, esterification, PEGylation, or the like. Additional modifications, such as the inclusion of non-natural amino acids within a polypeptide sequence or non-peptide bonds between amino acid residues should also be considered within the scope of the definition of the term "protein" or "polypeptide."

In some embodiments, the population of variant proteins is a population of proteins having minor variations, for instance a population of proteins where each protein has a slightly different amino acid sequence or a different post-translational modification. In some embodiments, the variant proteins can differ by 1, 2, 3, 4, 5, 6, 7, 8, 9, or 10 or more amino acids. In some embodiments, the variants differ by at least 1 amino acid. The screening assays can, therefore, identify variant protein sequences having desirable properties. Because the screens can be performed in such large numbers at microscopic scale, huge numbers of variant proteins can be assayed in relatively short times.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *Biol. Chem.* 260: 2605-2608, 1985; and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene. Polynucleotides used herein can be composed of any polyribonucleotide or polydeoxyribonucleotide, which can be unmodified RNA or DNA or modified RNA or DNA. For instance, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for instance, tritylated bases and unusual bases such as inosine. A variety of modifications can be made to DNA and RNA; thus, "polynucleotide" embraces chemically, enzymatically, or metabolically modified forms.

The term "barcode" as used herein is a label or tag used for identification purposes. In some embodiments, a barcode may be a sequence of nucleotides. In some embodiments, a barcode may be a single cell specific DNA level barcode. In some embodiments, one or more single cell specific DNA level barcodes may be used to identify heavy chains and/or light chains of an antibody sequence. In some embodiments, the same cell specific DNA level barcode is added to the heavy chain and the light chain of an antibody sequence being amplified.

"Microcavity" and variations thereof refer to a microcavity array comprising a plurality of microcavities, each microcavity comprising a sample component, including but not limited to proteins, polypeptides, nucleic acids, small molecules, and/or cells. The term microcavity includes microcapillaries and/or microwells.

Additionally, the terms "light guiding system," "laser guiding system," and "imaging guiding system" are used interchangeably herein unless expressly stated otherwise. Further, the terms "light" and "beam" are used interchangeably herein unless expressly stated otherwise.

The term, "lens," as used herein, includes a single lens or an assembly of lenses unless expressly stated otherwise.

Further, the term "target," as used herein, means a feature pulsed by a beam of a light source a number of times. A respective target can be subject to a single pulse or a plurality of pulses.

An aspect of the present disclosure is directed to providing a service for a recovery of a content of a sample from a microcapillary array. Systems and methods for recovering a content of a sample from a microcapillary array are provided. The microcapillary array includes a plurality of microcapillary wells, which are formed in a compact order. Each microcapillary well in a subset of the plurality of microcapillary wells accommodates a corresponding sample including a content for selective recovery. A laser positions to target a first microcapillary well of the plurality of microcapillary wells. The laser pulses at least one time towards the first microcapillary well, illuminating a portion of the first microcapillary well. The content from the first microcapillary well is extracted, recovering the content of the first microcapillary well.

FIG. 1 illustrates an exemplary topography of a system 10 for recovering a content of a sample. The system 10 includes a light guiding system 100 (e.g., a laser guiding system) that includes one or more light sources (e.g., a first light source 102 and a second light source 116). Each light source emits electromagnetic radiation (e.g., light) towards a designated target. The illuminating of a designated target provides imaging of the designated target and/or recovery of a content of the designated target depending on the respective light source. Accordingly, the guidance system 100 directs the light emitted from sources the light sources towards a designated target and controls one or more operations of the light source 102.

In some embodiments, the designated targeted includes a microcavity array 132 comprising a plurality of microcavities. Each microcavity in the microcavity array 132 accommodates a corresponding sample. Accordingly, the laser guiding system 100 illuminates a microcavity in the microcavity array 132 to recover the respective sample from the corresponding microcavity. In some embodiments, the microcavity array 132 is a component of a sample stage 130, which further includes a collection slide 134 for receiving the content of the sample once extracted.

Figures 4, 5:
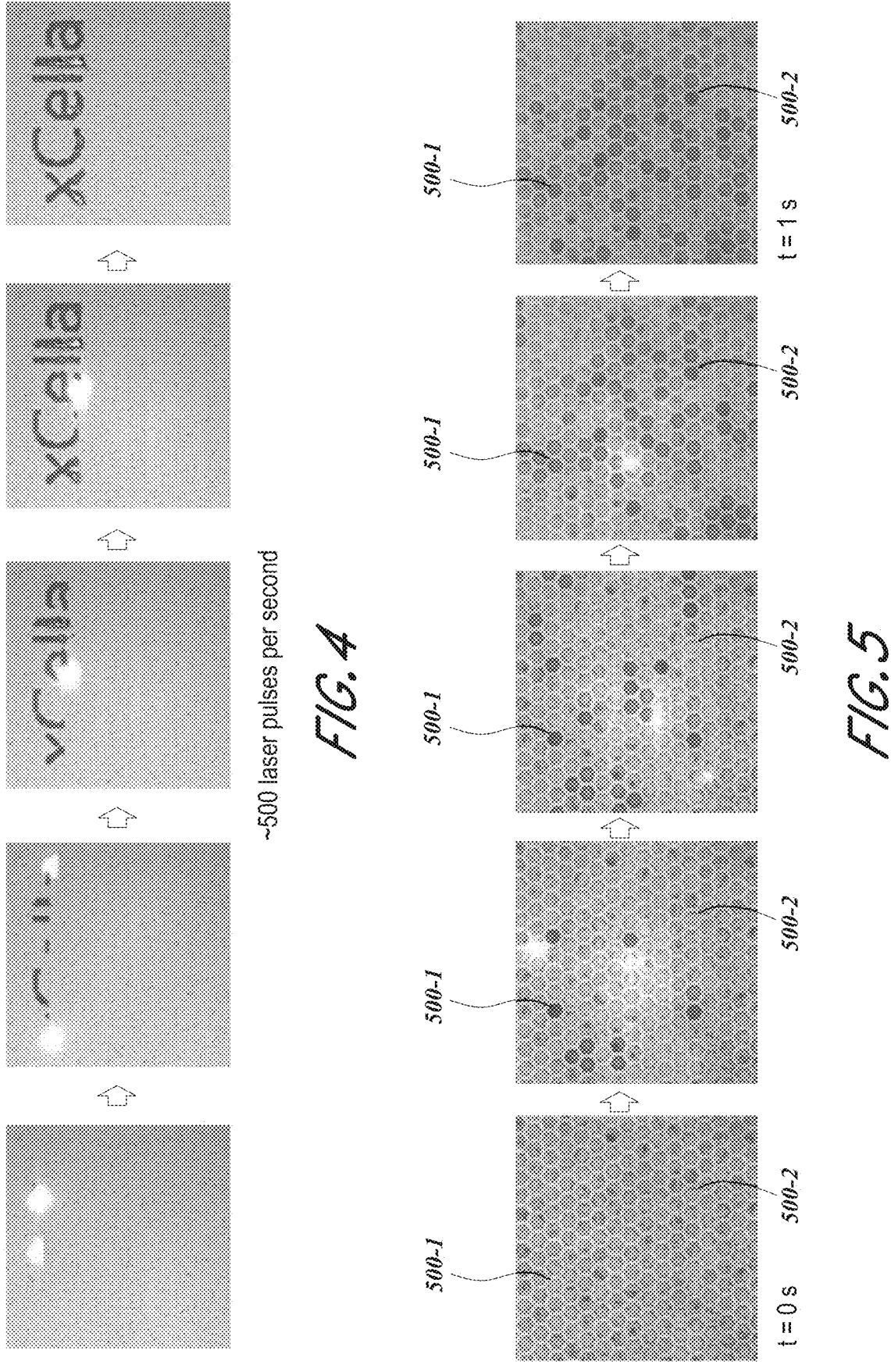
FIG. 4 illustrates a first view of a microcapillary array and positioning and pulsing of a laser towards the microcapillary array with respect to time, in accordance with an exemplary embodiment of the present disclosure.
FIG. 5 illustrates a second view of a microcapillary array and positioning and pulsing of a laser towards the micro-capillary array with respect to time, in accordance with an exemplary embodiment of the present disclosure.

In general, the microcavity array 132 includes an array of a plurality of chambers (e.g., microcapillaries 500 of FIG. 5). Each chamber accommodates a respective sample having various content. Further, each chamber of the microcavity array 132 allows for a transmission of light through the chamber. This transmission of light is enabled be either a shape of the chamber of and/or a material of the chamber, which will be described in more detail infra.

In some embodiments, the microcavity array 132 includes a microcapillary well array having a plurality of microcapillary wells (e.g., a first microcapillary well 500-1, a second microcapillary well 500-2, . . . an i$^{th}$ microcapillary well 500-i, etc.). Further, each microcapillary well 500 accommodates a respective sample (e.g., a first microcapillary well 500-1 accommodates a first sample 600-1, a second microcapillary well 500-2 accommodates a second sample 600-2, etc.). In some embodiments, the microcapillary array 132 includes a plurality of longitudinally fused capillaries 500, for instance fused silica capillaries. However, in some embodiments another suitable material is utilized for the microcapillary array 132. See, e.g., the arrays described U.S. application Ser. No. 62/433,210, filed Dec. 12, 2016; U.S. application Ser. No. 15/376,588, filed on Dec. 12, 2016; PCT International Patent Publication Nos.: WO 2012/007537 and WO 2014/008056, each of which is hereby incorporated by reference in its entirety.

In some embodiments, the microcapillary array 132 is fabricated, for instance, by a method including bundling millions or billions of silica capillaries and fusing them together through a thermal process. However, as described supra, in some embodiments, another suitable material is utilized for the microcapillary array 132. In some embodiments, the fusing process includes, for instance, heating a capillary single draw glass that is drawn under tension into a single clad fiber. A capillary multi draw single capillary is formed by bundling, heating, and drawing the single draw glass. Accordingly, a multi-draw multi-capillary is formed by additional bundling, heating, and drawing the multi-draw single capillary. A block assembly of drawn glass is further formed by stacking the multi-multi-draw multi-capillary in a press block. A block pressed block is formed through by treating the press block from the block assembly with heat and pressure. A block forming block is then formed by cutting the block pressing block at a predetermined length (e.g., 1 millimeter (mm)).

In some embodiments, the fabrication method further includes slicing (e.g., cutting) the silica capillaries. This slicing forms a glass microcapillary array 132 with a relatively high density of microcapillaries per unit area. In some embodiments, the microcapillary array 132 is sliced a height of approximately 1 mm. In some embodiments, the micro-capillary array 132 includes a plurality of microcapillary wells 500, each having a height in a range of from 1 microns (μm) to 25 mm, from 5 μm to 20 mm, from 5 μm to 15 mm, from 10 μm to 15 mm, or from 10 μm to 10 mm. However, the present disclosure is not limited thereto. For instance, in some embodiments, a height of the plurality of microcapillary wells 500 is contemplated that is shorter than or longer than the heights described above.

In some embodiments, each microcapillary well 500 in the microcapillary array 132 has a uniform height. This uniform height of the microcapillary array 132 allows for a surface (e.g., an upper surface and/or a lower surface) of each respective microcapillary well 500 to be coplanar, or substantially coplanar (e.g., coplanar within an acceptable tolerance known to one skilled in the art), with the plurality of microcapillary wells 500.

Such processes form a high-density microcapillary array 132 that is suitable for use in the present disclosure. In some embodiments, each microcapillary well 500 is formed in a cylindrical shape or a substantially cylindrical shape (e.g., a hemi-cylindrical shape, a shape of a polygon with n-sides of uniform length such as a hexagon, etc.) with an internal diameter. In such embodiments, an equivalent characteristic dimension including a hydraulic diameter of non-circular forms is used to determine an internal diameter of a substantially cylindrical microcapillary well 500. In some embodiments, an internal diameter of each microcapillary well 500 in the microcapillary array 132 is in a range of from 0.5 μm to 500 μm, from 1 μm to 500 μm, from 1 μm to 300 μm, from 25 μm to 250 μm, from 50 μm to 250 μm, from 50 μm to 200 μm, from 75 μm to 150 μm, from 75 μm to 125 μm, from 75 μm to 110 μm, from 80 μm to 110 μm, from 1

μm to 100 μm, from 1 μm to 75 μm, from 1 μm and 50 μm, from 5 μm to 50 μm, or from 1 μm to 10 μm. In some embodiments, the internal diameter of each respective microcapillary well 500 is 80 μm, 90 μm, 100 μm, 110 μm, or a combination thereof. In some embodiments, the internal diameter of each respective microcapillary well 500 is 1 μm, 5 μm, 10 μm, or a combination thereof. In some embodiments, the internal diameter of each respective microcapillary well 500 is constant. For instance, in some embodiments, the internal diameter of each respective microcapillary well 500 in the microcapillary array is 5 μm, 10 μm, or 100 μm. Furthermore, in some embodiments, the internal diameter of each respective microcapillary well 500 is constant. In some embodiments, the internal diameter transitions from a first diameter at a first end portion to a second diameter at a second end portion of the corresponding microcapillary well 500. In some embodiments, the internal diameter of the microcapillary well 500 includes a constant portion and an inconstant portion.

In some embodiments, each respective microcapillary well 500 includes an open region representing a lumen of the microcapillary well 500. In some embodiments, a proportion of one or more microcapillary wells 500 in the microcapillary array 132 that is open is in a range of from 40% to 95%, from 45% to 95%, from 50% to 90%, from 50% to 85%, from 55% to 80%, from 60% to 75%, from 65% to 70%, or from 66% to 68% of microcapillary wells 500. In some embodiments, the proportion of one or more microcapillary wells 500 in the microcapillary array 132 that is open is 67% of microcapillary wells 500. In some embodiments, the proportion of one or more microcapillary wells 500 in the microcapillary array 132 is that as provided by a commercially available microcapillary array 132, such as that of Hamamatsu Photonics K. K. (Japan).

In some embodiments, a collective open region including each open region of each microcapillary well 500 in the microcapillary array 132 includes 90% of an open area of the microcapillary array 132 so that, if the internal diameter of each microcapillary well 500 varies in a range of from 1 μm to 500 μm, a number of microcapillary wells 500 per centimeter squared (cm$^2$) of the microcapillary array 132 similarly varies in a range of from 460 microcapillary wells 500 to $1.1 \cdot 10^8$ microcapillary wells 500 or more. In some embodiments, the collective open area of the microcapillary array 132 includes approximately 67% of the open area, so that, if a pore size (e.g., open area) varies between 1 μm and 500 μm, a number of microcapillaries wells 500 per cm$^2$ of the microcapillary array 132 varies in a range of from approximately 340 to over 800,000 microcapillaries wells 500. In some embodiments, the number of microcapillary wells 500 per cm$^2$ of the microcapillary array 132 is in a range of from 500 microcapillary wells 500 to $1.10^7$ microcapillary wells 500.

In some embodiments, the microcapillary array 132 includes a surface area of 10 centimeters (cm) by 10 cm across (e.g., a surface area of an upper surface and/or lower surface of the microcapillary array 132). Further, each microcapillary well 500 in the microcapillary array 132 has an internal diameter of 5 μm and an open region of 66%. Accordingly, the microcapillary array 132 includes approximately $3.3 \cdot 10^8$ microcapillary wells 500 (e.g., a first microcapillary well 500-1, a second microcapillary well 500-2, . . ., a $(3.3 \cdot 10^8)$th microcapillary well 500-($3.3 \cdot 10^6$), etc.). In some microcapillary arrays, the open area of the array comprises up to 90% of the open area (OA), so that, when the pore diameter varies between 1 μm and 500 μm, the number of microcapillaries per cm of the array varies between approximately 460 and over 11 million. In some microcapillary arrays, the open area of the array comprises about 67% of the open area, so that, when the pore size varies between 1 μm and 500 μm, the number of microcapillaries per square cm of the array varies between approximately 340 and over 800,000. In some embodiments, the pore size is 1 μm, 5 μm, 10 μm 50 μm, 100 μm, 250 μm 350 or 500 μm. In some embodiments, the pore size is between 5 μm and 500 μm. In some embodiments, the pore size is between 10 μm and 450 μm. In some embodiments, the pore size is between 50 μm and 500 μm. In some embodiments, the pore size is between 100 μm and 500 μm. In some embodiments, the pore size is between 250 μm and 500 μm. In some embodiments, the pore size is between 350 μm and 500 μm. In some embodiments, the pore size is between 100 μm and 450 μm. In some embodiments, the pore size is between 250 μm and 450 μm. In some embodiments, the number of microcapillaries per square cm of the array is approximately 400; 500; 1000; 2,000; 3,000; 4,000; 5,000; 6.000; 7.000; 8,000; 9,000; 10,000; 20,000; 50,000, 100, 000; 200,000; 300,000; 400,000; 500,000; 600,000; 700, 000; or 800,000. In some embodiments, the number of microcapillaries per square cm of the array varies between approximately 500 and 800,000. In some embodiments, the number of microcapillaries per square cm of the array varies between approximately 1000 and 700,000. In some embodiments, the number of microcapillaries per square cm of the array varies between approximately 2000 and 600,000. In some embodiments, the number of microcapillaries per square cm of the array varies between approximately 10,000 and 800,000. In some embodiments, the number of microcapillaries per square cm of the array varies between approximately 10,000 and 700,000. In some embodiments, the number of microcapillaries per square cm of the array varies between approximately 50,000 and 800,000. In some embodiments, the number of microcapillaries per square cm of the array varies between approximately 50,000 and 700, 000. In some embodiments, the number of microcapillaries per square cm of the array varies between approximately 100,000 and 700,000. In some embodiments, the number of microcapillaries per square cm of the array varies between approximately 100,000 and 600,000. In some embodiments, the number of microcapillaries per square cm of the array varies between approximately 100,000 and 500,000. In some embodiments, the number of microcapillaries per square cm of the array varies between approximately 500, 000 and 800.000.

In some embodiments, the microcapillary array 132 is fabricated by bonding a plurality of silica capillaries (e.g., $1 \cdot 10^9$ capillaries) before fusing the silica capillaries together through a thermal fabrication process. The fused silica capillaries are sliced to a height of approximately greater than or equal to 0.5 mm, forming a glass microcapillary array 132 with a relatively high aspect ratio (e.g., greater than or equal to 10, greater than or equal to 25, . . . , greater than or equal to 10,000, etc.). The aspect ratio of a microcapillary array 132 is a ratio of a height with respect to an internal diameter of a microcapillary well 500 of the microcapillary array 500. In some embodiments, the aspect ratio of the microcapillary array 132 is in a range of from 0.002 (e.g., a microcapillary well 500 having a 1 μm height and a 500 μm internal diameter) to 50,000 (e.g., a microcapillary well 500 having a 25 mm height and a 0.5 μm internal diameter), from 2 to 50,000, from 5 to 50,000, from 5 to 25,000, from 10 to 25,000, from 10 to 15,000, from 20 to 15,000, or from 25 to 10,000. In some embodiments, the microcapillary array 132 is a commercially available microcapillary array, such as a microcapillary array available from Hamamatsu Photonics K. K. (Japan); Incom, Inc. (Massachusetts); Photonis Technologies, S.A.S. (France) Inc.; and others.

The microcapillary array 132 of the present disclosure is not limited to a specific number of microcapillary wells 500. In some embodiments, the number of microcapillary wells 500 of the microcapillary array 132 is determined in view of a size of a variant protein library to be screened. For instance, in some embodiments, the sample stage 130 of the system 10 can accommodate a number of different microcapillary arrays 132. In some embodiments, the microcapillary array 132 includes a number of wells in a range of from $1 \cdot 10^4$ microcapillary wells 500 to $5 \cdot 10^8$ microcapillary wells 500 or greater. However, the present disclosure is not limited thereto.

In some embodiments, the microcapillary array 132 has a thickness in a range of from 100 μm to 3,000 μm, from 150 μm to 2,500 μm, from 200 μm to 2,000 μm, from 500 μm to 2,500 μm, from 500 μm to 2,000 μm, from 750 μm to 1,750 μm, or from 1,000 μm to 1,500 μm. In some embodiments, the thickness of the microcapillary array 132 corresponds to a height of the microcapillary wells 500. For instance, if the height of the microcapillary wells 500 is 1 mm, the corresponding thickness of the microcapillary array 132 is approximately 1 mm (e.g., the thickness of the microcapillary array 132 is 1 mm excluding an additional thickness provided by a mounting mechanism of sample stage 130, such as a bracket).

In some embodiments, the microcavity array 132 has a thickness of 1.5 mm and each respective microcapillary well 500 has an internal diameter of 150 μm. In some embodiments, the microcavity array 132 has a thickness of 2 mm and each microcapillary well 500 has an internal diameter of 200 μm. In some embodiments, the microcavity array 132 has a thickness of 1 mm and each microcapillary well 500 has an internal diameter of 100 μm. In some embodiments, the microcavity array 132 has a thickness of 1 mm and each microcapillary well 500 has an internal diameter of 10 μm.

In some embodiments, a volume provided by each respective microcapillary well 500 (e.g., a volume of the sample for each respective microcapillary well 500) is in a range of nanoliters (nL) (e.g., 1 nL to 1,000 nL), in a range of picoliters (pL) (e.g., 1 pL to 1,000 pL), or in a range of femtoliters (fL) (e.g., 1 fL to 1,000 fL). In some embodiments, a volume of the sample accommodated by each respective microcapillary well 500 is in a range of from 1 nanoliters (nL) to 600 nL, from 5 nL to 500 nL, from 5 nL to 450 nL, from 5 nL to 400 nL, from 5 nL to 350 nL, from 5 nL to 300 nL, from 5 nL to 250 nL, from 5 nL to 200 nL, from 5 nL to 150 nL, from 5 nL to 100 nL, from 5 nL to 90 nL, from 5 nL to 80 nL, from 5 nL to 70 nL, from 5 nL to 60 nL, from 5 nL to 50 nL, from 5 nL to 40 nL, from 5 nL to 30 nL, from 5 nL to 20 nL, from 5 nL to 10 nL, from 5 nL to 8 nL, or from 7 nL to 8 nL. In some embodiments, the volume of the sample accommodated by each respective microcapillary well 500 is 7.8 nL. Furthermore, in some embodiments, the volume of the sample accommodated by each respective microcapillary well 500 is in a range of from 50 pL to 150 pL, from 65 pL to 110 pL, from 70 pL to 100 pL, from 70 pL to 90 pL, or from 70 pL to 80 pL. In some embodiments, the volume of the sample accommodated by each respective microcapillary well 500 is 78.5 nL. Additionally, in some embodiments, the volume of the sample accommodated by each respective microcapillary well 500 is in a range of from 100 fL to 1000 fL, from 150 fL to 1000 fL, from 200 fL to 1000 fL, from 250 fL to 1000 fL, from 300 fL to 1000 fL, from 350 fL to 1000 fL, from 350 fL to 950 fL, from 350 fL to 900 fL, from 400 fL to 900 fL, from 450 fL to 900 fL, from 500 fL to 950 fL, from 500 fL to 800 fL, from 100 fL to 250 fL, from 150 fL to 250 fL, from 150 fL to 200 fL, or from 125 fL to 175 fL. In some embodiments, the volume of the sample accommodated by each respective microcapillary well 500 is 157 fL.

In some embodiments, each microcapillary well 500 in the microcapillary array 132 further includes one or more agents disposed within the respective microcapillary well 500. The one or more agents improve a viability of the cellular expression system if a cellular expression assay is utilized with the systems and methods of the present disclosure. In some embodiments, the one or more agents prevent cell damage while recovering the content of a microcapillary well 500. For instance, in some embodiments, the recovery of the content includes emitting a pulse of light from a laser (e.g., laser 102 of FIG. 1), and the one or more agents prevent the sample (e.g., sample 602-*i* of FIG. 6B) from being damaged by the laser 102.

In some embodiments, the agent is methylcellulose (for instance in a range of from 0.001 wt % to 10 wt %), dextran (for instance in a range of from 0.5 wt % to 10 wt %), pluronic F-68 (for instance in a range of from 0.01 wt % to 10 wt %), polyethylene glycol ("PEG") (for instance in a range of from 0.01 wt % to 10 wt %), polyvinyl alcohol ("PVA") (for instance in a range of from 0.01 wt % to 10 wt %), or the like.

Alternatively, or in addition, in some embodiments, each microcapillary well 500 in the microcapillary array 132 further includes a growth additive, such as, for instance, 50% conditioned growth media, 25% standard growth media, or 25% serum. In some embodiments, the conditioned growth media is conditioned for approximately 24 hours. In some embodiments, the added agent includes insulin, transferrin, ethanolamine, selenium, an insulin-like growth factor, or a combination of thereof, or any of the agents recited above.

It should also be understood that the concentrations of each component of the screening assay within a microcapillary well 500 can be modulated as desired in an assay in order to achieve an optimal outcome. In particular, it may be desirable to modulate the concentration of proteins, polypeptides, nucleic acids, small molecules, and/or cells to achieve a desired level of association between these components. The level of association will also depend on a particular affinity between these components, wherein a higher affinity results in a higher level of association for a given concentration of the components, and a lower affinity results in a lower level of association of the components for a given concentration. Concentration of various components may likewise be modulated in order to achieve optimum levels of signal output, as would be understood by those of ordinary skill in the art.

In some embodiments, each microcapillary well 500 includes to an open planar surface at a first end portion and a second end portion of the microcapillary well 500. Further, in some embodiments, each corresponding open planar surface of the microcapillary array is coplanar to the corresponding open planar surfaces. In some embodiments, each microcapillary well 500 includes a through hole from a first planar surface to a second planar surface of the microcapillary well 500. However, the present disclosure is not limited thereto. In some embodiments, the microcapillary array 132 includes a solid substrate coupled an end portion (e.g., a surface or a portion of the surface) of the microcapillary array 132, which forms a closed end portion of one or more microcapillary wells 500 of the microcapillary array 132.

In some embodiments, a respective sample (e.g., sample 602-*i* of FIG. 6B) is accommodated in the microcapillary wells 500 by surface tension. For instance, in some embodiments the microcapillary wells 500 include an open surface at the first end portion and the second end portion of the microcapillary well 500, such that the sample 602 is accommodated by surface tension alone in microcapillary 500 with an expose first and second end portions. In some embodiments, the surface tension is the only force holding the sample in the respective microcapillary well 500. Accordingly, in such embodiments, pulsing of a beam of a laser (e.g., beam 104 of laser 102 of FIG. 1) towards the sample 602 disrupts the surface tension of the respective microcapillary well 500 and extracting the sample 602.

Libraries that can be screened according to the present disclosure include any library including a plurality of molecules as well as mixtures and/or combinations thereof. In some embodiments, the library includes samples including biological material. In some embodiments, the library includes samples including a plurality of one or more molecules and/or cells as well as mixtures and/or combinations thereof. In some embodiments, the library includes samples including a plurality of one or more proteins, polypeptides, nucleic acids, small molecules, dyes, and/or cells as well as mixtures and/or combinations thereof. In some embodiments, the small molecules include any molecule. In some embodiments, the molecules include proteins, polypeptides, nucleic acids, small molecules, and/or dyes as well as mixtures and/or combinations thereof. In some embodiments, the library includes samples including biological materials that include polypeptides, nucleic acids, small molecules, and/or cells as well as mixtures and/or combinations thereof. In some embodiments, the library includes a plurality of samples. In some embodiments, the samples include biological materials that include polypeptides, nucleic acids, small molecules, dyes, and/or cells as well as mixtures and/or combinations thereof. In some embodiments, the samples contain a least one molecule and/or cell to be screened. In some embodiments, the samples contain a least one to ten molecules and/or cells to be screened, as well as mixtures and/or combinations thereof. In some embodiments, the samples contain a plurality of molecules and/or cells to be screened, as well as mixtures and/or combinations thereof. In some embodiments, the molecule to be screened is termed a target molecule. In some embodiments, the cell to be screened is termed a target cell.

The microcapillary array 132 provided herein allows for screening of a library including proteins, polypeptides, nucleic acid, small molecules, dyes, and/or cells, as well as mixtures and/or combinations thereof. In some embodiments, the target molecule to be screened is a protein, polypeptide, nucleic acid, small molecule, dye, carbohydrate, lipid, or a combination of thereof. In some embodiments, the proteins and/or polypeptides are selected from the group consisting of enzymes, ligands, and receptors. For instance, in some embodiments, the target molecule includes a lipid-modified or glycosylated protein. In some embodiments, the target molecule includes a native protein.

As described above, in embodiments, each microcapillary well 500 in the microcapillary array 132 provided by the present disclosure accommodates a respective sample having a content that differs from the content of a sample of another microcapillary well 500 in the microcapillary array

132 (e.g., a first microcapillary well 500-1 accommodates a first sample 600-1, a second microcapillary well 500-2 accommodates a second sample 600-2, a third microcapillary well 500-3 accommodates a third sample 600-3, etc.). Similarly, in embodiments, one or more microcapillary wells 500 in the microcapillary array 132 provided by the present disclosure accommodates a respective sample having a content that differs from the content of a sample of another microcapillary well 500 in the microcapillary array 132 (e.g., a first microcapillary well 500-1 accommodates a first sample 600-1, a second microcapillary well 500-2 accommodates a second sample 600-2, a third microcapillary well 500-3 accommodates the first sample 600-1, etc.). In some embodiments, the content of the sample includes proteins, polypeptides, nucleic acids, small molecules, dyes, and/or cells (i.e., target molecules and/or target cells), as well as mixtures and/or combinations thereof. In some embodiments, the library for screening includes a variant protein, a variant polypeptide, a variant nucleic acid, a variant small molecule, a variant dye, and/or one or more variant cells exhibiting distinguishing characteristics. In some embodiments, the variant protein, the variant polypeptide, the variant nucleic acid, the variant small molecule, the variant dye, and/or the one or more variant cells exhibit distinguishing characteristics. These exhibited distinguishing characteristics allow each microcapillary well 500 to include a respective sample including a different target molecule and/or target cell from a corresponding sample accommodated by each of the other microcapillary wells 500 within the microcapillary array 132. In some embodiments, one or more microcapillary wells 500 within the microcapillary array 132 includes a respective sample including the same target molecule and/or target cell as another sample accommodated by at least one other microcapillary well 130 within the microcapillary array 132 (e.g., a respective sample is at least duplicated for comparison).

In some embodiments, the proteins and/or polypeptides in the library to be screened in the microcapillary array 132 include one or more variant proteins and/or polypeptides. Variant proteins include proteins and polypeptides that are distinguishable from one another based on at least one characteristic or feature. In some embodiments, the variant proteins and/or polypeptides exhibit different amino acid sequences, exhibit different amino acid sequence lengths, are produced/generated by different methods, exhibit different activities, exhibit different chemical modifications, exhibit different post-translational modifications, or a combination thereof. In some embodiments, the variant protein includes a population of variant proteins and/or polypeptides that is being subjected to screening and analysis utilizing the microcapillary array 132 of the present disclosure. In some embodiments, the population of variant proteins and/or polypeptides include any population of proteins that is suitably distributable within the microcapillary array 132.

In some embodiments, the nucleic acids in the library to be screened in the microcavity array includes one or more variant nucleic acids. Variant nucleic acids include nucleic acids that are distinguishable from one another based on at least one characteristic or feature. In some embodiments, the variant nucleic acids include different nucleotide sequences, different nucleotide sequence lengths, different methylation patterns, different chemical modifications, are produced/generated by different methods, exhibit other distinguishing modifications, or a combination thereof. In some embodiments, the nucleic acid is of a population of variant nucleic acids that is being subjected to screening and analysis utilizing the microcapillary array 132 of the present disclosure. In some embodiments, the population of variant nucleic acids includes any population of nucleic acids that is suitably distributable within the microcapillary array 132.

In some embodiments, the small molecules in the library to be screened in the microcapillary array 132 includes variant and/or different small molecules. Variant small molecules include small molecules that are distinguishable from one another based on at least one characteristic or feature. In some embodiments, the variant small molecules include different structures, have been produced/generated by different methods, have different chemical modifications, exhibit other distinguishing different features, or a combination thereof. In some embodiments, the small molecules are derivatives of one another. In some embodiments, the small molecule is of a population of small molecules that is being subjected to screening and analysis utilizing the microcapillary array 132 of the present disclosure. In some embodiments, the population of small molecules includes any population of small molecules that is suitably distributable within the microcapillary array 132.

In some embodiments, the cells in the library to be screened in the microcavity array include variant cells and/or cells of varying types. Variant cells include cells that are distinguishable from one another based on at least one characteristic or feature. In some embodiments, the cells are derived from different samples, are derived from different patients, are derived from different diseases, have different chemical modifications, have been genetically modified, or a combination thereof. In some embodiments, the cells include eukaryotic and/or prokaryotic cells. In some embodiments, the cells include mammalian cells (e.g., human cells, rodent cells such as mice cells and rat cells, avian cells such as chicken cells, etc.), bacterial cells, fungal cells including yeast cells, insect cells, or plant cells. In some embodiments, the mammalian cells include blood cells, lymphocyte cells, splenocyte cells, lymph node cells, bone marrow cells, or a combination thereof. In some embodiments, the cell is of a population of cells that is being subjected to screening and analysis utilizing the microcapillary array 132 of the present disclosure. In some embodiments, the population of cells include any population of cells that is suitably distributable within the microcapillary array 132.

In some embodiments, the population of proteins, polypeptides, nucleic acids, and/or cells is distributed in the microcapillary array 132 allowing each microcapillary well 500 to accommodate a small number of different variant proteins, variant polypeptides, variant nucleic acid, and/or cells. In some embodiments, each respective microcapillary well 500 includes a single different variant protein, variant polypeptide, variant nucleic acid, and/or cell. In some embodiments, each respective microcapillary well 500 includes a single different variant protein. In some embodiments, each respective microcapillary well 500 includes a single different variant polypeptide. In some embodiments, each respective microcapillary well 500 includes a single different variant nucleic acid per microcavity. In some embodiments, each respective microcapillary well 500 includes a single different cell per microcavity. The population of variant proteins, variant polypeptides, variant nucleic acid, and/or cells is chosen in combination with other components within the sample.

In some embodiments, each microcapillary well 500 in the microcapillary array 132 includes different variant proteins, variant polypeptides, variant nucleic acids, and/or cells from the population of variant proteins in a range of from 0 different variants to 10 different variants, from 0 different variants to 7 different variants, from 0 different variants to 5 different variants, from 0 different variants to 4 different variants, from 0 different variants to 3 different variants, from 0 different variants to 2 different variants, or from 0 different variants to 1 different variant.

Accordingly, in some embodiments, the variant proteins include soluble proteins, for instance, soluble proteins that are secreted by a cellular expression system. Exemplary soluble variant proteins include antibodies and antibody fragments, alternative protein scaffolds such as disulfide-bonded peptide scaffolds, extracellular domains of cell-surface receptor proteins, receptor ligands such as G-protein coupled receptor ligands, other peptide hormones, lectins, and the like. In some embodiments, the variant proteins screened using the systems and methods of the present disclosure do not need to be covalently attached to the cell or virus that expresses the respective variant protein in order to be identified following a screening assay. Recovery of the content of a respective microcapillary well 500, followed by propagation of the cell or virus clone responsible for expression of the desired variant protein, enables the identification and characterization of the respective variant protein. Unlike screening assays in which a variant protein is displayed by fusion of the protein to a molecule on a surface of a cell or virus particle, the variant proteins identified in present disclosure need not be altered in any way either before or after their identification. The observed activities of the variant proteins in the screens are thus more likely to represent the actual activities of those proteins in their subsequent applications. Not needing to alter variant proteins or polypeptides prior to screening also allows for more efficient screening, saving costs and time for library preparation.

In some embodiments, the variant proteins to be screened include membrane-associated proteins, for instance, proteins typically associated with a surface of a cell or a viral particle in an expression system. In some embodiments, screening of cell-associated variant proteins is desirable if the variant protein and its target molecule mediate interactions between two cells within a biological tissue. In some embodiments, the ability to screen cell-associated variant proteins is desirable in screening for interactions with traditionally "non-druggable" protein targets such as, for instance, G-protein coupled receptors or ion channels. Again, not needing to alter variant proteins or polypeptides prior to screening also allows for more efficient screening, which saves resources during library preparation.

In some embodiments, the variant nucleic acids to be screened include any nucleic acid or polynucleotide, including nucleic acids or polynucleotides that bind to or interact with proteins. Again, not needing to alter the nucleic acids or polynucleotides prior to screening also allows for more efficient screening, saving costs and time for library preparation.

In some embodiments, the protein to be screened is an antibody, antibody fragment, such as an Fc, or an antibody fusion, including, for instance, Fc fusions. In some embodiments, the antibody or antibody fragment can be labeled.

In some embodiments, the method employs the use of an antibody to bind to the target molecule to be screened. In some embodiments, the antibody is a labeled primary antibody or a labeled secondary antibody as is used to bind to the target molecules. A primary antibody is typically considered to be an antibody that binds directly to an antigen of interest, whereas a secondary antibody is typically considered to be an antibody that binds to a constant region on a primary antibody for purposes of labeling the primary antibody. Accordingly, secondary antibodies are frequently labeled with fluorophores or other detectable labels or are labeled with enzymes that are capable of generating detectable signals. The secondary antibodies are generally specific for a primary antibody from a different species. For instance, in some embodiments, a goat or other animal species is used to generate secondary antibodies against a mouse, chicken, rabbit, or nearly any primary antibody other than an antibody from that animal species, as is understood by those of ordinary skill in the art. In some embodiments, the labeled antibody is a primary or secondary antibody. In some embodiments, the labeled antibody is a fluorescent antibody or an enzyme-linked antibody.

As would be understood by those of ordinary skill in the art, if a fluorescent antibody, for example, is used in the systems and methods of the present disclosure, a signal emitted by any excess reporter element remaining free in solution (i.e., either not bound to a variant protein or bound to a variant protein that is not bound to a target molecule) within a respective microcapillary well 500 should not be so high that it overwhelms a signal of reporter elements associated with a target molecule via a variant protein (see, e.g., the unassociated fluorescent antibodies). Such background signals can be minimized, however, by limiting the concentration of labeled antibody or other reporter element within the microcapillary solution. In addition, in some embodiments, if signals from the screening methods are measured using a fluorescent microscope, a microscope is configured to image a relatively narrow depth of field bracketing the location of the target molecules (e.g., a lower end portion of the microcapillary wells 500 if target cells have settled at the lower end portion by gravitational sedimentation) to minimize a background signal from reporter elements not associated with the target molecule.

In some embodiments, a number of microcapillary wells 500 within the microcapillary array 132 is determined in view of a size of the library to be screened. In some embodiments, a size of the library is in a range of from $1 \cdot 10^4$ to $5 \cdot 10^8$ proteins, polypeptides, nucleic acids, small molecules, and/or cells, as well as mixtures and/or combinations thereof. However, the present disclosure is not limited thereto.

It would be understood by one of skill in the art that each respective microcapillary well 500 will typically include a plurality of copies of the same protein, polypeptide, nucleic acid, small molecule, and/or cell, depending on a source and an expression level of the particular protein, polypeptide, nucleic acid, small molecule, and/or cell, as well as mixtures and/or combinations thereof. In some embodiments, each respective microcapillary well 500 includes a number of molecules of a particular protein, polypeptide, nucleic acid, small molecule, and/or cell in a range of from $5 \cdot 10^2$ to $1 \cdot 10^{10}$, depending on how the protein, polypeptide, nucleic acid, small molecule, and/or cell is delivered to or expressed within the respective microcapillary well 500 as well as mixtures and/or combinations thereof. In some embodiments, a number of types of proteins, polypeptides, nucleic acids, small molecules, and/or cells in a sample accommodated by a respective microcapillary well 500 is in a range of from 1 type to 10 types, from 1 type to 5 types, or from 1 type to 4 types.

The population of proteins, polypeptides, nucleic acids, and/or small molecules, as well as mixtures and/or combinations thereof, is typically generated using a genetic library in a biological expression system, for example, in an in vitro (e.g., cell-free) expression system or in an in vivo or cellular expression system. In some embodiments, the population of proteins, polypeptides, nucleic acids, and/or small molecules, as well as mixtures and/or combinations thereof, is generated via any known synthesis methods. Exemplary cellular expression systems include, for example, animal systems (e.g., mammalian systems), fungal systems (e.g., yeast systems), bacterial systems, insect systems, or plant systems. In some embodiments, the expression system is a mammalian system or a yeast system. The expression system, whether cellular or cell-free, typically includes a library of genetic material encoding the population of variant proteins. Cellular expression systems offer the advantage that cells with a desirable phenotype, for example, cells that express a particular variant protein of interest, such as a variant protein capable of associating with an immobilized target molecule with high affinity, can be grown and multiplied, thus facilitating and simplifying the identification and characterization of the proteins of interest expressed by the cells.

Genetic libraries encoding large populations of proteins, polypeptides, nucleic acids, and/or small molecules, as well as mixtures and/or combinations thereof, are well known in the art of bioengineering. Such libraries are often utilized in systems relying on the process of directed evolution to identify proteins with advantageous properties, such as high-affinity binding to target molecules, stability, high expression, or particular spectroscopic, e.g., fluorescence, or enzymatic activities. Often the libraries include genetic fusions with sequences from the host expression system, for example, fragments of proteins directing subcellular localization, where the expressed population of variant fusion proteins are directed by the targeting fragment to a particular location of the cell or virus particle for purposes of activity screening of the variant protein population. Large numbers of variant proteins, polypeptides, nucleic acids, small molecules, and/or cells (e.g., $10^6$ variants, $10^8$ variants, $10^{10}$ variants, $10^{12}$ variants, or even more variants), as well as mixtures and/or combinations thereof, can be generated using routine bioengineering techniques, as is well known in the art. In some embodiments, the library is purchased from a commercial source.

However, the present disclosure is not limited thereto. In some embodiments, the sample includes inorganic material or a combination of organic and inorganic material, such as an environmental source (e.g., soil, water, vegetation, etc.). In some embodiments, the microscope stage mounting allows for recovery of said microcapillary array contents with a laser. In some embodiments, the recovered contents comprise cells. In some embodiments, the recovered contents include live cells and/or deceased (e.g., dead) cells. In some embodiments, the recovered cells are further analyzed for the presence of one or more nucleic acids. In some embodiments, the recovered cells are further analyzed for the presence of one or more amino acids.

Now that details of a microcapillary array 132 and a microcapillary well 500 have been disclosed, details regarding a light guiding system 100 of the sampling system 10, in accordance with an embodiment of the present disclosure, are disclosed.

Referring to FIG. 1, the system 10 includes a light guiding system 100 that facilitates recovery and/or imaging of the content of the microcapillary array 132. The system 10 further includes a sampling stage 130 that accommodates the microcapillary array 132 and, in some embodiments, aids in facilitating recovery and/or imaging of the content of the microcapillary array 132.

In some embodiments, the system 10 includes one or more computers (e.g., a computer system) having a memory and processor. The memory stores one or more programs for execution by the one or more processors. The one or more programs singularly or collectively include instructions for utilizing the light guiding system 100 and/or the sampling stage 130. In some embodiments, the one or more instructions include positioning instructions for a light source of the light guiding system 100 (e.g., positioning instructions for positioning a component on an optical assembly of the light guiding system 100, etc.), operational instructions for the light source (e.g., activation and deactivation instructions, intensity instructions, pulse parameter instructions, and the like), and similar instructions with respect to the sample stage 130 (e.g., positioning instructions).

The guiding system 100 includes one or more light sources that direct electromagnetic radiation towards a target to illuminate a portion of the target (e.g., the microcapillary array 132). In some embodiments, a first subset of the one or more light sources facilities extracting and recovering the content from a sample of a microcapillary well 500 (e.g., cell 604-1 of 500-$i$ of FIG. 6B), while a second subset of the one or more light sources facilitates imaging of the sample. In some embodiments, the first and second subset of light sources operate in concert, allowing for real time imagining of the microcapillary array 132 during recovery of the sample. In some embodiments, the light guiding system 100 includes a corresponding guiding system for one or more light dependent components of the system 10. For instance, in some embodiments the guiding system 100 includes a laser guiding system 100 for use at least in operating a laser 102 and positioning a beam 104 of the laser 102. In some embodiments, the guiding system 100 includes an imaging guiding system for use at least in operating one or more cameras 120.

Due to a relatively small size of diameter for each microcapillary well 500 (e.g., a diameter of less than 1 cm), the light guiding system 100 utilizes a focused beam of light 104 to accurately and precisely target a respective microcapillary well 500 within the microcapillary array 132 during the recovery of the content of the microcapillary array 132. Accordingly, in some embodiments, the light source includes a laser 102 that emits a coherent beam 104 of electromagnetic radiation. In some embodiments, the laser 102 is a laser diode. In some embodiments, the laser 102 is a continuous wave laser or, preferably, a pulse laser.

The laser 102 includes a pulse period defining a frequency of pulses (e.g., 1 pulse per second yields 1 Hertz (Hz), etc.). In some embodiments, the pulse period of the laser is in a range of from 1 Hz to 60,000 Hz (e.g., 60 kilo-Hertz (kHz)), from 100 Hz to 60 kHz, from 500 Hz to 60 kHz, from 500 Hz to 50 kHz, from 500 Hz to 40 kHz, from 1 kHz to 40 kHz, from 1 kHz to 30 kHz, from 1 kHz to 27.5 kHz, from 1 kHz to 25 kHz, from 1.5 kHz to 25 kHz, from 2 kHz to 25 kHz, from 1 kHz to 20 kHz, from 2 kHz to 20 kHz, from 2.5 kHz to 20 kHz, from 5 kHz to 25 kHz, from 5 kHz to 20 kHz, from 10 kHz to 40 kHz, or from 15 kHz to 25 kHz. In some embodiments, the pulse period of the laser 102 is 20 kHz.

In some embodiments, the laser 102 emits light 104 in the ultra-violet spectrum (e.g., a UV laser) or in the visible spectrum (e.g., a visible spectrum laser). In some embodiments, the beam 104 emitted from the laser 102 is a range of from 213 nanometers (nm) to 1380 nm. In some embodiments, the beam 104 emitted from the laser 102 is selected from the group consisting of 355 nm, 375 nm, 404 nm, 405 nm, 406 nm, 450 nm, 462 nm, 473 nm, 488 nm, 514 nm, 520 nm, 532 nm, 633 nm, 635 nm, 637 nm, 638 nm, 639 nm, 640 nm, 642 nm, 650 nm, 658 nm, 660 nm, 670 nm, 685 nm, 690 nm, and 1064 nm. In some embodiments, the wavelength of the beam 104 is selected in accordance with a target of laser 102.

In some embodiments, the laser 102 is a commercially available laser. In some embodiments, the commercial laser 102 includes, for example, those available from Thorlabs (see, for example, those listed on the World Wide Web at Thorlabs.com/newgrouppage9.cfm?objectgroup_id=7); Spectra-Physics (see, for example, those listed on the Word Wide Web at spectra-physics.com/products/q-switched-lasers/explorer-one); and/or Integrated Optics (see, for example, those listed at integratedoptics.com/products/nanosecond-lasers).

In some embodiments, the guiding system 100 of system 10 includes an objective lens 112 that intercepts a beam from the one or more light sources (e.g., beam 104 of the laser 102, beam 118 of a fluorescent light source 116, etc.), and/or a field of view of the one or more cameras 120. For instance, as illustrated in FIG. 1, in some embodiments the objective lens 112 interposes between the sample stage 130 and the one or more light sources, allowing the objective lens 112 to collect light from each of the one or more light sources. In some embodiments, the objective lens 112 is based on a modified microscope. In some embodiments, the microscope provides front-end image collection and optical zoom with high light collection efficiency. In some embodiments, the objective lens 10 provides an optical magnification in a range of from 1 to 100 optical magnification, from 2 to 100 optical magnification, from 4 to 100 optical magnification, from 4 to 80 optical magnification, or from 4 to 40 optical magnification. In some embodiments, the optical magnification of the objective lens 112 is 10.

In some embodiments, the objective lens 112 is fixed, such that the sample stage 130 positions relative to the objective lens 112. In some embodiments, the objective lens 112 is coupled to a motor 114 that allows for a positioning of the objective lens 112. In some embodiments, the motor 114 provides one degree of freedom to the objection lens 112. In some embodiments, the one degree of freedom provided by the motor 114 is different than a degree of freedom provided by a galvanometer system 106 (e.g., the galvanometer system 106 provides two translational degrees of freedom in X and Y axes and the motor 114 provides one translational degree of freedom in a Z axis for redirecting the beam 104). Accordingly, in some embodiments, the objective lens 112 is fixed on a plane parallel to a corresponding plane of the sample stage 130 such that the beam 104, after passing through the objective lens 112, is directed towards the microcapillary array 132 with an angle of incidence of 0 degrees (°), or approximately about 0°. This limited angle of incidence allows the objective lens 112 to provide a single field of view of the microcapillary array 132. In such embodiments, the single field of view allows the laser 102 to position from a first target to a second target without having to refocus the beam 104 or otherwise adjust the laser 102. Accordingly, in some embodiments, the guiding system 100 and the sample stage 130 traverse relative to one another, such that the movement of the sample stage 130 provides a new field of view for the objective lens. Furthermore, this configuration with the limited angle of incidence allows for imaging of the microcapillary array during (e.g., simultaneous to) an extracting of the content from a microcapillary well 500.

In some embodiments, the one or more light sources includes a fluorescent light source 116 that emits a corresponding beam 118 of light. In some embodiments, the fluorescent light source 116 emits a beam 118 of light in the UV wavelength spectrum (e.g., in a range of from 10 nm to 400 nm).

In some embodiments, the one or more light sources include a bright-field light source 126. The bright-field light source 126 is disposed at an opposing end portion of the microcapillary array 132 with respect to the fluorescent light source 116, such that the microcapillary array 132 interposes between the beam 118 of the fluorescent light source 116 and the bright-field light source 126. In some embodiments, emitted light from the one or more light sources is directed from the sample of a designated microcapillary well 500 to a detection unit (e.g., the bright-field light source 126).

In some embodiments, the laser guiding system 100 and the microcapillary array 132 are each disposed at a fixed position, such that an optical train (e.g., a laser scanning assembly) facilitates guiding the beam 104 of the laser towards a designated target (e.g., a first microcapillary well 500-1, a portion of the first microcapillary well 500-1, etc.). For instance, in some embodiments, the sampling stage 130 accommodates the microcapillary 132 in a fixed position, preventing the microcapillary array 132 from moving positions during recovery and/or imaging of the content and physical disruption to the content of the microcapillary array 132.

In some embodiments, the sampling stage 130 provides the microcapillary array 132 with a plurality of degrees of freedom, yielding the microcapillary array 132 the ability to position (e.g., traverse and/or rotate) accordingly. For instance, in some embodiments, the microcapillary array 132 positions with six degrees of freedom, allowing the microcapillary array 132 to traverse and/or rotate about three orthogonal axis (e.g., traverse about a three-dimensional Cartesian coordinate system and rotate with variable pitch, roll, and yaw). In some embodiments, the microcapillary array 132 positions with only one or more translational degree of freedom. Accordingly, in embodiments in which the content of the microcapillary array 130 is fluid the content remains at a substantially horizontal free surface (e.g., within an acceptable tolerance, excluding a meniscus, etc.). This includes embodiments in comprising substantially fluid content (e.g., a heterogeneous mixture including solid and fluid matter) or the like.

Figure 3:
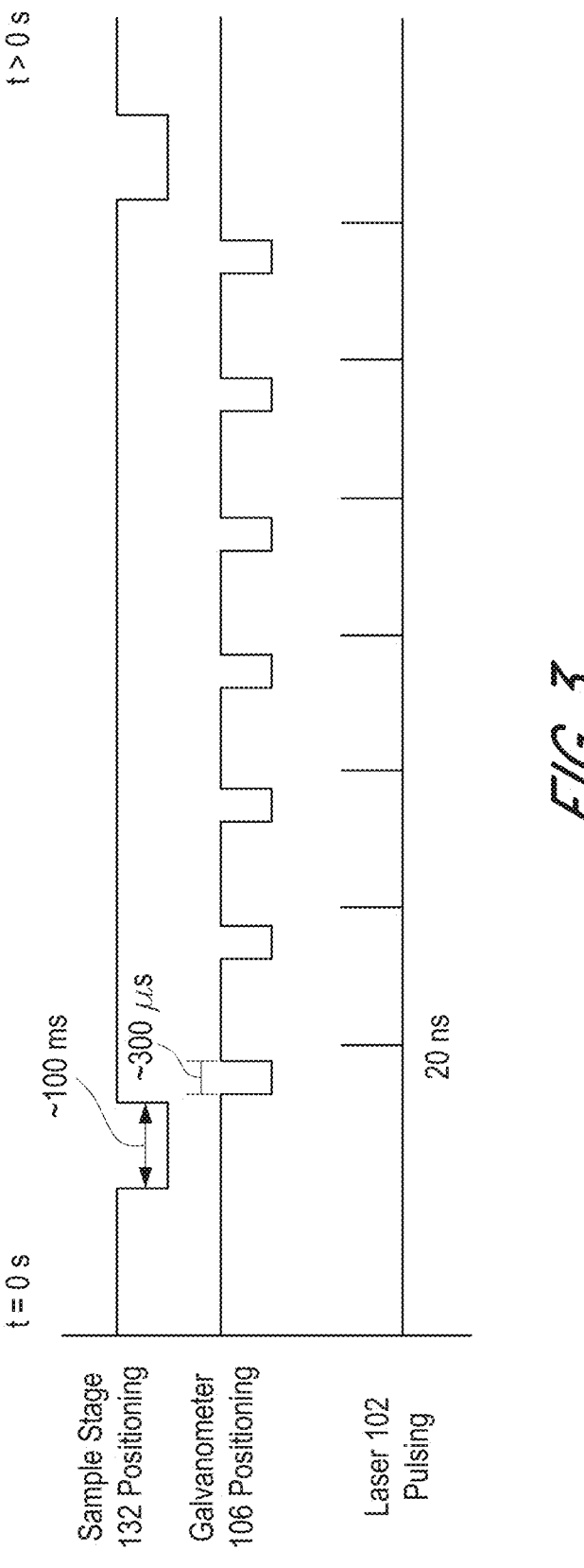
FIG. 3 illustrates a chart of various coordinating components of a system with respect to time, in accordance with an exemplary embodiment of the present disclosure.

Referring to FIG. 3, in some embodiments, the laser guiding system 100 and the microcapillary array 132 are movable relative to one another (e.g., both or one of the laser guiding system 100 and the microcapillary array 132 is movable), allowing the beam 104 of the laser 102 to be guided in accordance with a relative movement of the system 10. In some embodiments, the guiding of the beam 104 is provided by at least a galvanometer 106. In some embodiments, the positioning of two or more components of the system 10 is conducted sequentially, such that a first component of the system 10 is positioned from a first position to a second position. Once the first component positions to the second position, the system 10 conducts positioning of a second component of the section from a third position to a fourth position. For instance, in some embodiments, the system 10 conducts a first positioning of the sampling stage 130 and, upon completion of the first positioning, conducts a second positioning of the beam 104 (e.g., via the galvanometer 106). Furthermore, in some embodiments, the system 10 conducts a pulsing of the laser 102 upon completion of the second positioning of the beam 104. In some embodiments, conducting the positioning of the sample stage prior to the positioning of the beam 104 allows for a greater period of time to elapse between the completion of the positioning of the sample stage 130 and the pulsing of the laser 102, further allowing the content of the microcapillary array 132 to settle from a transient disturbance occurring during the positioning of the sample stage 130.

In some embodiments, the system 10 conducts a plurality of instances of the positioning of the beam 104 and, upon completion of the positioning of the beam 104, pulsing of the laser 102 towards the designated target before repositioning the sample stage 130. In some embodiments, the plurality of instances of the positioning and the pulsing towards the designated target is in a range of from 1 instance to 100 instances, from 1 instance to 50 instances, from 1 instance to 25, from 1 instance to 15 instances, from 2 instances to 15 instances, from 1 instance to 12 instances, from 2 instances to 12 instances, from 1 instance to 10 instances, from 2 instances to 10 instances, or from 4 instances to 10 instances. In some embodiments, the plurality of instances of the positioning and the pulsing towards the designated target is 5 instances.

Moreover, in some embodiments, pulsing of the beam 104 towards a designated target (e.g., a first microcapillary well 500-1) more than once is desirable for recovery of the content of the designated target. Accordingly, upon completion of the positioning of the sample stage 130, the system 10 conducts two or more instances of the positioning of the beam 104 and the pulsing of the laser 102 towards the designated target. For instance, a coordination of the positioning of the sample stage 130, the positioning of the galvanometer 106, and the pulsing of the laser 102 is depicted in FIG. 3. In the coordination of FIG. 3, the system 10 conducts a first positioning of the sample stage 130 from a respective initial position to a first position, which occurs over a period of time of approximately 100 milliseconds (ms). Upon completion of the first positioning of the sample stage 132, the system 10 conducts a first positioning of the beam 104 through the galvanometer 106 from a respective initial position towards the first position. This first positioning of the beam 104, and depending on a distance between respective positions, each respective instance of the positioning of the beam 104, occurs over a period of time of approximately 300 microseconds (μs). Accordingly, upon completion of the first positioning of the beam 104, the system 10 conducts a first pulsing of the laser 102 towards the first position. Each respective instance of the pulsing the laser 102, occurs over a period of time of approximately 20 nanoseconds (ns) (e.g., a pulse duration of 20 ns). In some embodiments the pulse duration is in a range of from 0.001 ns to 100 ns, from 0.01 ns to 100 ns, from 0.1 ns to 100 ns, from less than 1 ns to 50 ns, from 1 ns to 50 ns, from 0.1 ns to 30 ns, from 0.1 ns to 25 ns, from 0.1 ns to 20 ns, or from 5 ns to 20 ns. Upon completion of the first pulsing of the laser 102 towards the first position, the system 10 conducts a second positioning of the beam 104 from the first position to a second position. Upon completion of the second positioning of the beam 104, the system 10 conducts a second pulsing of the laser 102 towards the second position. This series of the positioning the beam 104 and the pulsing the laser 102 is repeated for a predetermined number of instances for one or more positioning of the sample stage 130. In the coordination of FIG. 3, the positioning the beam 104 and the pulsing the laser 102 is repeated seven times for the first position of the sample stage 130. However, the present disclosure is not limited thereto. In some embodiments, prior upon completion of each instant of the pulsing of the laser 102, the system 10 is at least partially at rest (e.g., not actively recovering the content from the microcapillary array 132) for a period of time. In some embodiments, this period of time of partial rest is utilized to conduct imaging of the microcapillary array 132.

In some embodiments, the positioning of the sample stage 130 is conducted at a rate in a range of from 0.1 millimeters per second (mm/s) to 20 mm/s, from 0.1 mm/s to 10 mm/s, from 0.5 mm/s to 20 mm/s, from 0.5 mm/s to 15 mm/s, from 1 mm/s to 15 mm/s, from 1 mm/s to 10 mm/s, from 5 mm/s to 15 mm/s, from 5 mm/s to 10 mm/s, from 7.5 mm/s to 15 mm/s, from or 7.5 mm/s to 12.5 mm/s, or from 9 mm/s to 11 mm/s. In some embodiments, the positioning of the sample stage 130 is conducted at a rate of less than 10 mm/s or at a rate of less than or equal to 10 mm/s. Furthermore, in some embodiments, the positioning of the beam 104 (e.g., through the guiding system 100) is conducted at a rate in a range of from 10 mm/s to 1,500 mm/s, 50 mm/s to 1,500 mm/s, from 50 mm/s to 1,250 mm/s, from 100 mm/s to 1,250 mm/s, or from 100 mm/s to 1,000 mm/s. Moreover, in some embodiments, the rate of the positioning of the sample stage 130 is conducted at a slower rate than the beam 104, and therefore at a slower rate than the guiding system 100. For instance, in some embodiments, a ratio of the rate of positioning of the sample stage 130 to the rate of positioning of the beam 104 via the guiding system 100 is in a range of from 1:5 to 1:1,500, from 1:5 to 1:1,250, from 1:10 to 1:1,500, from 1:10 to 1,250, or from 1:10 to 1:1,000. In some embodiments, the above-described rates of the positioning are an instantaneous velocity or an average velocity taken over a period of time of the positioning.

In some embodiments, the laser guiding system 100 includes an optical train, also referred to as an optical assembly. The optical train includes an arrangement of one or more light manipulation instruments including one or more lenses (e.g., an objective lens 112 of FIG. 1), one or more filters, one or more mirrors (e.g., mirror 124-1 of FIG. 1), or a combination thereof employed as part of the imaging system to, at least, guide the beam 104 emitted from the laser 102. In some embodiments, a position and/or an angle of each lens and/or mirror 124 is adjusted to guide a beam of a light source (e.g., the beam 104 of the laser 104) towards a designated target, and such adjustments would be within the level of skill of one of skill in the art to adjust as needed for an imaging system.

In some embodiments, the optical train for the instrument is based on a modified microscope. In some embodiments, the microscope provides front-end image collection and optical zoom with high light collection efficiency. In some embodiments, the imaging system includes a color camera. In some embodiments, the imaging system includes a black and white camera. In some embodiments, the imaging system includes a color camera and a black and white camera. In some embodiments, the optical train is coupled to one or more emission filters optimized for a particular wavelength, fluorophore, and/or ratiometric dye (e.g., mirror 124-1, mirror 124-2, and mirror 124-3 of FIG. 1).

In some embodiments, the optical train of the laser guiding system 100 includes a laser scanning assembly that further guides the beam 104 emitted from the laser 102 towards a designated targeted, such as a first microcapillary well 500-1. In some embodiments, the laser scanning assembly includes one or more mirrors 124 that redirect a course of the beam 104 of the laser 102. For instance, in some embodiments the one or more mirrors 124 includes a first mirror 124-1, a second mirror 124-2, and a third mirror 124-3. In some embodiments, one or more of the mirrors 124 is a filter. Further, in some embodiments, one or more of the mirrors 124 is a dichroic. For instance, in some embodiments, one or more of the mirrors 124 includes a material such as a dichroic mirror or a dichroic filter. In some embodiments, the first mirror 124-1 is a reflective mirror configured to manipulate a field of view for one or more cameras 120 and direct light (e.g., beam 122) towards the one or more cameras 120. In some embodiments, the second mirror 124-2 includes a dichroic material that interacts with the electromagnetic radiation 118 emitted from the light source 116. For instance, in some embodiments, the second mirror 124-2 is an epifluorescence dichroic mirror. Accordingly, in some embodiments, the second mirror 124-2 allows for a transmission (e.g., beam 122) of a first spectrum of light (e.g., visible light) captured by the one or more cameras 120 to pass through the second mirror 124-2, while reflecting transmission (e.g., beam 118) of a second spectrum of light (e.g., UV light) emitted from a fluorescent light source 116. Furthermore, in some embodiments, the third mirror 124-3 is a laser dichroic mirror. Accordingly, in some embodiments, the third mirror 124-3 allows for a transmission (e.g., beam 104) of a fourth spectrum of light while reflecting transmission (e.g., beam 104) of a third spectrum of light (e.g., a wavelength of the beam 104). In some embodiments, the fourth spectrum of light includes the first and second spectrums of light.

In some embodiments, the optical assembly of the light guiding system 100 includes a galvanometer system 106. The galvanometer system 106 includes a plurality of mirrors and a galvanometer that controls a positioning of each mirror in the plurality of mirrors of the galvanometer system 106. The beam 104 of the laser 102 is directed towards the galvanometer system 106, and in accordance with a positioning of the plurality of mirrors, the beam 1004 is directed towards either the microcapillary array 132 or a further component of the optical assembly of the guiding system 100 (e.g., a scan lens 108, a tube lens 110, dichroic mirror 124-3, an objective lens 112, or a combination thereof). In some embodiments, the galvanometer system 106 allows for a positioning of the beam 104 in one or more axis, such as two axis (e.g., an X-axis and a Y-axis of a Cartesian system). In some embodiments, the galvanometer system 106 includes a commercial galvanometer system, such as a Thorlabs Galvo Mirror Assembly (GVSM002) or a ScannerMAX Compact-506RE. As described supra, in some embodiments the galvanometer system 106 positions at a rate substantially greater than a positioning rate of the sample stage 130 (e.g., by a factor of 10, a factor of 100, a factor of 1000, etc.), allowing the laser 102 to emit pulses of the beam 104 towards different targets in rapid succession with a high level of accuracy and precision.

Referring to FIG. 4, in some embodiments, the galvanometer system 106 directs the beam 104 emitted from the laser 102 towards one or more defined coordinates at high speed. For instance, in some embodiments a surface of the microcapillary array 132 (e.g., a surface facing the objective lens 112), is mapped to a coordinate system. Accordingly, in some embodiments, the computer system of the system 10 provides instructions to the galvanometer system 106 to direct the beam 104 towards a predetermined series of defined coordinates. In some embodiments, the laser 102 pulses the beam 104 an equal number of pulses at each defined coordinate in the series. As illustrated in FIG. 4, the beam 104 of the laser 102 interacts with the surface of an object with each pulse of the laser. In the illustrated embodiment of FIG. 4, the beam 104 first targets a first coordinate and progresses through the series of defined coordinates in a linear manner over a period of time, which is occurs at a rate of approximately 500 beam pulses 104 per second.

However, the present disclosure is not limited thereto. In some embodiments, instead of progressing by rows or columns of coordinates, the galvanometer system 106 directs the beam 104 emitted from the laser 102 towards a target in a cluster of targets. In some embodiments, the laser pulses in a range of from 100 pulses per second to 1000 pulses per second. In some embodiments, the laser pulses about 100 pulses per second, about 200 pulses per second, about 300 pulses per second, about 400 pulses per second, about 500 pulses per second, about 600 pulses per second, about 700 pulses per second, about 800 pulses per second, about 900 pulses per second, or about 1000 pulses per second. In some embodiments, the laser pulses 500 pulses per second.

Referring to FIG. 5, in some embodiments, the galvanometer system 106 directs the beam 104 emitted from the laser 102 towards one or more microcapillary wells 500 (e.g., identified targets) at high speed. For instance, in some embodiments each respective defined coordinate represents a position of a corresponding microcapillary well 500 in the microcapillary array 132. Accordingly, the galvanometer system 106 directs the beam 104 towards a first defined coordinate of a first microcapillary well 500-1, and the laser 102 is pulsed to extract the content from the first microcapillary well 500-1. The galvanometer system 106 further directs the beam 104 towards a second defined coordinate of a second microcapillary well 500-2, and the laser 102 is pulsed to extract the content from the second microcapillary well 500-1. In FIG. 5, a relatively darker colored microcapillary well 500 depicts a previously targeted microcapillary well 50.

In some embodiments, the galvanometer system 106 directs the beam 104 emitted from the laser 102 towards a plurality of specific parts of each microcapillary well 500 to improve sample recovery. For instance, referring to FIGS. 6A and 6B, in some embodiments, the galvanometer system 106 directs the beam 104 emitted from the laser 102 towards a plurality of internal portions of the microcapillary well 500. In the Figures, targets 600 (e.g., target 600-1 of FIG. 6B, target 600-5 of FIG. 7E, etc.) represents a plurality of pulses of the laser 102 towards the designated target pulsed by the laser 102 (e.g., each of target 600-1 through target 600-5 represent approximately 10 to 20 individual pulses of the laser 102 at a rate of 20 kHz per target 600).

Figure 6A:
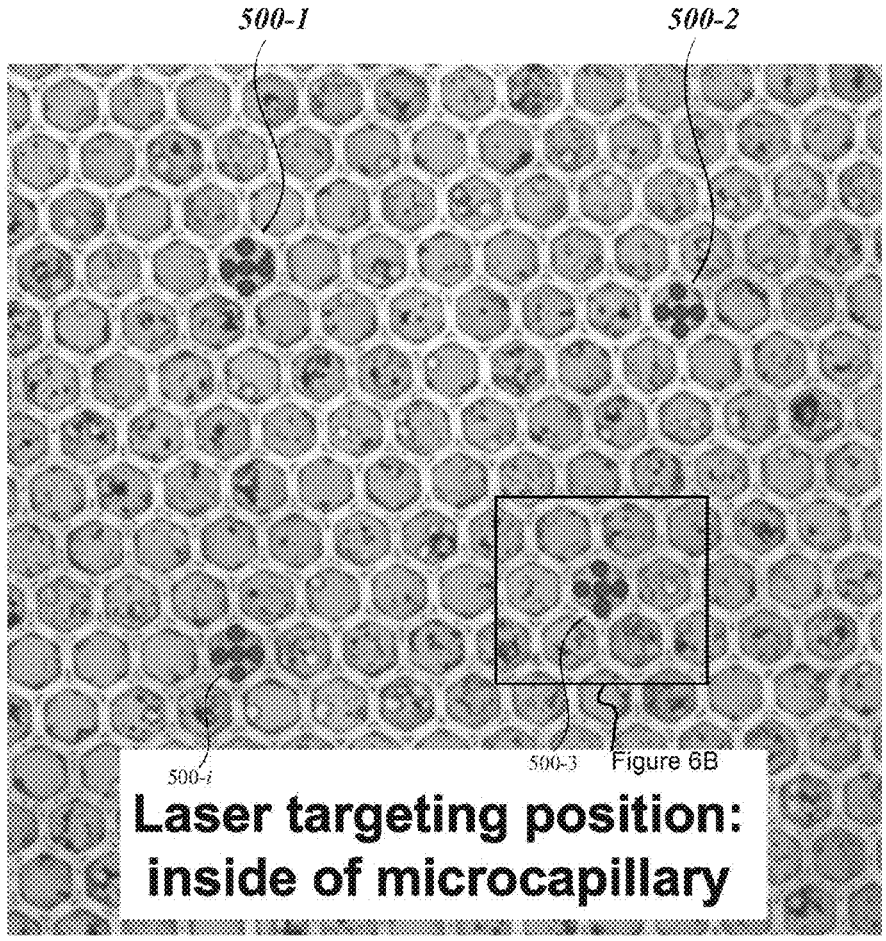
FIG. 6A-6B.
Figure 6B:
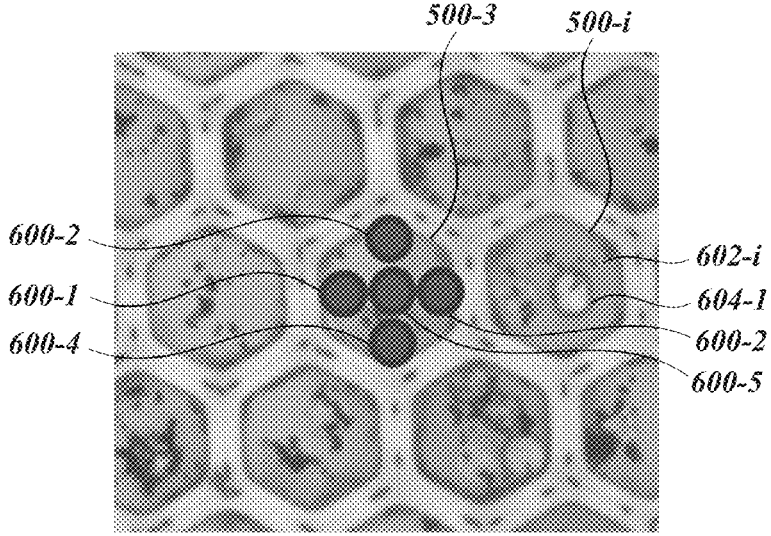
Figures 7G, 7H, 7I, 7J, 7K, 7L:
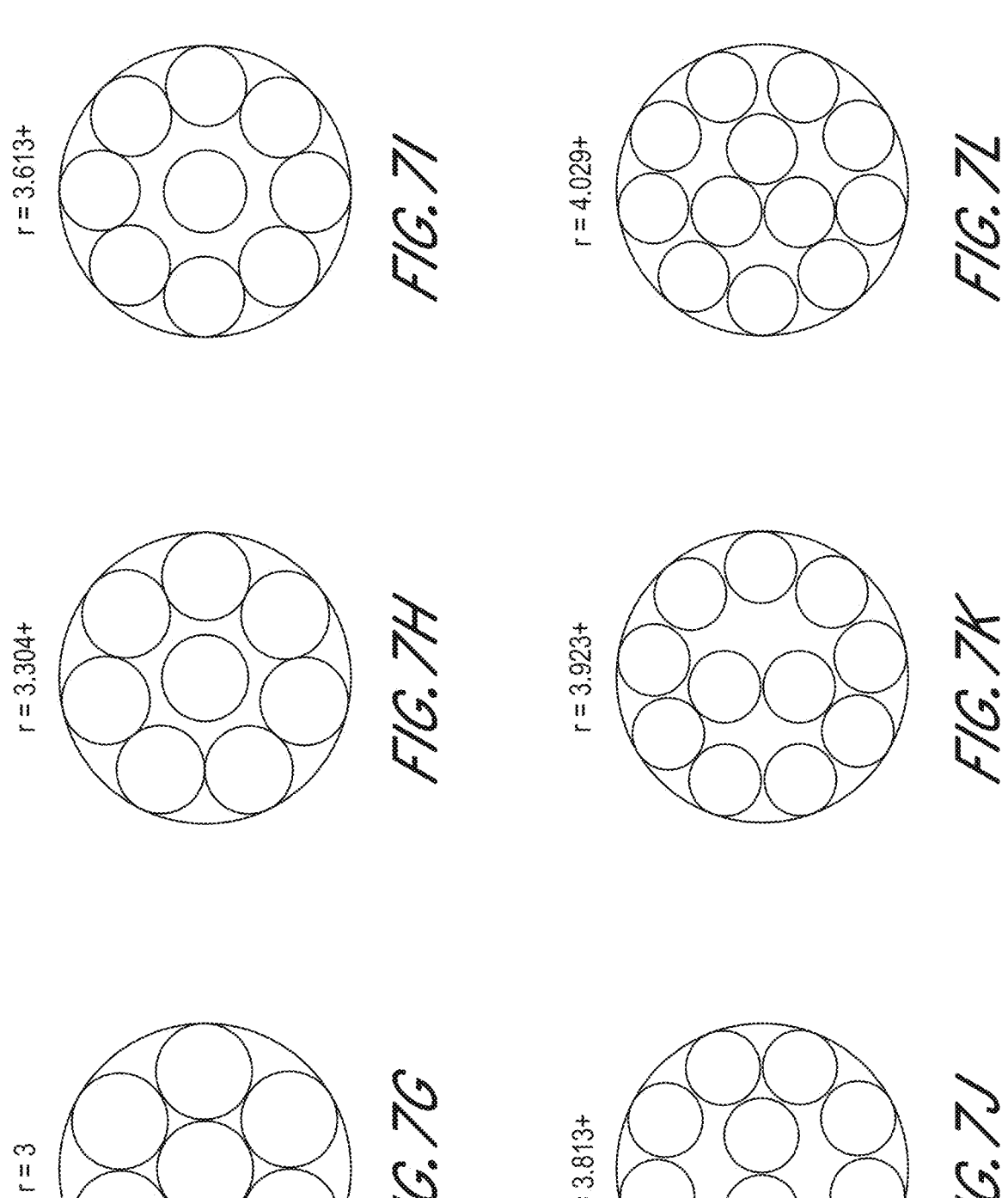
Figures 8A, 8B:
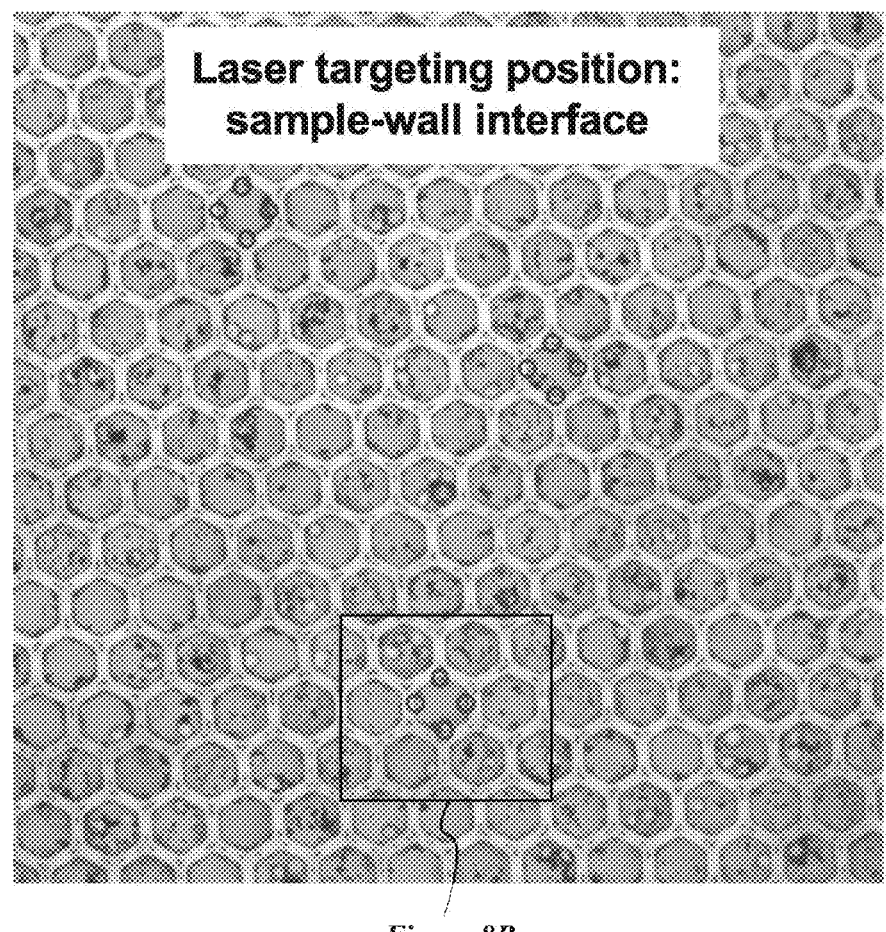
FIG. 8A-8B.
Figure 8B:
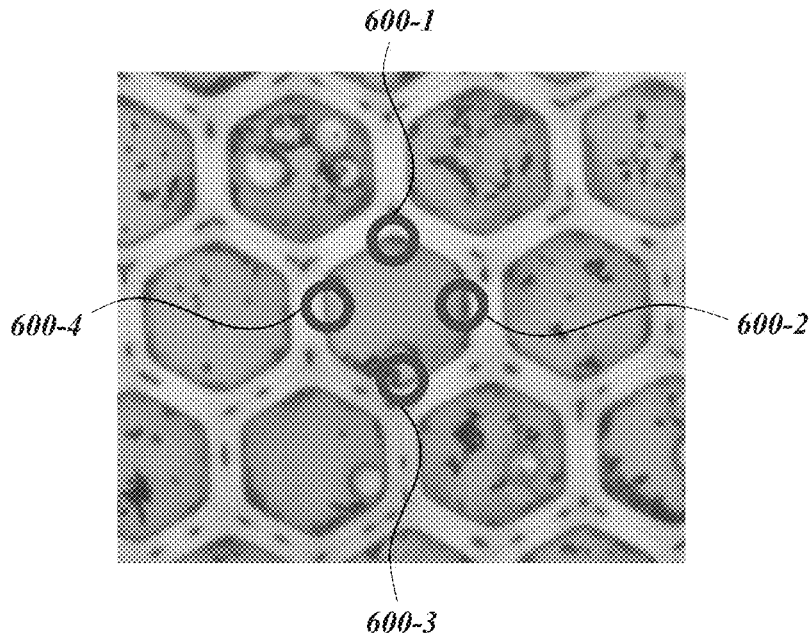
Figures 9A, 9B:
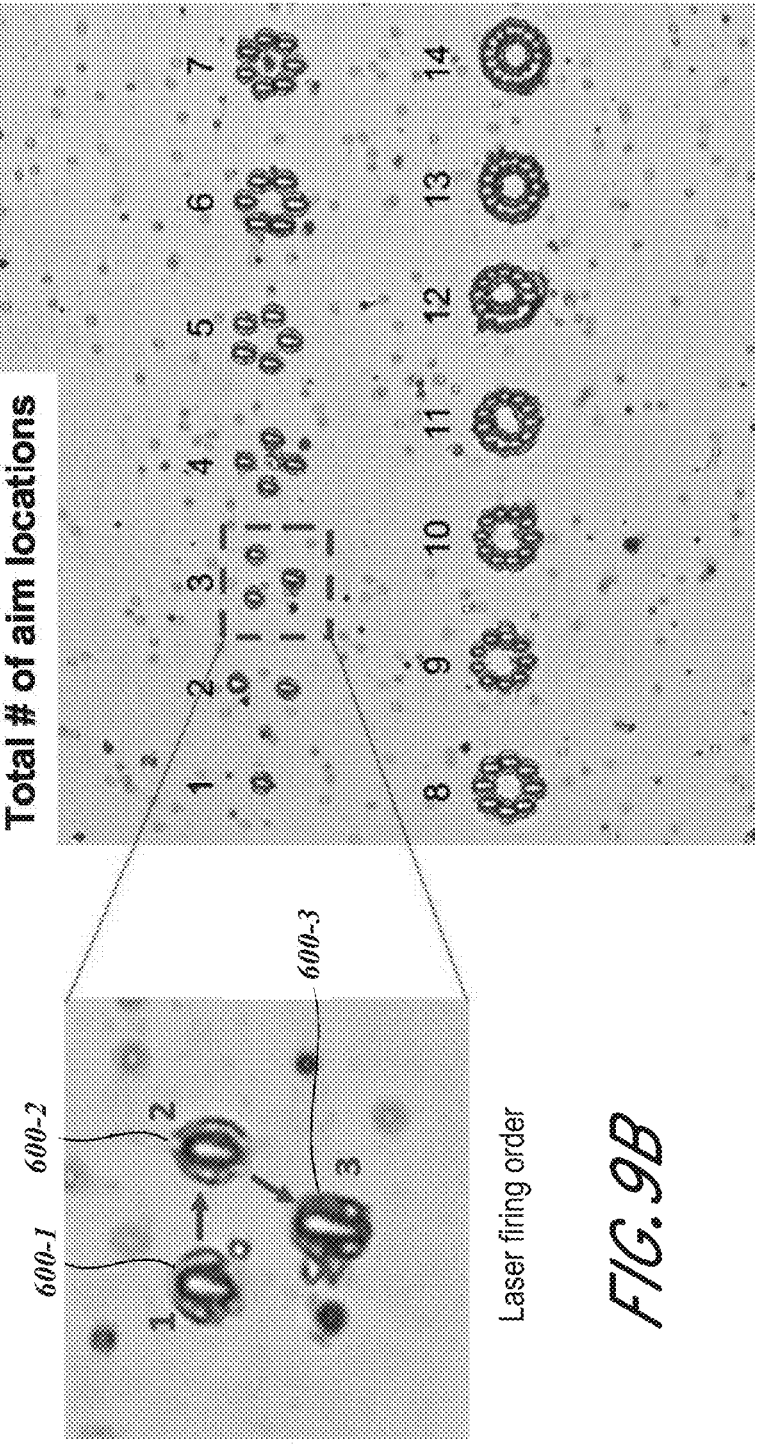
FIG. 9A-9B.

In some embodiments, the sample (e.g., sample 602-i including cell 604-1 of FIG. 6B) of a microcapillary well 500 includes one or more opaque beads or a similar absorbing material. Accordingly, in some embodiments, illuminating the one or more opaque beads with the beam 104 of the laser 102 is desired to recovery the content from the microcapillary well 500. In such embodiments, the beam 104 illuminates a portion of a visible surface area of each of the one or more opaque beads in order to maximize energy transfer to the absorbing material. In some embodiments, the beam 104 of the laser 102 is directed towards a plurality of targets that collectively consume a signification portion of a surface area of the microcapillary well 500 (e.g., a portion in a range of from 30% to 100%). For instance, FIG. 6A illustrates a plurality of microcapillary 500-1 through 500-i, each of which includes a plurality of targets 600 formed in a cross (e.g., "+") shape.

Figure 11B:
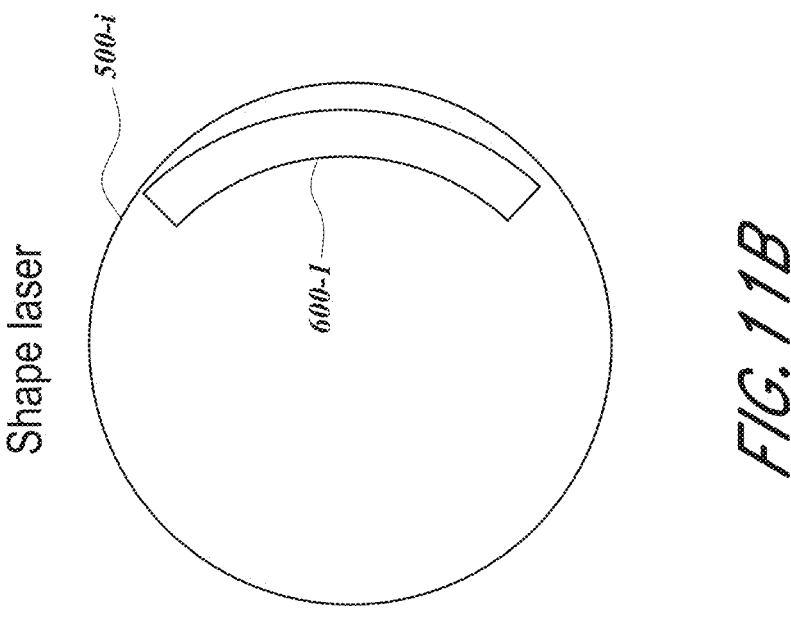
FIGS. 11A-11B illustrate a first cross section and a second cross section of a beam of a laser respectively, in accordance with an exemplary embodiment of the present disclosure.
Figure 11A:
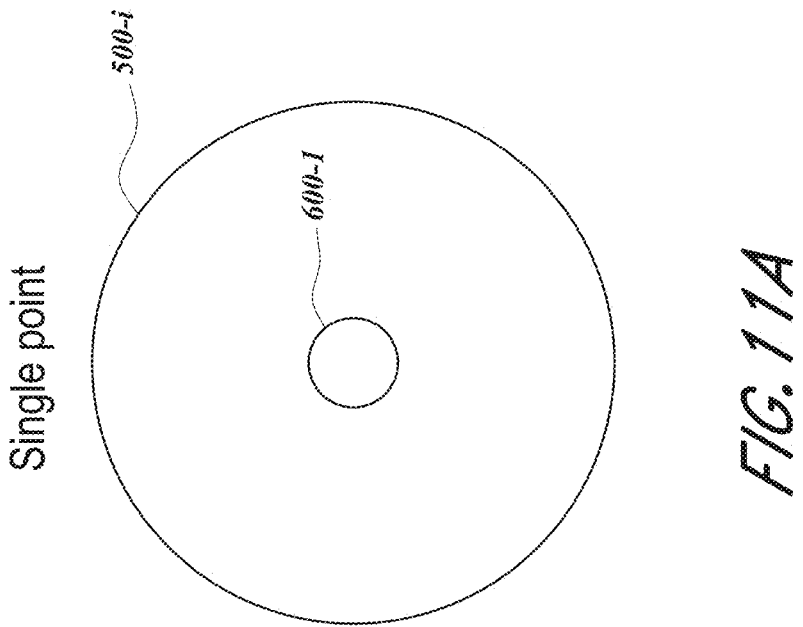

Referring to FIGS. 7A through 7L, in some embodiments, a shape of the plurality of targets 600 pulsed by the laser 102 within a single microcapillary well 500 is determined in accordance with a cross section of the beam 104 and a shape of the microcapillary well. In the present embodiment, both the cross section of the beam 104 and the shape of the microcapillary well 500 are assumed circular (e.g., a circular beam target 600-1 as illustrated in FIG. 11A). However, the present disclosure is not limited thereto. In some embodiments, the cross section of the beam 104 is of a non-circular shape (e.g., a crescent, or blade-like, shape target 600-1 as illustrated in FIG. 11B). In some embodiments, the beam 104 is directed towards the target as a point laser (e.g., without substantially altering a cross section of the beam, due to the coherent nature of lasers), and the target is illuminated in a corresponding circular shape. The mathematically optimal solution for filling a larger exterior circle (e.g., a microcapillary well 500) with a plurality of uniform interior whole (e.g., no concentric circles) circles (e.g., cross section of beam 104) is described by a packing efficiency of the above shapes and forms. This packing efficiency is a ratio of an area of the larger circle with respect to an area collectively consumed by the plurality of uniform smaller. See, Kravitz, S., 1967, "Packing Cylinders into Cylindrical Containers," Math. Mag., 40, pg. 65; Friedman, E., "Circles in Circles," Stetson University, print, each of which is hereby incorporated by reference in its entirety. In FIGS. 7A through 7L, "r" represents a radius of a smallest known external circle (e.g., microcapillary well 500) with an increasing number of internal unit circles.

Figure 10:
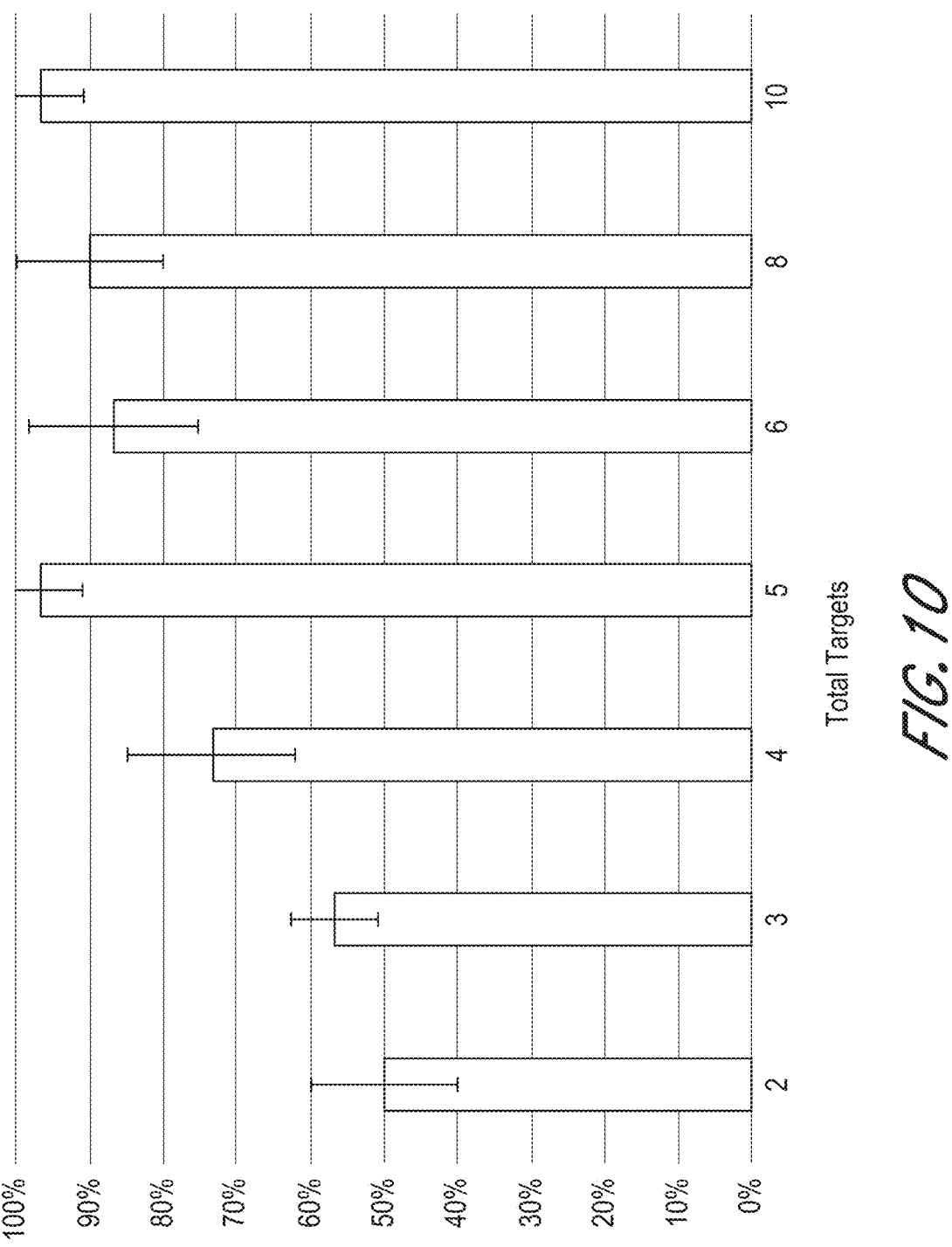
FIG. 10 illustrates a graph of an amount of a content recovery from a sample with respect to a number of pulses of a laser towards the sample, in accordance with an exemplary embodiment of the present disclosure.

Referring to FIG. 8A through FIG. 10, in some embodiments, the sample is free of absorbing material. Accordingly, extracting the content from the microcapillary array 132 includes directing (e.g., using the galvanometer system 106) the beam 104 of the laser 102 towards an interface between the content of the sample and the microcapillary well 500 (e.g., an internal wall of the microcapillary well 500). In some embodiments, the directing the beam 104 of the laser 102 towards the interface includes pulsing the laser towards a plurality of targets. In some embodiments, the plurality of targets 600 of the pulsing towards the interface is formed as a circle with each respective target being at equally spaced interval around the circle. For instance, referring to FIG. 9A, a spacing internal for the plurality of targets for a number of targets in a range of from 1 to 14 targets is depicted. While the present disclosure is not limited to a particular number of targets in the plurality of targets, FIG. 10 illustrates an efficiency of recovery with respect to the number of targets As illustrated in FIG. 10, in some embodiments an optimal number of targets per microcapillary well 500 was determined to be greater than or equal to 5. In some embodiments an optimal number of targets per microcapillary well 500 was determined to be greater than or equal to 6. In some embodiments an optimal number of targets per microcapillary well 500 was determined to be greater than or equal to 8. In some embodiments an optimal number of targets per microcapillary well 500 was determined by recovery percentage, wherein the recovery percentage was equal to or greater than 80%. In some embodiments an optimal number of targets per microcapillary well 500 was determined by recovery percentage, wherein the recovery percentage was equal to or greater than 85%. In some embodiments an optimal number of targets per microcapillary well 500 was determined by recovery percentage, wherein the recovery percentage was equal to or greater than 90%. In some embodiments an optimal number of targets per microcapillary well 500 was determined by recovery percentage, wherein the recovery percentage was equal to or greater than 95%. In some embodiments an optimal number of targets per microcapillary well 500 was determined by recovery percentage, wherein the recovery percentage was equal to or greater than 96%. In some embodiments an optimal number of targets per microcapillary well 500 was determined by recovery percentage, wherein the recovery percentage was equal to or greater than 97%. In some embodiments an optimal number of targets per microcapillary well 500 was determined by recovery percentage, wherein the recovery percentage was equal to or greater than 98%. In some embodiments an optimal number of targets per microcapillary well 500 was determined by recovery percentage, wherein the recovery percentage was equal to or greater than 99%. In some embodiments an optimal number of targets per microcapillary well 500 was determined by recovery percentage, wherein the recovery percentage was equal to 100%. In some embodiments an optimal number of targets per microcapillary well 500 was determined to be greater than or equal to 10. However, the present disclosure is not limited thereto as the optimal number can depend on a variety of factors. Referring to FIG. 9B, an order of firing the plurality of targets 600 is illustrated for three total targets. In the illustrated embodiment, the beam 104 of the laser 102 is directed towards a first target 600-1, and then positions to direct the beam 104 towards a second target 600-1, and finally a third target 600-3. While FIG. 9B depicts the positioning and directing in an orderly clockwise manner, the present disclosure is not limited thereto. For instance, in some embodiments, an order of pulsing the plurality of targets 600 is determined to minimize a distanced collectively traversed by the beam 104 during transitions between respective targets.

In some embodiments, the galvanometer system 106 includes a galvanometer-resonant scanner. Utilizing a galvanometer-resonant scanner provides improved positioning capabilities of the guiding system 100. For instance, the galvanometer-resonant scanner improves a rate of positioning the laser 102 from a first microcapillary well 500-1 to a second microcapillary well 500-2, or the like, and therefore improves an elapsed time to extract and recovery the content from the microcapillary array 132. For instance, in some embodiments, the galvanometer-resonant scanner increases a speed of recovering the content from the microcapillary tube in a range of from a factor of 8 to a factor of 12 (e.g., a ten-fold increase in throughput of recovery from an hour to six minutes for a given number of extractions and recoveries). In some embodiments, the galvanometer-resonant scanner is a commercially available galvanometer-resonant scanner, such as a Thoriabs LSK-GR08.

Referring to FIGS. 11A and 11B, in some embodiments, the guiding system 100 of the system 10 includes one or more spatial light modulators that distort a shape (e.g., cross section) of the beam 102, allowing the beam 104 to pulse a target with a non-circular shape. The one or more spatial light modulators utilize a liquid crystal on silicon (LCoS) device disposed between a first transparent thin-film transistor (TFT) and a silicon semiconductor. The one or more spatial light modulators produce high-resolution, high-speed reflective phase modulation with individually addressable pixels, allowing each addressable pixel to direct a portion of the beam 102 independently, and therefore, manipulate a cross section of the beam 104. Furthermore, in such embodiments in which the system includes the one or more spatial light modulators, more than one target can be pulsed with a single pulse of the laser 102 or, similarly, a larger sized target can be pulsed by the laser 102 within a single field of view, further decreasing an elapsed time to extract and recovery the sample from the microcapillary array. For instance, FIG. 11A illustrates a cross section of the beam 104 at a first target 600-1, which is typically associated with a point laser. On the other hand, a second target 600-2 of FIG. 11B has a cross section that is shaped in a crescent, or blade-like, shape due to the add individually addressable pixels of the one or more spatial light modulators produce high-resolution. One skilled in the art will know of other plausible cross sections of the beam 104 that are not expressly contemplated herein. In some embodiments, the one or more spatial light modulators include a commercial spatial light modulator, such as a Holoeye Pluto-2 or a Thor Exulus-HD1.

In some embodiments, the system 10 utilizes a digital micromirror device to direct the beam 104 of the laser 102 towards a target in with a configurable cross-section (e.g., as described supa). In some embodiments, the digital micromirror device is utilized in substitute for the spatial light modulator. The digital micromirror device includes a plurality of mirrors disposed on a surface of the device. In some embodiments, the plurality of mirrors are in a range of from $1 \cdot 10^3$ to mirrors $1 \cdot 10^8$ mirrors, from $1 \cdot 10^4$ to mirrors $1 \cdot 10^8$ mirrors, from $1 \cdot 10^4$ to mirrors $9 \cdot 10^5$ mirrors, from $1 \cdot 10^4$ to mirrors $7 \cdot 10^5$ mirrors, or $5 \cdot 10^4$ to mirrors $5 \cdot 10^5$ mirrors. In some embodiments, the digital micromirror device is a commercial digital micromirror device, such as a Mirrorcle Integrated MEMS Mirrors (A5M24.1-2400AL).

In some embodiments, the optical train of the laser guiding system 100 includes a scan lens 108. The scan lens 108 provides a flat image plane with minimal optical aberration across the plane and, in some embodiments, a relatively large field of view. In some embodiments, the large field of view is particularly useful for the present disclosure to the single field of view of the objective lens 112. In some embodiments, the scan lens 108 is a commercial scan lens such as a Thorlabs Large Field of View Scan Lens or a Thorlabs Scan Lens (LSM03-VIS).

In some embodiments, the optical train includes a tube lens 110. In some embodiments, the tube lens 110 includes a telecentric tube lens. In some embodiments, the tube lens 110 is a commercially available tube lens, such as a Thorlabs Standard Tube Lens (TTL-200) or a Thorlabs Laser Scanning Tube Lens (TL200-CLS2).

In some embodiments, the laser guiding system 100 includes one or more high-resolution cameras 120. In some embodiments, the one or more cameras 120 includes a black and white camera. In some embodiments, the one or more cameras 120 includes a color camera. In some embodiments, the laser guiding system 100 includes one real-time, high-resolution camera and one color camera. In some embodiments, the imaging system consists of one color camera and one monochrome camera, in order to expand the range of detection. However, the present disclosure is not limited thereto. For instance, in some embodiments the one or more cameras 120 includes a thermal graphic camera (e.g., an infrared camera) aiding in the recovery of the content of the microcapillary array.

In some embodiments, while the two cameras see exactly the same field of view, they capture different information. For instance, the color camera captures RGB light while the monochrome (e.g., black and white) camera captures transmitted light in the same field. In some embodiments, to capture two different images one can employ a high-speed pulsed light source that is synchronized with the image capturing process. In some embodiments, to capture two different images one can employ a high-speed pulsed light source (e.g., laser 102) in combination with two cameras.

In some embodiments, the guiding system 100 includes an imaging guiding system for use imaging the microcapillary array 132 using the one or more cameras 120. In some embodiments, the imaging guiding system facilitates control of the control or cameras 120, such as control of a capture sequence, image capture settings, and the like. In some embodiments, the imaging guiding system includes one or more mirrors 124-1 that provide a new field of view for the one or more cameras. In some embodiments, the one or more mirrors 124-1 includes a corresponding subset of mirrors for each camera 120 in the one or more mirrors, allowing each camera to have a separately configurable field of view. Further, in some embodiments, the one or mirrors 124-1 of the imaging system are either fixed or provided one or more degrees of freedom.

In some embodiments, the optical train is coupled to one or more emission filters optimized for a particular wavelength, fluorophore, and/or ratiometric dye.

Now that details of a system 10 for recovering a content of a sample from a microcapillary array 132 have been disclosed, details regarding a flow chart of processes and features for implementing a method 200 of the system 10, in accordance with an embodiment of the present disclosure, are disclosed with reference to FIG. 2 through FIG. 11B.

Block 202. Referring to block 202 of FIG. 2, a system (e.g., the system 10 of FIG. 1) for recovering the content of a sample (e.g., sample 602-1 of FIG. 6B) is provided. The system 10 includes a microcapillary array 132 that further includes a plurality of microcapillary wells 500. In some embodiments, each respective microcapillary well 500 accommodates a unique sample or a replicate of a sample of a different microcapillary well 500. Accordingly, each microcapillary well 500 is configured to accommodate a respective sample 602 of biological material. As described supra, the biological material, in some embodiments, includes one or more cell. These one or more cells include mammalian cells, fungal cells, bacterial cells, insect cells, plant cells, or a combination thereof. In some embodiments, the one or more cells is intact and no longer capable of cellular growth.

In some embodiments, the microcapillary array is coupled to a sample stage (e.g., sample stage 130 of FIG. 1), that assists in facilitating recovery of the sample. In some embodiments, the sample stage 130 includes a collection slide 134 that receives an extracted sample 602.

Block 204. Referring to block 204, the method further includes positioning the laser 102 to target a first microcapillary well 500-1 in the plurality of microcapillary wells 500 of the microcapillary array 132.

In some embodiments, the positioning the laser 102 utilizes a guiding system (e.g., a laser guiding system 100 of FIG. 1), which allows the laser 102 to remain stationary while other components of the system 10 (e.g., the objective lens 112 of FIG. 1, the sample stage 130 of FIG. 1, the galvanometer system 106 of FIG. 1, etc.) move relative to the laser 102. In some embodiments, the laser guiding system 100 includes the laser 102, a laser scanning assembly (e.g., a galvanometer system and/or mirror), a galvanometer resonance scanner, etc.), a scan lens (e.g., scan lens 108 of FIG. 1) system, and a tube lens (e.g., tube lens 106 of FIG. 1). In some embodiments, the laser guiding system is a commercial scanner system, such as a ScannerMAX Compact-506RE system. Furthermore, in some embodiments a rate of positioning of the sample stage 130 is less than a rate of positioning of the laser guiding system 100. In some embodiments, the laser scanning assembly includes a device that alters a shape of the beam from the laser 102. In some embodiments, the device includes the galvanometer system and/or mirror 106, a digital micromirror device, one or more spatial light modulator, or a combination thereof.

In some embodiments, the laser 102 emits a beam (e.g., beam 104 of FIG. 1) at a discrete wavelength in a range of from 213 nm to 1380. For instance, in some embodiments the wavelength of the beam 104 from the laser 102 is 355 nm, 514 nm, 532 nm, or 1064 nm.

In some embodiments, the first microcapillary well 500-1 is identified from the plurality of microcapillary wells 500. For instance, in some embodiments, one or more cameras (e.g., one or more cameras 120 of FIG. 1) and/or a fluorescence light source 116 image some or the entire microcapillary array 132 during the positioning of the laser 102. In some embodiments, the one or more cameras 120 image some or the entire microcapillary array 132 during an extracting of the content from the microcapillary array. In some embodiments, the microcapillary well 500 for recovery is identified through expression of an antibody from a cell accommodated in the microcapillary well 500.

Block 206. Referring to block 206, the method includes pulsing the laser 102 towards the first microcapillary well 500-1. The pulsing disrupts the surface tension of the sample within the microcapillary well, allowing for extraction of the sample. In some embodiments, the laser 102 pulses a plurality of subsections (e.g., targets 600) of the first microcapillary well 500-1. In some embodiments, the plurality of subsections is disposed within an internal portion of the microcapillary well 500 (e.g., target 600-5 of FIG. 6B), disposed at an interface between an inner surface of the microcapillary well 500 and the content of the microcapillary well 500 (e.g., target 600-2 of FIG. 8B), or a combination thereof. In some embodiments, the laser 102 pulses in a range of from 2 subsections to 20 subsections, from 2 subsections to 14 subsections, from 2 subsections to 14 subsections, or from 2 to 10 subsections. In some embodiments, the laser 102 pulses a plurality of times at each respective subsection. For instance, in some embodiments, the laser 102 pulses in a range of from 1 time to 30 times at a subsection, 1 time to 25 times at the subsection, 1 time to 20 times at the subsection, or greater than or equal to 5 times at the subsection. Furthermore, in some embodiments, the laser 102 pulses at a frequency in a range of from 1 kHz to 60 kHz, from 1 kHz to 40 kHz, from 5 kHz to 40 kHz, from 15 kHz to 25 kHz, or from 5 kHz to 10 kHz (e.g., 5,000 to 10,000 laser pulses per second). Additionally, in some embodiments, each pulse of the laser 102 has a duration in a range of from 0.05 ns to 100 ns, from 0.1 ns to 50 ns, from 0.1 ns to 40 ns, from 0.1 ns to 25 ns, from 0.1 ns to 20 ns, or form 5 ns to 20 ns. In some embodiments, each pulse of the laser 102 has a duration in a range of from 5 nanoseconds (ns) to 20 ns. In some embodiments, each pulse of the laser 102 has a duration in a range of from 5 nanoseconds (ns) to 15 ns. In some embodiments, each pulse of the laser 102 has a duration in a range of from 8 nanoseconds (ns) to 18 ns. In some embodiments, each pulse of the laser 102 has a duration in a range of from 10 nanoseconds (ns) to 18 ns. In some embodiments, each pulse of the laser 102 has a duration in a range of from 10 nanoseconds (ns) to 15 ns. In some embodiments, each pulse of the laser 102 has a duration in a range of 15 ns. In some embodiments, the duration of the pulse is approximately about 15 ns. As an example, in some embodiments, the laser 102 pulses 5 subsections (e.g., targets 600) of each respective microcapillary well 500. Each pulsing of a respective subsection of each respective microcapillary well 500 emits 10 laser pulses. Further, each of the 10 laser pulses has a duration of 15 ns.

Block 208. Referring to block 208, the method includes extracting the content of the sample from the first microcapillary well 500-1 to recover the content. In some embodiments, the content from the microcapillary array is recovered in a collection slide (e.g., collection slide 134 of FIG.

1), such that each sample recovered from a respective microcapillary well 500 is received in a corresponding well of the collection slide. In some embodiments, the wells of the collection slide are dry upon recovery of the sample (e.g., the well does not include a fluid). In some embodiments, a lysis buffer is added to the wells of the collection slide after recovery of the sample from microcapillary array 130.

Figure 12:
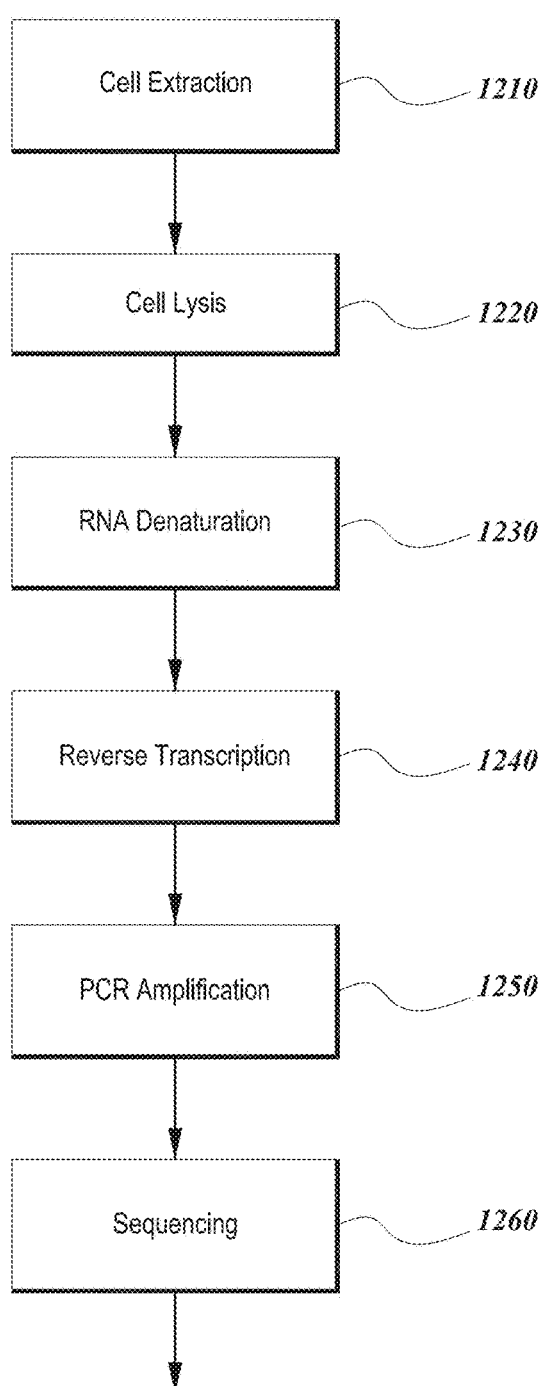
FIG. 12 provides a flow chart of a workflow for sequencing a sample, in accordance with an exemplary embodiment of the present disclosure.

Now that details of a method 200 for recovering a content of a sample from a microcapillary array 132 have been disclosed, details regarding workflow for implementing a method 200 of the system 10, in accordance with an embodiment of the present disclosure, are disclosed with reference to FIG. 12.

Now that details of workflow 1200 for recovering a content of a sample from a microcapillary array 132 have been disclosed, details regarding an example of extracting, recovering, and synthesizing the content, in accordance with an embodiment of the present disclosure, are disclosed.

In some embodiments of the workflow 1200, a step (C) of extracting the content from the first microcapillary well, thereby recovering the content of the first microcapillary well. In some embodiments of the workflow 1200, the content of the extracting and recovering extracting (e.g., cell extraction 1210) is disposed onto a collection slide. In some embodiments, the collection slide comprises one or more collection wells containing a lysis buffer, wherein the lysis buffer is added to the one or more collection wells prior to the recovering the content. In some embodiments, the collection slide comprises one or more collection wells which do not contain a lysis buffer, wherein the lysis buffer is not added to the one or more collection wells prior to the recovering the content (C). In some embodiments, the method further comprises, following the extracting and the recovering (C), disposing the content onto a collection slide and freezing the collection slide. In some embodiments, the collection slide is subsequently thawed. In some embodiments, the thawed collection slide is subjected to treatment to denature the RNA. In some embodiments, the thawed collection slide comprising the denatured RNA is subjected to RT-PCR amplification. In some embodiments, the RT-PCR amplification product is quantified. In some embodiments, the RT-PCR amplification product is sequenced. In some embodiments, the method further comprises, following the extracting and the recovering (C), disposing the content onto a collection slide and transferring the content of the collection slide to a PCR plate and freezing the PCR plate. In some embodiments, the PCR plate is subsequently thawed. In some embodiments, the thawed the PCR plate is subjected to treatment to denature the RNA. In some embodiments, the thawed the PCR plate comprising the denatured RNA is subjected to RT-PCR amplification.

In some embodiments, the sample being recovered comprises a population of variant proteins and/or a population of nucleic acids encoding the variant proteins, which can in some embodiments be generated using a genetic library in a biological expression system, for example in an in vitro (i.e., cell-free) expression system or in an in vivo or cellular expression system. Exemplary cellular expression systems include, for example, animal systems (e.g., mammalian systems), fungal systems (e.g., yeast systems), bacterial systems, insect systems, or plant systems. In specific embodiments, the expression system is a mammalian system or a yeast system. In specific embodiments, the expression system is an avian system (for example, a chicken system). The expression system, whether cellular or cell-free, typically comprises a library of genetic material encoding the population of variant proteins. Cellular expression systems offer the advantage that cells with a desirable phenotype, for example cells that express a particular variant protein of interest, such as a variant protein capable of associating with an immobilized target molecule with high affinity, can be grown and multiplied, thus facilitating and simplifying the identification and characterization of the proteins of interest expressed by the cells. In some embodiments, the biological expression system comprises a mammalian cell line. In some embodiments, the mammalian cell line is selected from the group consisting of CHO-K1, CHO-S, HEK293T, and/or any derivatives of these cell types. In some embodiments, the mammalian cell line is CHO-K1. In some embodiments, the mammalian cell line is CHO-S. In some embodiments, the mammalian cell line is HEK293T. In some embodiments, the mammalian cell line is selected from the group consisting of human, mouse, and/or rat hybridoma cell lines. In some embodiments, the mammalian cell line is a human hybridoma cell line. In some embodiments, the mammalian cell line is a mouse hybridoma cell line. In some embodiments, the mammalian cell line is a rat hybridoma cell line. In some embodiments, the mammalian cell line is a B cell line. In some embodiments, the mammalian cells comprise B cells. Genetic libraries encoding large populations of variant proteins are well known in the art of bioengineering. Such libraries are often utilized in systems relying on the process of directed evolution to identify proteins with advantageous properties, such as high-affinity binding to target molecules, stability, high expression, or particular spectroscopic, e.g., fluorescence, or enzymatic activities. Often the libraries include genetic fusions with sequences from the host expression system, for example fragments of proteins directing subcellular localization, where the expressed population of variant fusion proteins are directed by the targeting fragment to a particular location of the cell or virus particle for purposes of activity screening of the variant protein population. Large numbers of variant proteins (e.g., $10^8$ variants, $10^8$ variants, $10^{10}$ variants, $10^2$ variants, or even more variants) can be generated using routine bioengineering techniques, as is well known in the art. Such libraries can include any of the variant proteins described herein, including antibodies, antibody fragments, single chain variable fragments, or natural protein ligands. In some embodiments, the system of the present invention allows for accurate pairing of VH/VL (variable heavy chains and variable light chains).

In some embodiments, the variant proteins (or variant proteins encoded by nucleic acids) are soluble proteins, for example, soluble proteins that are secreted by a cellular expression system. Exemplary soluble variant proteins include antibodies and antibody fragments, alternative protein scaffolds, such as disulfide-bonded peptide scaffolds, extracellular domains of cell-surface receptor proteins, receptor ligands, such as, for example, G-protein coupled receptor ligands, other peptide hormones, lectins, and the like. In other embodiments, however, it may be desirable for the variant proteins to be membrane-associated proteins, for example, proteins remaining associated with the surface of a cell or a viral particle in an expression system. Isolation of the contents of the desired microcapillary according to workflow 1200 thereby enables the identification and characterization of contents.

In some embodiments, the content in the microcapillary wells comprises genetic material. In some embodiments, the sample comprises the genetic material of one or more intact cells with a desired phenotype. In some embodiments, the phenotype of the one or more intact cells identifies B cells.

In some embodiments, the phenotype of the one or more intact cells identifies subgroups of B cells. In some embodiments, the genetic material comprises an antibody sequence. In further embodiments, the antibody sequence comprises a heavy chain and a light chain. In some embodiment, the genetic material comprises mRNA. In further embodiments, reverse transcription is performed on the mRNA. In further embodiments, amplification of the heavy chain and the light chain is performed in separate reactions.

Example 1: Cell Extraction & Lysis

Referring to FIG. 12, a framework of a workflow 1200 for recovering a content of a sample from a microcapillary array 132 is provided.

Step 1210. Within the microcapillary array 132 a target sample is identified, such as a target anti-body of interest, for recovery and sequencing. Accordingly, a laser (e.g., laser 102 of FIG. 1) extracts one or more cells from the microcapillary array 132 (e.g., method 200 of FIG. 2) expressing the anti-body of interest. Upon extraction, each respective cell (e.g., cell 604-1 of FIG. 66) from the microcapillary well 500 (e.g., microcapillary well 500-3 of FIG. 6B) is recovered in a corresponding well of a collection slide (e.g., collection slide 134 of FIG. 1). As described supra, an aspect of the present disclosure is directed to providing recovery methods that do not require the cell to be capable of cellular growth upon extraction, but instead require the cell to be intact. Accordingly, the systems and methods of the present disclosure allow for extracting and recovering of the cell into a dry environment (e.g., an empty well).

Step 1220. A lysis buffer is prepared. The lysis buffer includes water, a recombinant RNAse inhibitor, triton (e.g., triton 100-X), a plurality of RT primers, and dNTP mix. In some embodiments, the lysis buffer contains water, recombinant RNAse inhibitor, triton, RT primers, and dNTP combination. Furthermore, in some embodiments, the RT primers are either gene specific or not gene specific. In some embodiments, the preparing the lysis buffer of step 1220 is conducted prior to the extracting (Step 1210) of the workflow 1200 for timing considerations.

The lysis buffer is supplied to each well of the collection slide 134 (e.g., collection slide 134 of FIG. 1). In some embodiments, each well of the collection slide 134 includes at least 8 μl of the lysis buffer. In some embodiments, each well of the collection slide 134 includes a minimum volume of the lysis buffer that is required to submerge a lower end portion of the well. In some embodiments, the collection slide 134 includes 18 wells slide. In some embodiments, the workflow 1200 utilizes a plurality of collection slides simultaneously. In some embodiments, the lysis buffer is supplied to a subset of wells of the collection slide 134. In some embodiments, the preparing and the supplying the lysis buffer is conducted prior to the extracting (Step 1210), allowing for recovery of the cell into a wet environment. In some embodiments, upon supplying the lysis buffer to each well of the collection slide 134, an agitation is applied to the collection slide 134 to ensure that each cell is coated with or submerged by the lysis buffer.

Figure 13A:
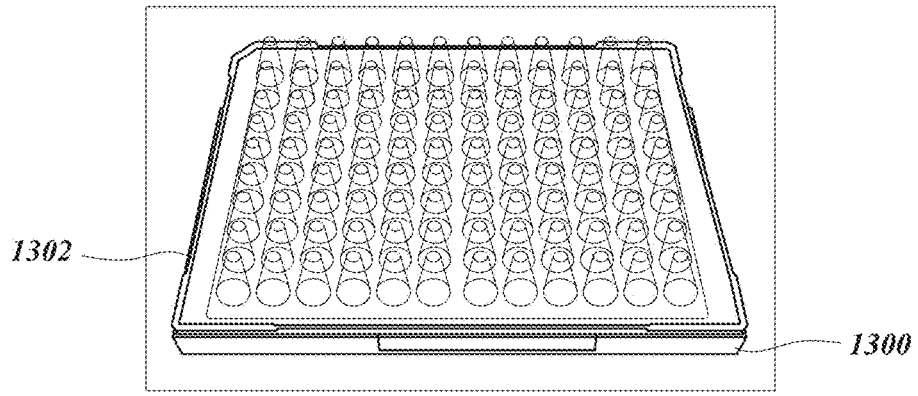
FIGS. 13A-13C illustrate transferring of one or more samples from a collection slide to a PCR plate.
Figure 13B:
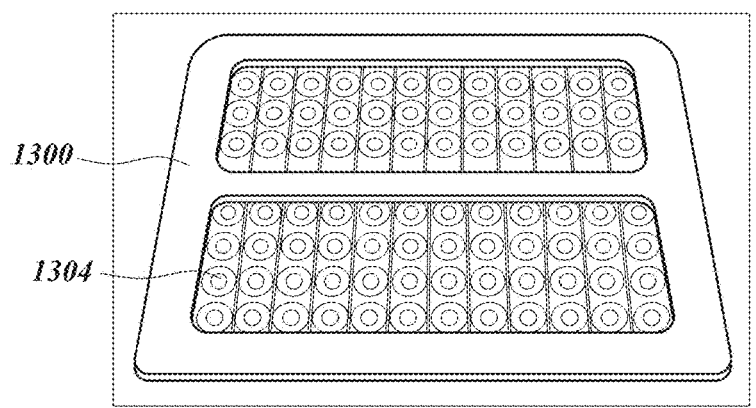
Figure 13C:
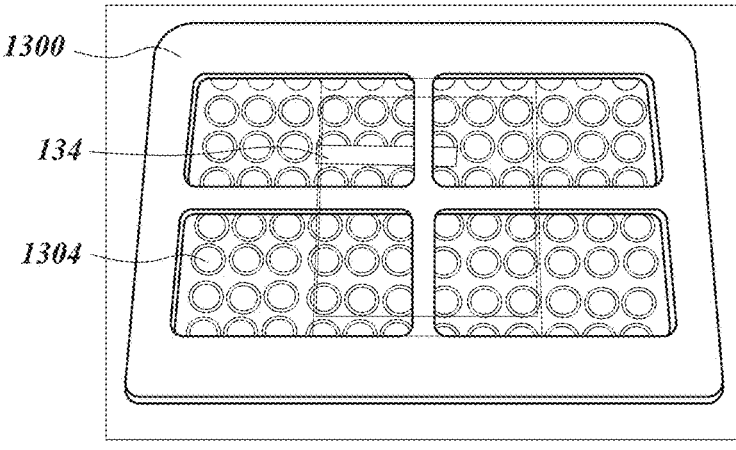

The samples of the collection slide 134 are transferred to a PCR plate (e.g., PCR plate 1302 of FIG. 13) for RNA denaturation and further analysis. As shown in FIG. 13A through FIG. 13B, the collection slide 134 is accommodated in a tray 1300 that includes a first portion and a second portion that removeably couple. In transferring the samples, each the collection slide 134 has an upward facing opening exposed to a surrounding environment (e.g., each well of the collection slide 134 is not capped) and accommodated in the first portion of the tray 1300, while one or more PCR strip caps 1304 are accommodated in the second portion of the tray 1300. In some embodiments, the number of the one or more PCR strip caps 1304 corresponds to a number of wells of the collection slide 134 and/or the number of wells of the PCR plate 1302. The PCR plate 1302 is inverted, such that an opening of each well is facing towards the opening of the collection slide, as illustrated in FIG. 13A. The second portion of the tray 1300 including the PCR strip caps 1304 is coupled to the first portion of the tray 1300. In some embodiments, the first portion of the tray 1300 including the collection slide 134 is not reoriented until the second portion of the tray 1300 is coupled to the first portion (e.g., a lower end portion of the first portion of the tray 1300 remains stationary and facing downwardly in the above-described portions of the transferring as illustrated in FIGS. 13A and 13B). In some embodiments, once the tray 1300 is coupled and the collection slide 134, the PCR plate 1302, and the PCR cap strips 1304 are fixed within the tray 1300, the tray 1300 is reoriented such that the lower end portion of the first portion of the tray 1300 is now facing upwards, as illustrated in FIG. 13C. In some embodiments, the coupled tray 1300 including the collection slide 134, the PCR plate 1302, and the PCR cap strips 1304 is accommodated by a centrifuge, forcing the cell lysate from the wells of the collection slide 134 into a lower end portion the wells of the PCR plate 132 with little to no residual liquid in the wells of the collection slide 134 while also compacting the cell lysate. In some embodiments, the centrifuging of the tray 1300 is conducted for a period of time in a range of from 0 to 180 s, from 30 s to 90 s, from 45 s to 75 s. In some embodiments, the centrifuging the tray 1300 is conducted for a period of time of approximately about 60 seconds. In some embodiments, the centrifuging the tray 1300 is conducted at a relative centrifugal force (e.g., G force) of in a range of from 2,000 G to 3,500 G, from 2,250 G to 3,500 G, from 2,500 G to 3,500 G, or from 2,750 G to 3,250 G. In some embodiments, the centrifuging the tray 1300 is conducted at a relative centrifugal force of approximately about 3,000 G.

In some embodiments, the initial volume of the cell lysate is retrieved from the collection slide 134. Accordingly, the initial volume is supplied to a first and a second well of the PCR plate wells, with allows for a cell lysate from one cell to be supplied to more than one well. In some embodiments, the initial volume is 8 micro-liters (μL), allowing for an equal distribution of 4 μL of the cell lysate per well of each respective PCR plate from same cell. For instance, in some embodiments the first well is utilized for light chain sequencing and the second well for heavy chain sequencing.

Once the one or more cells is extracted, recovered, and transferred to the PCR plate, the PCR plate is exposed to a rapid negative temperature differential (e.g., snap freeze) to cool the cells and solidify the content of the collection slide 134. This cooling of the cells completes the lysis of the cell and preserving the genomic content of the cell. In some embodiments, the rapid cooling of the cells is conducted by exposing the cells to a temperature in a range of from −90° C. to −70° C., −88° C. to −72° C., −86° C. to −74° C., −84° C. to −76° C., or from −82° C. to −78° C. In some embodiments, the rapid cooling of the cells is conducted by exposing the cells to a temperature of approximately about −80° C. In some embodiments, the rapid cooling of the cells is conducted by accommodating, and thereby exposing, the cells to solid carbon dioxide, also known as dry ice. In some embodiments, the rapid cooling of the cells is conducted for a period of time in a range of from 2.5 minutes to 7.5 minutes, from 3 minutes to 7 minutes, from 3.5 minutes to 6.5 minutes, from 4 minutes to 6 minutes, or from 4.5 minutes to 5.5 minutes. In some embodiments, the rapid cooling of the cells is conducted for a period of time of approximately about 5 minutes. Accordingly, the collection slide 134, is thawed bringing the contents to a fluid phase. In some embodiments, the thawing is conducted in by exposing the cells to a temperature in a range of from 0° C. to 10° C., from 0° C. to 8° C., or 2° C. to 6° C. In some embodiments, the thawing is conducted in by exposing the cells to a temperature of approximately about 4° C. In some embodiments, the thawing is conducted on a bed of ice. In some embodiments, the freezing and thawing is conducting while the cell lysate is accommodated within the collection slide 134, such that the cell lysate is transferred to the PCR plate 1302 after thawing within the collection slide 134.

Step 1230. In some embodiments, such as that in which the collection slide 134 is frozen and thawed, the PCR plate 1302 is rotated at high speed, forcing the cell lysate to a lower end portion of the respective well. In some embodiments, the rotating the PCR plate 1302 is as described supra with respect to the centrifuging the tray 1300. Once exposed to the high rotational speed, the PCR plate 1302 is accommodated in a thermal cycler at a first predetermined temperature for a first predetermined period of time. In some embodiments, the first temperature of the thermal cycler is in a range of from 78° C. to 66° C., from 76° C. to 68° C., or from 74° C. to 70° C. In some embodiments, the first temperature of the thermal cycler is approximately about 72° C. In some embodiments, the first predetermined period of time of exposure to the thermal cycler is in a range of from 2 minutes to 5 minutes, from 2 minutes to 4 minutes, or from 2.5 minutes to 3.5 minutes. In some embodiments, the first predetermined period of time of exposure to the thermal cycler is approximately about 3 minutes. Furthermore, in some embodiments, the PCR plate 1304 is maintained at a predetermined temperature in-between the steps of rotating the PCR plate 1302 at a high speed and accommodating the PCR plate 1302 within the thermal cycler. In some embodiments, the predetermined temperature is in a range of from 0° C. to 10° C., from 0° C. to 8° C., or 2° C. to 6° C. In some embodiments, the predetermined temperature is approximately about 4° C. In some embodiments, the maintaining at the predetermined temperature is conducted on a bed of ice. Accordingly, the collection slide 134 is subjected to treatment to denature the RNA.

Step 1240. A reverse transcription (RT) formulation is prepared. In some embodiments, the reverse transcription formulation is prepared prior to each use (e.g., each instance of the workflow 1200). The reverse transcription formulation includes a 10× RT buffer, water, a recombinant RNAse inhibitor, and a reverse transcriptase. A volume of the RT formulation is supplied to each well of the PCR plate 1302 that includes a cell lysate. In some embodiments, the volume of the RT formulation is in a range of from 2 pL to 10 pL or from 4 pL to 8 μL. In some embodiments, the volume of the RT formulation is approximately about 6 μL. Accordingly, the PCR plate 1302 including the cell lysates and RT formulation is accommodated in the thermal cycler at a second predetermined temperature for a second predetermined period of time. In some embodiments, the second temperature of the thermal cycler is in a range of from 48° C. to 36° C. from 46° C. to 38° C., or from 44° C. to 40° C. In some embodiments, the second temperature of the thermal cycler is approximately about 32° C. In some embodiments, the second predetermined period of time of exposure to the thermal cycler is in a range of from 80 minutes to 100 minutes, from 82 minutes to 98 minutes, from 84 minutes to 96 minutes, from 86 minutes to 94 minutes, or from 88 minutes to 92 minutes. In some embodiments, the second predetermined period of time of exposure to the thermal cycler is approximately about 90 minutes. This second accommodating in the thermal cycler provides reserve transcription.

Once reverse transcription is complete, the PCR plate 1302 is further accommodated in the thermal cycler at a third predetermined temperature for a third predetermined period of time. In some embodiments, the third temperature of the thermal cycler is in a range of from 78° C. to 62° C., from 76° C. to 64° C., from 74° C. to 66° C., or from 72° C. to 68° C. In some embodiments, the third temperature of the thermal cycler is approximately about 70° C. In some embodiments, the third predetermined period of time of exposure to the thermal cycler is in a range of from 10 minutes to 20 minutes, from 12 minutes to 18 minutes, or from 14 minutes to 16 minutes. In some embodiments, the third predetermined period of time of exposure to the thermal cycler is approximately about 15 minutes. This third accommodating in the thermal cycler provides reserve transcriptase. Furthermore, in some embodiments, the PCR plate 1304 is maintained at a predetermined temperature in-between each step in a subset of steps of the above-described reserves transcription of the workflow 2100. In some embodiments, the predetermined temperature is in a range of from 0° C. to 10° C., from 0° C. to 8° C., or 2° C. to 6° C. In some embodiments, the predetermined temperature is approximately about 4° C. In some embodiments, the maintaining at the predetermined temperature is conducted on a bed of ice.

Step 1250. A PCR formulation is preparing including a PCR master formulation, water, and gene-specific forward and/or reverse primers. A volume of the PCR formulation is supplied to each reaction well of the PCR plate 1304. In some embodiments, the volume of the PCR formulation is in a range of from 10 μL to 20 μL, from 12 μL to 18 μL, or from 14 μL to 16 μL. In some embodiments, the volume of the PCR formulation is approximately about 15 μL. After suppling the PCR formulation, the PCR plate 1304 is accommodated in the thermal cycler for a thermal cycle. In some embodiments, the thermal cycle includes exposing the PCR plate 1304 to a fourth predetermined temperature for a fourth predetermined period of time, exposing the PCR plate 1304 to a fifth predetermined temperature for a fifth predetermined period of time, and exposing the PCR plate 1304 to a further sub-thermal cycle of the thermal cycle. In some embodiments, the fourth predetermined temperature is approximately about 37° C. and the fourth predetermined period of time is about approximately 30 minutes. In some embodiments, the fifth predetermined temperature is approximately about 95° C. and the fifth predetermined period of time is about approximately 3 minutes. In some embodiments, the sub-thermal cycle of the thermal cycle includes a first condition exposing the PCR plate 1304 to a sixth predetermined temperature for a sixth predetermined period of time, a second condition exposing the PCR plate 1304 to a seventh predetermined temperature for a seventh predetermined period of time, and a condition exposing the PCR plate 1304 to an eighth predetermined temperature for an eighth predetermined period of time. In some embodiments, the sixth predetermined temperature is approximately about 98° C. and the sixth predetermined period of time is about approximately 20 s. In some embodiments, the seventh predetermined temperature is approximately about 65° C. and the seventh predetermined period of time is about approximately 15 s. In some embodiments, the eighth predetermined temperature is approximately about 72° C. and the eighth predetermined period of time is about approximately 1 minute. In some embodiments, the sub-thermal cycle of the thermal cycle is repeated for a number of repetitions before proceeding with the workflow 1200. In some embodiments, the number of repetitions of the sub-thermal cycle in a range of from 40 repetitions to 50 repetitions, from 42 repetitions to 48 repetitions, or 44 repetitions to 46 repetitions. In some embodiments, the number of repetitions of the sub-thermal cycle is 45 repetitions. In some embodiments, the third condition of a final repetition of the sub-thermal cycle is maintained for an additional period of time (e.g., 6 minutes for the final repetition instead of 1 minute for each subsequent repetition). In some embodiments, the additional period of time is in a range of from 1 minutes to 10 minutes, or from 1 minutes to 9 minutes, from 3 minutes to 7 minutes, or from 4 minutes to 6 minutes. In some embodiments, the additional period of time is 5 minutes. Keep at 4° C. (or on ice). Furthermore, in some embodiments, the PCR plate 1304 is maintained at a predetermined temperature in-between each step in a subset of steps of the above-described reserves transcription of the workflow 2100. In some embodiments, the predetermined temperature is in a range of from 0° C. to 10° C., from 0° C. to 8° C., or 2° C. to 6° C. In some embodiments, the predetermined temperature is approximately about 4° C. In some embodiments, the maintaining at the predetermined temperature is conducted on a bed of ice. Accordingly, the PCR plate 1302 subjected to RT-PCR amplification. In some embodiments, a period of time Step 1260. Conduct sequencing to recover genome of the RT-PCR amplification product. In some embodiments, the RT-PCR amplification product is quantified.

Accordingly, the present disclosure provides improved systems and methods for extracting and recovering a single cell from a microcapillary array. The extracting of the cell is conducted with a high level of precision and accuracy, allowing a laser to target one or more portions of a microcapillary array to optimize the extraction and recovery. Moreover, the systems and methods of the present disclosure yield a high throughput (e.g., greater than or equal to approximately about $1 \cdot 10^6$ extractions per hour. This combination of the high throughout with the high level of precision and accuracy in targeting yields vastly improves a quality of extraction and efficiency of recovery. Further, the systems and methods of the present disclosure to not require the inclusion of additional sample components or manipulations, such as radiation absorbing materials, thus simplifying and improving the efficiency of the screening techniques. Moreover, the systems and methods of the present disclosure allow for recovery an intact cell, that is not required to be capable of cellular growth (e.g., alive). This recovery of an intact, but not growing, cell allows for the recovery of the cell into a dry environment, as compared to requiring a wet environment to sustain the cell. Additionally, recovery of an intact, but not growing, cell according to the systems and methods of the present disclosure allows a designer of the present disclosure to omit culturing the cell over a period of days, greatly reducing an elapsed period of time from an initiation of the extracting of the cell to an initiation of the sequencing of the cell.

Example 2: Xploration Ngs Workflow

Figure 14:
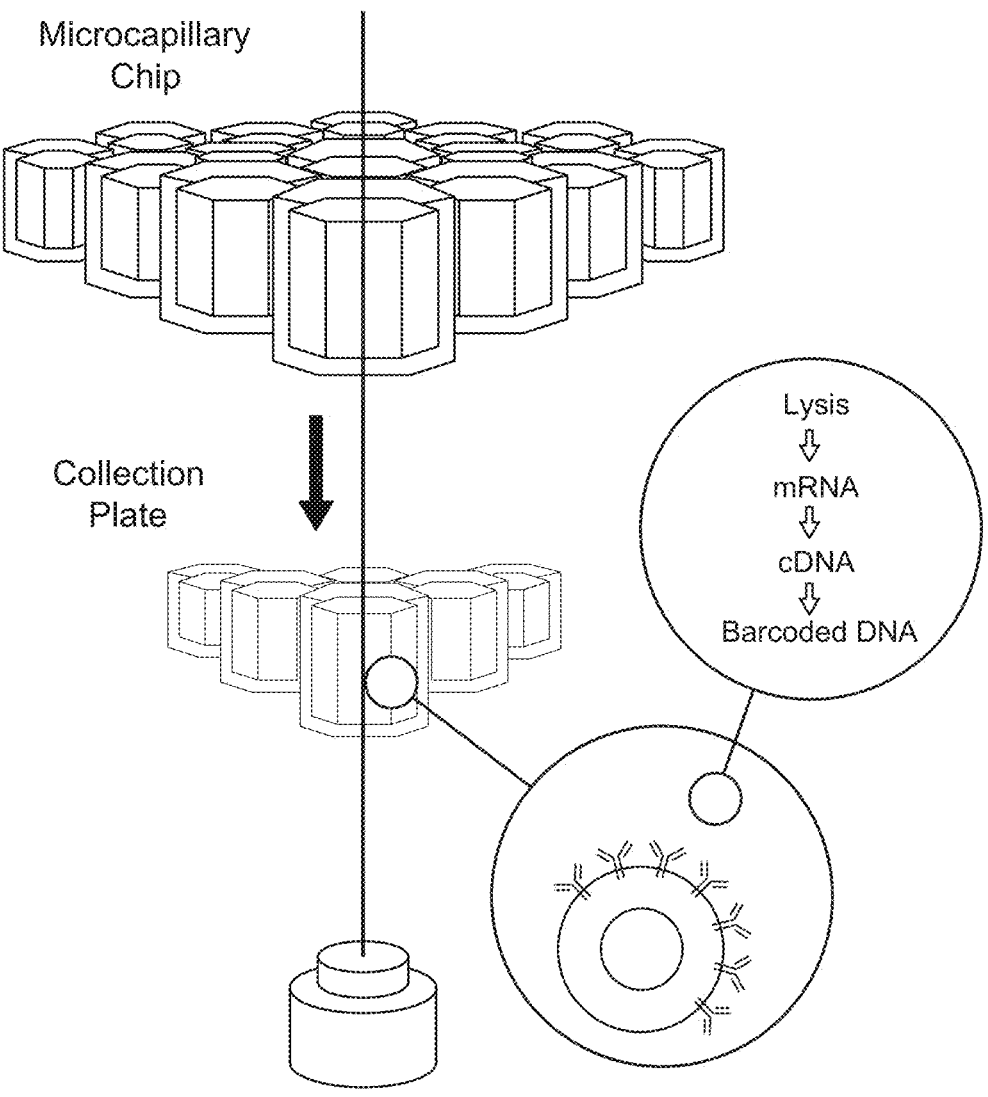
FIG. 14 shows a method to recover a cell with desired functional activity via a laser as discussed in Example 2.
Figure 15:
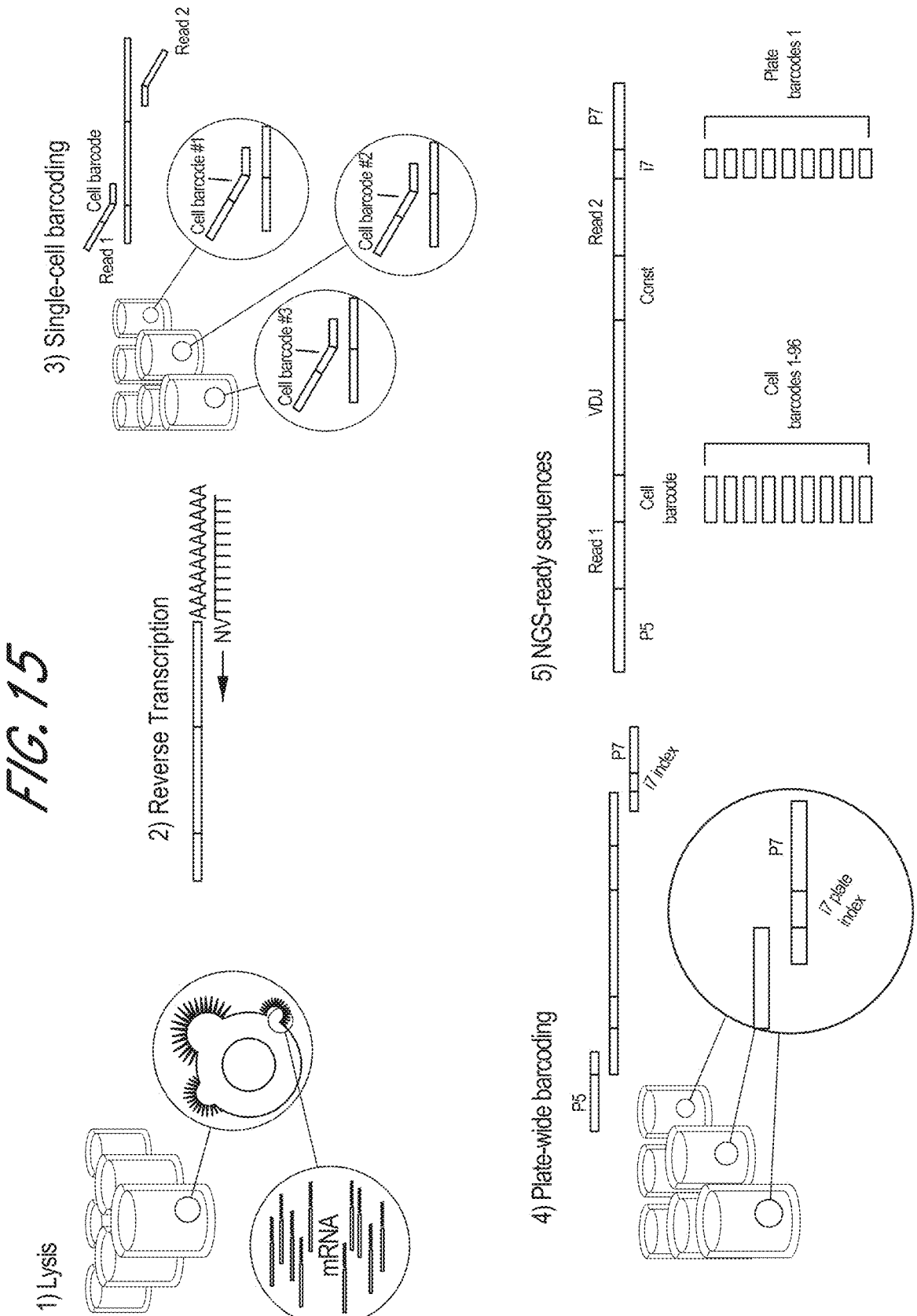
FIG. 15 shows reverse transcription (RT) and polymerase chain reaction (PCR) preparation for Next-Generation Sequencing (NGS).

In another example, the present disclosure further comprises methods of recovering desired genetic material from cells with desired phenotype in microcapillaries. A high level overview is presented below and in FIGS. 14 and 15:

Step 1: In this step, cells with desired functional activity are recovered via a laser based on the methods comprised in the present disclosure.

Figure 16:
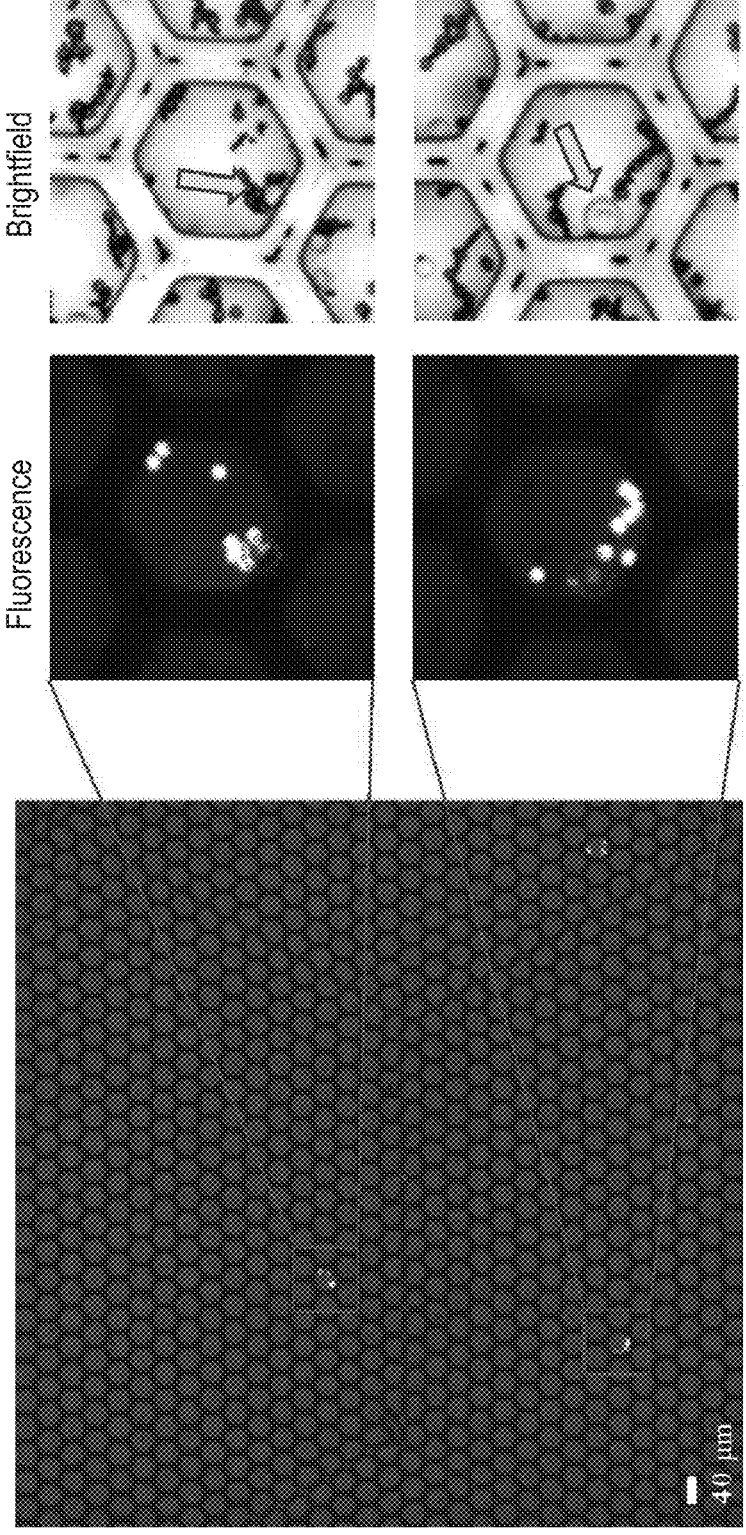
FIG. 16 shows the binding analysis of the xPloration B assay discussed in Example 2.
Figure 17:
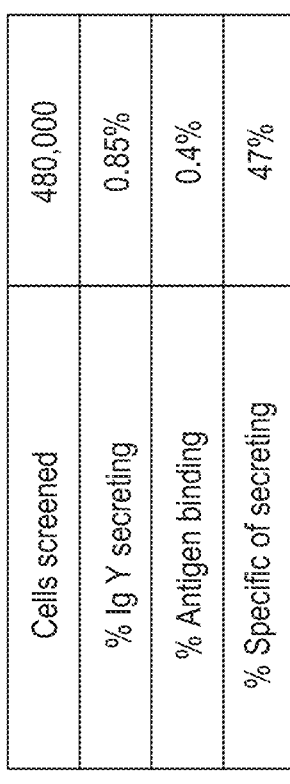
FIG. 17 provides the results from the quantification and sorting steps of the xPloration B cell assay discussed in Example 2.
Figure 17:
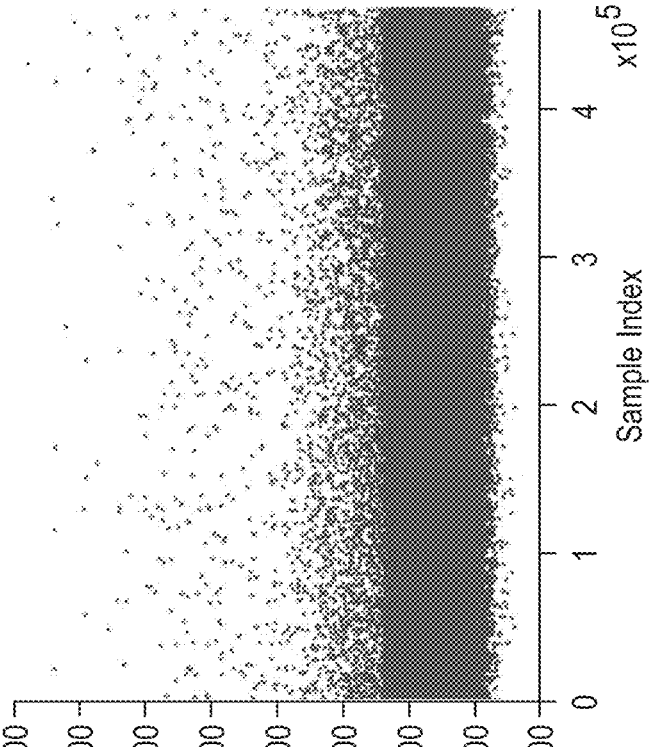

Step 2: Next, the cells undergo RT and PCR preparation for NGS based on the methods comprised in the present disclosure. These steps include lysis, reverse transcription, single cell barcoding, plate-wide barcoding, and result in NGS ready sequences.

xPloration B cell assay: First, mAb secretor (OmniChicken splenocytes (~1 cell/μPore)) and target beads (progranulin-biotin on streptavidin beads (2.8 μm)) were combined. Next, cells were loaded with the detection antibody (goat anti-Chicken IgY (H+L)-Alexa Fluor 488) into the array, creating a homogenous assay. The cells were incubated for three hours, and then they were imaged and the data was quantified. The binding analysis is shown in FIG. 16 and the quantification and sorting is shown in FIG. 17.

Figure 18:
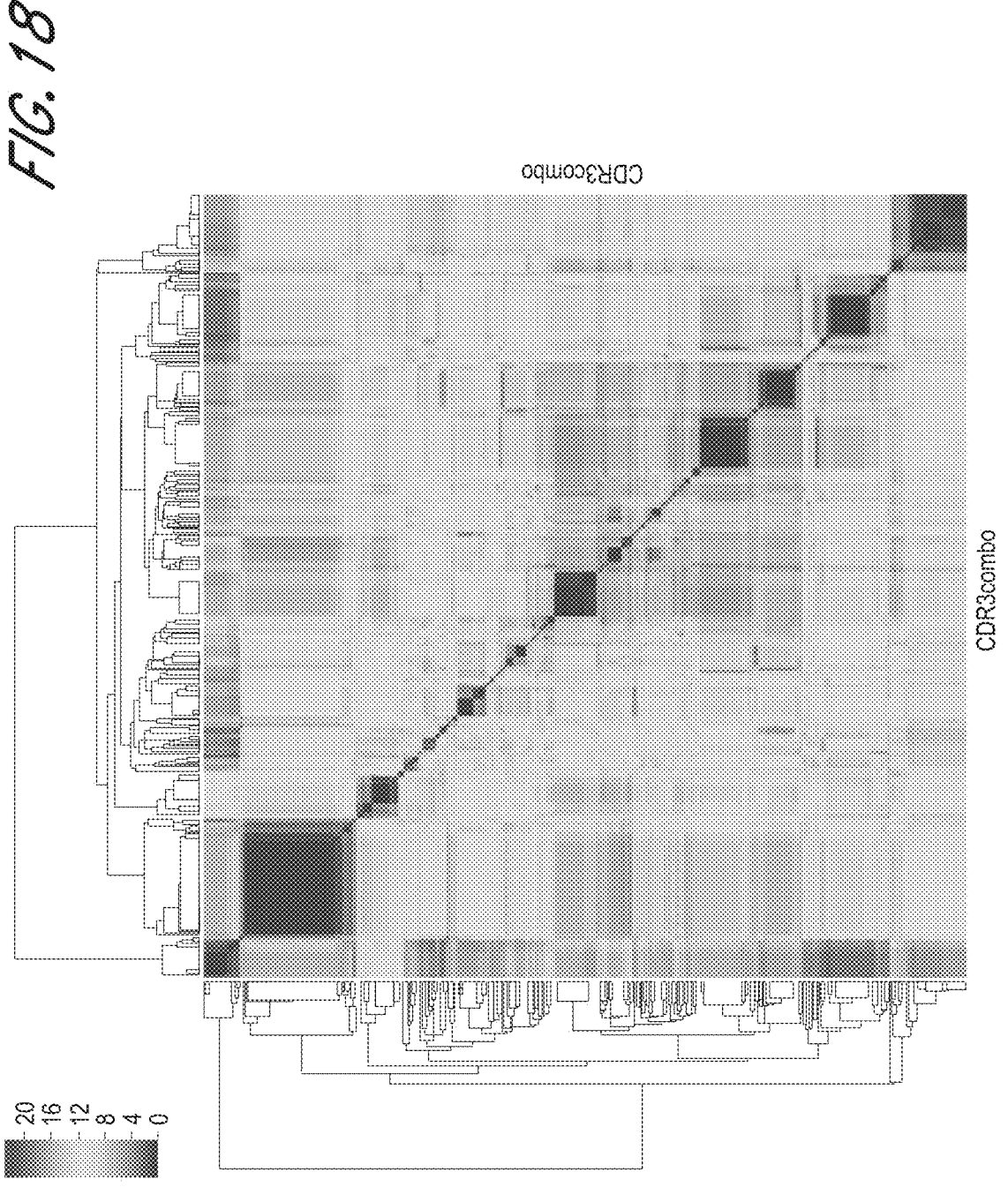
FIG. 18 provides a heat map of the pairwise distance between each cells concatenated HCDR3-LCDR3 measured in the xPloration B cell assay discussed in Example 2.

Expanded NGS Panel: Post screen, the cells were isolated in a 96 well plate. Single cell reverse transcription was performed, followed by separate amplification of the variable heavy chain and variable light chain. The total number of cells with paired heavy and light chains that were recovered was 569 (75%). The total unique H3/L3 clonotypes was 280. The total number of unique sequences was 485. Pairwise distance between each cell's concatenated HCDR3-LCDR3 is shown in FIG. 18.

Figure 19:
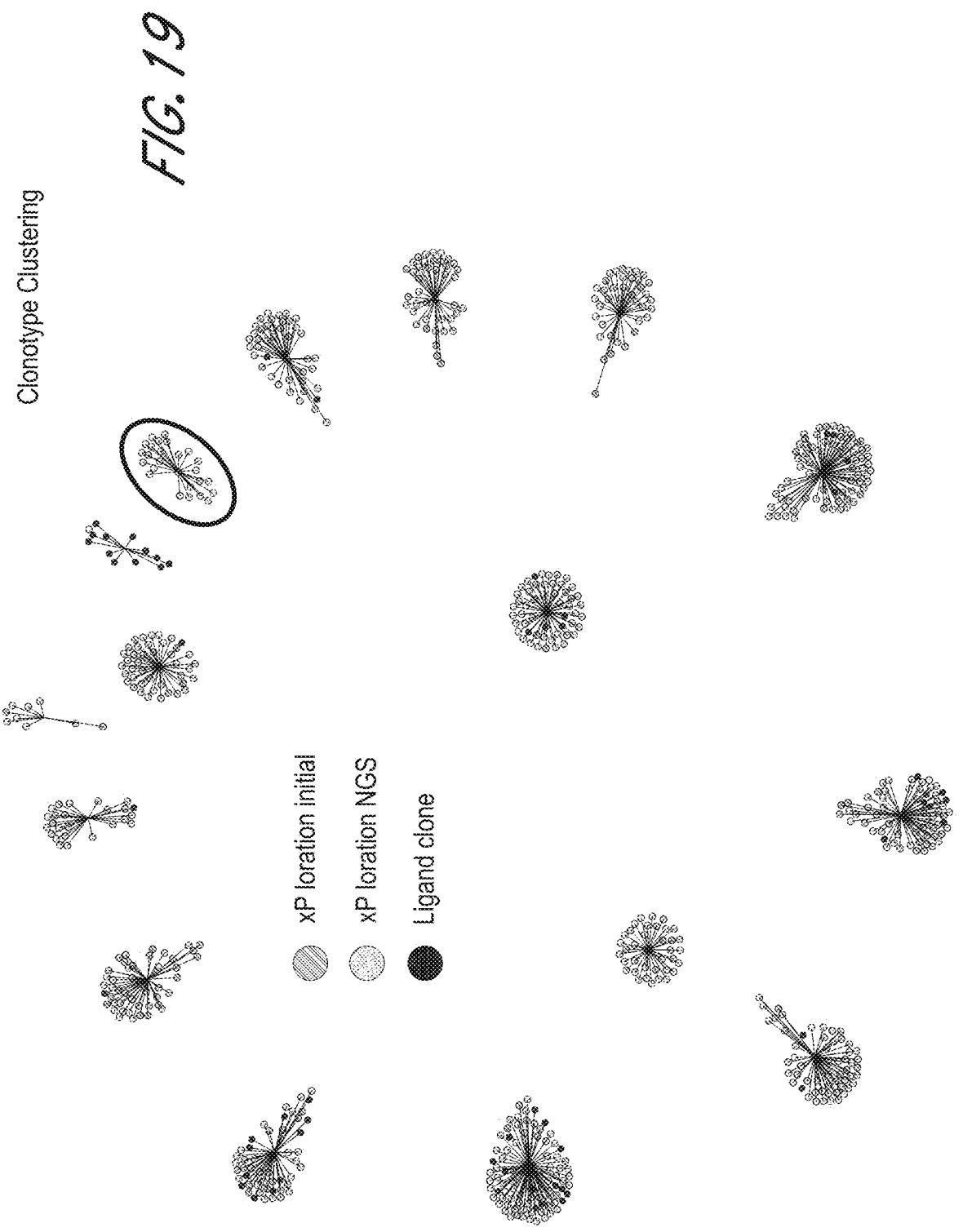
FIG. 19 shows clonotype clustering results of the xPloration B cell assay as discussed in Example 2.
Figure 20:
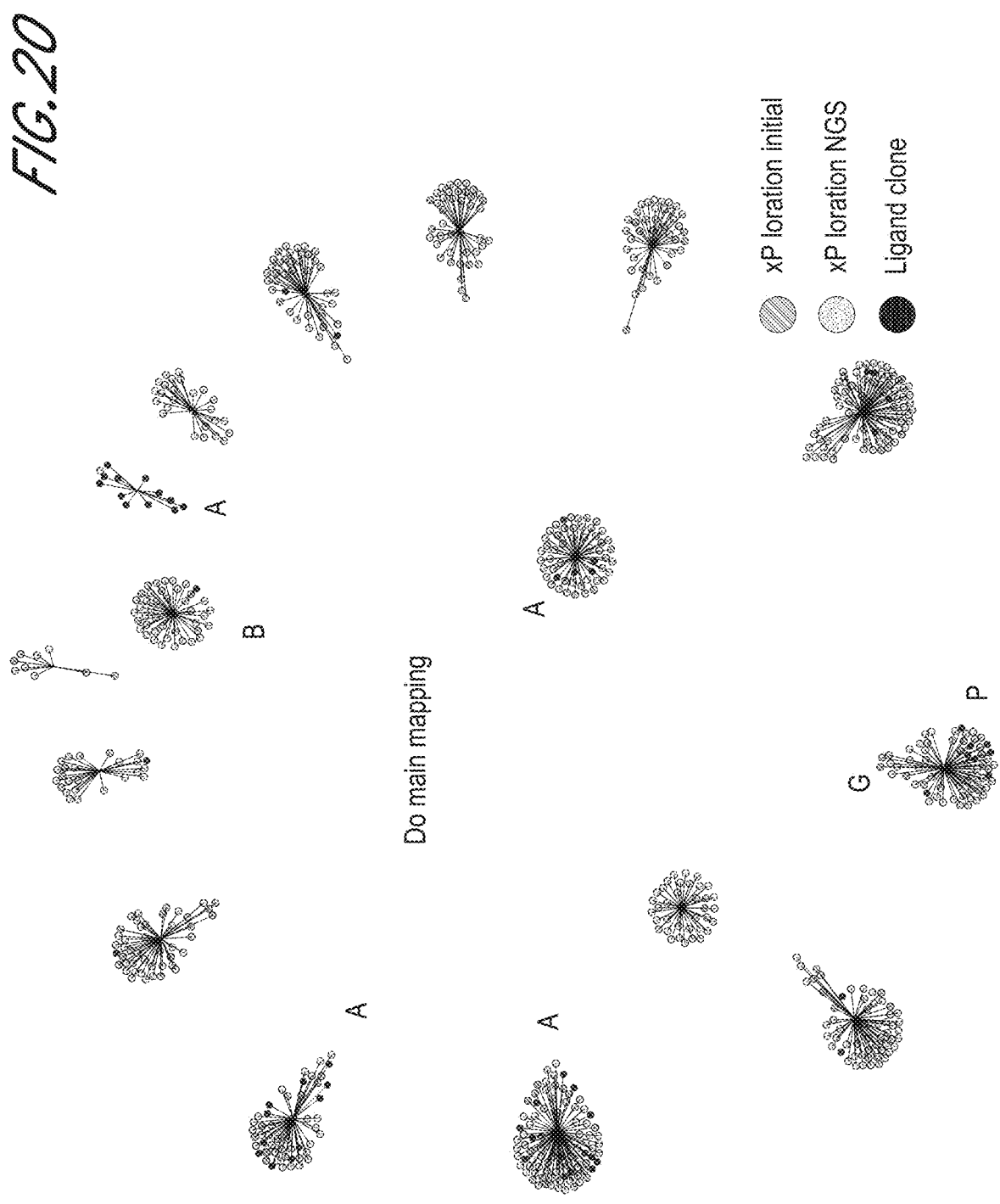
FIG. 20 shows distinct subdomains of progranulin, with broad coverage of the target subdomains (A, B, G, P) as discussed in Example 2.
Figure 21:
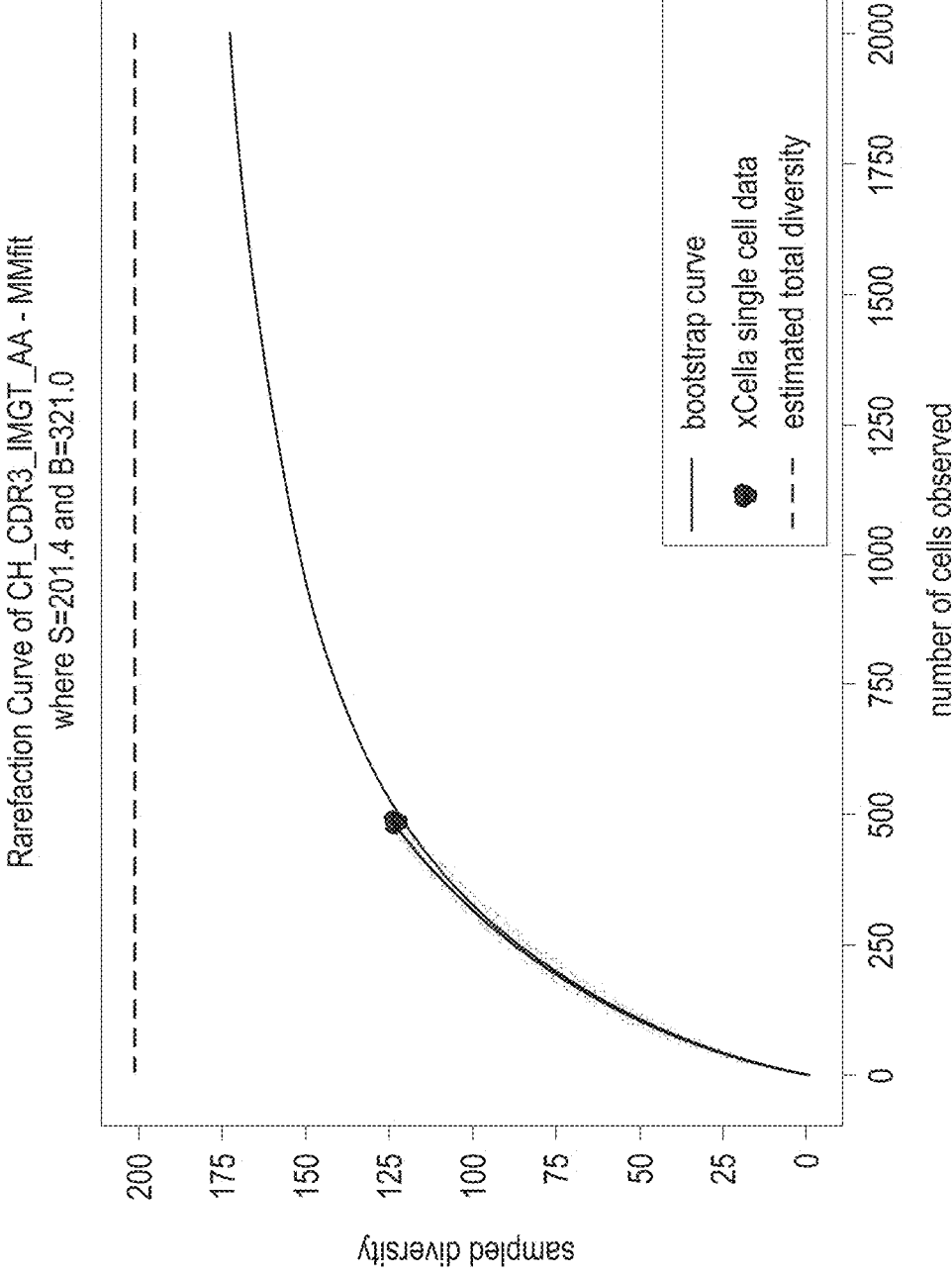
FIG. 21 shows the rarefaction curve of CDR3.
Figure 22:
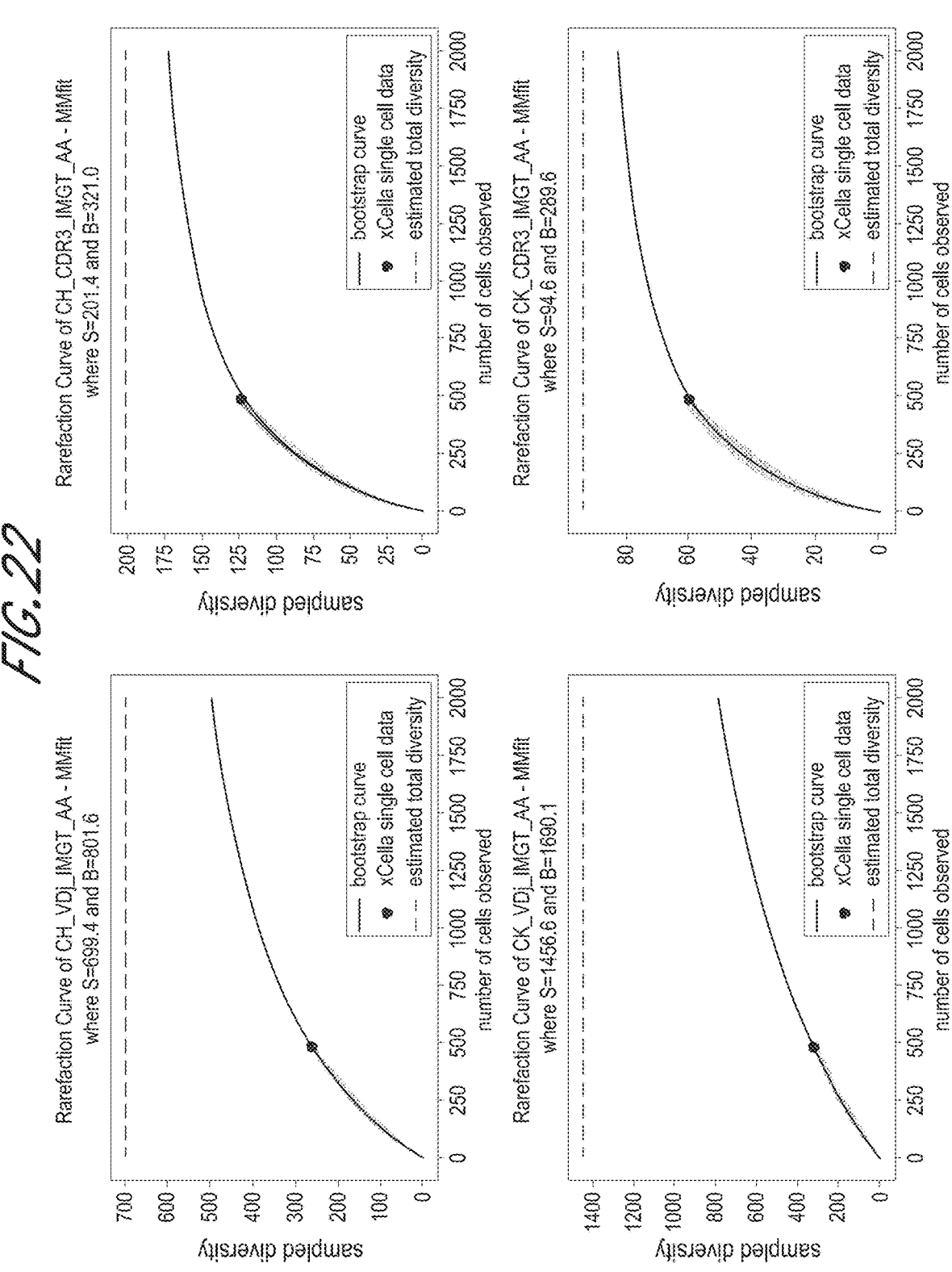
FIG. 22 shows rarefaction curves of H3, L3, VH, and VK.

Results: The results of the experiments show that deeper characterization identifies new clonotype families (See FIG. 19). The xPloration screen identified the majority of clonotypes identified by the Gel Encapsulated Microenvironment (GEM) assay (as described in Izquierdo et al., High-efficiency antibody discovery achieved with multiplexed microscopy, Microscopy, 2016, 65(4): 341-352, herein incorporated by reference for assay procedures), and multiple new clonotypes were also identified with xPloration. The NGS sequencing added support to new clusters and revealed even more diversity. Antigen specific clones were show to have high affinity and broad epitopic coverage. Ligand expressed subsets of discovered clones as sc-Fv. Characterization via carterra LSA (affinity and epitope binning data). Clusters mapped to distinct subdomains of progranulin, with broad coverage of the target subdomains (A, B, G, P) (See FIG. 20). Deeper characterization also allows for estimates of antibody diversity (See FIG. 21). Using the equation $S=nS_{max}(n+B)$, where S is the number of unique sequences, n is the total number of sequences, Smax is the maximum number of unique sequences, and B is a fitting constant, rarefaction curves were fit to the data using bootstrap sampling. The estimated total diversity (% captured by NGS set) for H3 was 201 (62%), for L3 was 95 (65%), for VH was 700 (32%), for VK was 1450 (22%) as shown in FIG. 22.

While embodiments and applications of the present invention have been described in some detail by way of illustration and example, it would be apparent to those of skill in the art that many additional modifications would be possible without departing from the inventive concepts contained herein. All references cited herein are hereby incorporated in their entirety.

What is claimed is:

1. A method for recovering content of a sample from a microcapillary array comprising a plurality of microcapillary wells, wherein the method comprises:

(A) positioning a laser to target a first microcapillary well in the plurality of microcapillary wells, each of the plurality of microcapillary wells comprising a through hole extending from a first planar surface of the microcapillary array to a second planar surface of the microcapillary array;

(B) pulsing the laser at least one time towards the first microcapillary well; and (C) extracting the content from the first microcapillary well, thereby recovering the content of the first microcapillary well.

2. The method of claim 1, wherein the method further comprises, prior to the positioning the laser (A), identifying the first microcapillary well.

3. The method of claim 1, wherein the pulsing the laser (B) further comprises pulsing the laser towards one or more subsections of the first microcapillary well.

4. The method of claim 1, wherein the pulsing the laser (B) further comprises pulsing the laser more than one time and pulsing the laser in more than one subsection of the first microcapillary well.

5. The method of claim 4, wherein the laser pulses a plurality of subsections of the first microcapillary well in a range of from 2 subsections to 10 subsections.

6. The method of claim 4, wherein each laser pulse has a duration in a range of from 5 nanoseconds (ns) to 20 ns.

7. The method of claim 1, wherein the content comprises one or more intact cells.

8. The method of claim 1, wherein the extracting and recovering (C) further comprise imaging the content during the recovery of the content.

9. The method of claim 1, wherein the positioning the laser (A) is performed using a laser guiding system.

10. The method of claim 1, wherein a wavelength of light emitted from the laser is in a range of from 213 nanometers (nm) to 1380 nm.

11. The method of claim 1, wherein the laser pulses in a range of from 100 pulses per second to 1000 pulses per second.

12. The method of claim 1, wherein the laser pulses at 20,000 to 120,000 Hz and 10-1000 pulses total.

13. The method of claim 1, wherein positioning the laser (A) further comprises imaging the content of the first microcapillary well using a laser guiding system.

14. The method of claim 1, wherein the laser guiding system further comprises one or more spatial light modulators to alter a shape of a beam emitted from the laser.

15. The method of claim 1, wherein the content of the extracting and recovering (C) is disposed onto a collection slide.

16. The method of claim 1, wherein the method further comprises, following the extracting and the recovering (C), disposing the content onto a collection slide and transferring the content of the collection slide to a PCR plate and freezing the PCR plate.

17. The method of claim 1, wherein the content comprises genetic material and wherein the sample comprises one or more intact cells with a desired phenotype.

18. The method of claim 17, wherein the one or more cells are B cells.

19. The method of claim 17, wherein the genetic material comprises an antibody sequence.

20. The method of claim 19, wherein the antibody sequence comprises a heavy chain and a light chain.

21. The method of claim 20, wherein the genetic material comprises mRNA.

22. The method of claim 21, wherein reverse transcription is performed on the mRNA.

23. The method of claim 22, wherein the RT-PCR amplification further comprises one or more single cell specific DNA level barcodes.

24. The method of claim 22, wherein the RT-PCR amplification further comprises one or more single cell specific DNA level barcodes, wherein the same barcode is added to the heavy chain and the light chain of an antibody sequence being amplified.

25. The method of claim 22, wherein the RT-PCR amplification of the heavy chain and the light chain is performed in separate reactions.

26. The method of claim 25, wherein the RT-PCR amplification of the heavy chain and the light chain is performed in a single reaction vessel.

27. The method of claim 1, wherein the content comprises genetic material and wherein the sample comprises one or more intact cells with a desired phenotype, and wherein single-cell NGS sequencing is employed to determine the genetic phenotype.

* * * * *